(12) United States Patent
Loria

(10) Patent No.: US 11,564,789 B2
(45) Date of Patent: *Jan. 31, 2023

(54) HAIR IMPLANTS COMPRISING ENHANCED ANCHORING AND MEDICAL SAFETY FEATURES

(71) Applicant: Loria Products LLC, Miami, FL (US)

(72) Inventor: Victor Loria, Miami, FL (US)

(73) Assignee: Loria Products LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/635,849

(22) PCT Filed: Jul. 30, 2018

(86) PCT No.: PCT/US2018/044298
§ 371 (c)(1),
(2) Date: Jan. 31, 2020

(87) PCT Pub. No.: WO2019/027864
PCT Pub. Date: Feb. 7, 2019

(65) Prior Publication Data
US 2022/0061981 A1    Mar. 3, 2022

Related U.S. Application Data

(63) Continuation-in-part of application No. 15/718,637, filed on Sep. 28, 2017, now Pat. No. 10,105,212, and
(Continued)

(51) Int. Cl.
*A61F 2/00* (2006.01)
*A61F 2/10* (2006.01)

(52) U.S. Cl.
CPC ........ *A61F 2/10* (2013.01); *A61F 2002/0081* (2013.01); *A61F 2220/0008* (2013.01);
(Continued)

(58) Field of Classification Search
CPC .............. A61F 2/10; A61F 2250/0071; A61B 2017/00752; A61B 2017/0411; A61B 2018/00476
See application file for complete search history.

(56) References Cited

U.S. PATENT DOCUMENTS

| 3,003,155 A | 10/1961 | Mielzynsky |
| 3,596,292 A | 8/1971 | Erb et al. |

(Continued)

FOREIGN PATENT DOCUMENTS

| BE | 1017068 | 1/2008 |
| CO | 0864044 | 6/2008 |

(Continued)

OTHER PUBLICATIONS

English abstract of KR20160107021.
(Continued)

*Primary Examiner* — Jacqueline Woznicki
(74) *Attorney, Agent, or Firm* — Caesar Rivise, PC

(57) ABSTRACT

A hair implant includes: (a) a hair strand anchor including: an anchor body; at least one hair chamber disposed within the anchor body; and at least one tunnel through the anchor body, where the tunnel is free of a hair; and (b) at least one hair strand having a portion thereof retained in the at least one of the hair chamber; wherein the tunnel is configured to support collagen ligature growth after subcutaneous implantation by receiving and retaining collagen ligatures that anchor the hair implant to a hair implant recipient. Also disclosed is a hair implant including an anchor with first and second anchor bodies and at least one bridge connecting the anchor bodies and bridging at least one void between the anchor bodies, wherein the bridge supports and retains
(Continued)

collagen ligature growth. One-piece implants are also disclosed, as are anchors, hair restoration and manufacturing methods.

24 Claims, 41 Drawing Sheets

Related U.S. Application Data a continuation-in-part of application No. 15/665,369, filed on Jul. 31, 2017, now Pat. No. 9,993,334.

(52) U.S. Cl.
CPC . *A61F 2230/006* (2013.01); *A61F 2230/0008* (2013.01); *A61F 2230/0013* (2013.01); *A61F 2250/0071* (2013.01)

(56) References Cited

U.S. PATENT DOCUMENTS

| | | |
|---|---|---|
| 3,699,969 A | 10/1972 | Allen |
| 3,862,453 A | 1/1975 | Widdifield |
| 3,998,230 A | 12/1976 | Miller |
| 4,032,685 A | 6/1977 | Yamada |
| 4,126,124 A | 11/1978 | Miller |
| D251,184 S | 2/1979 | Volk |
| 4,210,145 A | 7/1980 | Nestor et al. |
| D276,594 S | 12/1984 | Fahey et al. |
| D277,650 S | 2/1985 | Mulvaney |
| 4,588,408 A | 5/1986 | Yamada |
| D290,820 S | 7/1987 | Slovak |
| 4,812,120 A | 3/1989 | Flanagan et al. |
| 4,834,119 A | 5/1989 | Yamada |
| 4,944,752 A | 7/1990 | Santi |
| 4,969,903 A * | 11/1990 | Valle .................. A61F 2/10 128/898 |
| 5,061,284 A | 10/1991 | Laghi |
| 5,137,533 A | 8/1992 | Giampapa |
| D333,629 S | 3/1993 | Johnson |
| D339,438 S | 9/1993 | Moran |
| D351,465 S | 10/1994 | Stringer et al. |
| D351,466 S | 10/1994 | Stringer et al. |
| D354,592 S | 1/1995 | Powers |
| 5,417,683 A | 5/1995 | Shiao |
| 5,485,649 A | 1/1996 | Miceli |
| D377,095 S | 12/1996 | Michelson |
| D377,096 S | 12/1996 | Michelson |
| D392,871 S | 3/1998 | Chang |
| 5,767,152 A | 6/1998 | Nielsen et al. |
| 5,792,169 A | 8/1998 | Markman |
| 5,800,545 A | 9/1998 | Yamada et al. |
| D399,151 S | 10/1998 | Fisher et al. |
| D400,455 S | 11/1998 | Fisher |
| D402,757 S | 12/1998 | Davis et al. |
| D404,628 S | 1/1999 | Kendrick |
| D405,335 S | 2/1999 | Lin |
| 5,888,202 A | 3/1999 | Amiri |
| 5,957,901 A | 9/1999 | Mottola et al. |
| 6,027,512 A | 2/2000 | Bridges |
| D434,223 S | 11/2000 | Dombrowski |
| D439,336 S | 3/2001 | Najmi |
| D446,941 S | 8/2001 | Kraemer |
| D465,279 S | 11/2002 | Etter et al. |
| 6,482,232 B1 | 11/2002 | Boucher et al. |
| D472,827 S | 4/2003 | Harju et al. |
| D478,267 S | 8/2003 | Chen |
| D481,963 S | 11/2003 | Onuma et al. |
| D484,242 S | 12/2003 | Wilkinson |
| D492,995 S | 7/2004 | Rue et al. |
| D497,259 S | 10/2004 | Lion et al. |
| D510,863 S | 10/2005 | Juhng et al. |
| D519,031 S | 4/2006 | Snyder |
| D519,353 S | 4/2006 | Chen |
| D523,557 S | 6/2006 | Jones et al. |
| D535,170 S | 1/2007 | Caplan |
| D546,176 S | 7/2007 | Degn |
| D555,241 S | 11/2007 | Nakanishi |
| D573,866 S | 7/2008 | Smith |
| D580,052 S | 11/2008 | White |
| D581,212 S | 11/2008 | Macler |
| D584,640 S | 1/2009 | Castelnuovo-Tedesco |
| 7,491,226 B2 | 2/2009 | Palmaz et al. |
| D589,013 S | 3/2009 | Pozin et al. |
| D589,479 S | 3/2009 | Pozin et al. |
| D590,788 S | 4/2009 | Pozin et al. |
| D600,576 S | 9/2009 | Marcoz |
| D604,413 S | 11/2009 | Ikeya et al. |
| 7,621,958 B2 | 11/2009 | Zdeblick et al. |
| D606,190 S | 12/2009 | Pruitt et al. |
| D606,833 S | 12/2009 | Robinson |
| D608,545 S | 1/2010 | Yu et al. |
| D621,938 S | 8/2010 | Petersen et al. |
| D622,853 S | 8/2010 | Raven, III |
| D623,751 S | 9/2010 | Weiman |
| D625,822 S | 10/2010 | Lewis et al. |
| D627,056 S | 11/2010 | Quensel |
| D627,468 S | 11/2010 | Richter et al. |
| D628,917 S | 12/2010 | Tian |
| D634,421 S | 3/2011 | El-Gad et al. |
| D635,271 S | 3/2011 | Azar et al. |
| D640,470 S | 6/2011 | Spagnuolo |
| D641,475 S | 7/2011 | Graham |
| D641,876 S | 7/2011 | Graham |
| D643,121 S | 8/2011 | Milford et al. |
| D649,633 S | 11/2011 | Claypool et al. |
| D655,010 S | 2/2012 | Wenk et al. |
| D657,873 S | 4/2012 | Khalil et al. |
| 8,177,557 B2 | 5/2012 | Delmonico et al. |
| D679,391 S | 4/2013 | Chinowsky et al. |
| D681,292 S | 4/2013 | Fujiwara et al. |
| D697,036 S | 1/2014 | Kay et al. |
| D711,531 S | 8/2014 | Ozawa et al. |
| D718,106 S | 11/2014 | Lauzet |
| D719,739 S | 12/2014 | Brescia et al. |
| D721,435 S | 1/2015 | Patterson et al. |
| D726,316 S | 4/2015 | Marquez |
| D728,943 S | 5/2015 | Carpentier |
| D730,217 S | 5/2015 | Yokino et al. |
| D731,056 S | 6/2015 | Tsai |
| D733,599 S | 7/2015 | Yokino et al. |
| D733,882 S | 7/2015 | Fregoso et al. |
| D735,404 S | 7/2015 | Gourmet |
| D740,940 S | 10/2015 | Fregoso et al. |
| D747,228 S | 1/2016 | Fiedler et al. |
| D747,477 S | 1/2016 | Freigang et al. |
| D754,346 S | 4/2016 | Pimenta et al. |
| D761,427 S | 7/2016 | Patterson et al. |
| D761,998 S | 7/2016 | Pinder |
| D771,812 S | 11/2016 | Shayle |
| D771,956 S | 11/2016 | Hauger et al. |
| 9,492,196 B2 | 11/2016 | Keren et al. |
| D774,310 S | 12/2016 | Hauger |
| 9,510,940 B2 | 12/2016 | Chen et al. |
| D779,670 S | 2/2017 | Kyystyniak et al. |
| D787,054 S | 5/2017 | Rini et al. |
| D787,680 S | 5/2017 | Donohue |
| D790,615 S | 6/2017 | Nowak et al. |
| D791,936 S | 7/2017 | Davis et al. |
| D795,596 S | 8/2017 | Salm |
| D796,354 S | 9/2017 | Chan et al. |
| D799,743 S | 10/2017 | Qiu |
| D800,566 S | 10/2017 | Wieland |
| D801,523 S | 10/2017 | Khour |
| D801,622 S | 11/2017 | Koo |
| D802,308 S | 11/2017 | Salm |
| D806,244 S | 12/2017 | Rezac et al. |
| D809,656 S | 2/2018 | Lau et al. |
| D813,001 S | 3/2018 | Whitcomb |
| D813,375 S | 3/2018 | Dilworth |
| D814,197 S | 4/2018 | Salm |
| D817,279 S | 5/2018 | Lin et al. |
| D818,636 S | 5/2018 | Qiu |
| D819,337 S | 6/2018 | Yuan et al. |

(56) References Cited

U.S. PATENT DOCUMENTS

| | | |
|---|---|---|
| D821,100 S | 6/2018 | Sanghi |
| 9,993,334 B1 | 6/2018 | Loria |
| D824,177 S | 7/2018 | Salm |
| D829,446 S | 10/2018 | Katsuma |
| D831,199 S | 10/2018 | Holton et al. |
| 10,105,212 B1 | 10/2018 | Loria |
| D833,064 S | 11/2018 | Verleur et al. |
| D834,246 S | 11/2018 | Qiu |
| D834,369 S | 11/2018 | Gettig |
| D835,841 S | 12/2018 | Xu |
| D837,297 S | 1/2019 | Muroi |
| D837,371 S | 1/2019 | Zu |
| D837,372 S | 1/2019 | Zu |
| D838,494 S | 1/2019 | Fischer |
| 10,182,807 B2 | 1/2019 | Bridgeman et al. |
| D851,760 S | 6/2019 | Lee |
| D856,588 S | 8/2019 | French-Artis |
| D857,333 S | 8/2019 | Axelrod et al. |
| D857,469 S | 8/2019 | Whitcomb |
| D858,247 S | 9/2019 | Papafagos |
| D858,282 S | 9/2019 | Han |
| D858,637 S | 9/2019 | Ballot et al. |
| D858,770 S | 9/2019 | Lintula et al. |
| D860,450 S | 9/2019 | Asfora et al. |
| D865,072 S | 10/2019 | Gambucci |
| D865,956 S | 11/2019 | Harding et al. |
| D867,764 S | 11/2019 | Stubbs |
| D867,840 S | 11/2019 | Macor |
| D869,656 S | 12/2019 | Adams |
| D869,849 S | 12/2019 | Chen et al. |
| D870,282 S | 12/2019 | Adams |
| D870,283 S | 12/2019 | Adams |
| D870,889 S | 12/2019 | Miller |
| D873,025 S | 1/2020 | Kim |
| D873,031 S | 1/2020 | Martensson |
| D873,518 S | 1/2020 | Chavez et al. |
| D874,650 S | 2/2020 | Horan et al. |
| D876,628 S | 2/2020 | Siman |
| 10,561,490 B2 | 2/2020 | Loria |
| D877,906 S | 3/2020 | Linder et al. |
| 10,588,525 B2 | 3/2020 | Someya et al. |
| D880,871 S | 4/2020 | Choi et al. |
| D882,070 S | 4/2020 | Inoh et al. |
| D882,085 S | 4/2020 | Sweeney et al. |
| D882,087 S | 4/2020 | Sarig et al. |
| D882,270 S | 4/2020 | Bloch et al. |
| D882,274 S | 4/2020 | Han |
| D884,176 S | 5/2020 | Jury et al. |
| D884,177 S | 5/2020 | Orion et al. |
| D885,059 S | 5/2020 | Capalungan et al. |
| D885,665 S | 5/2020 | Richter et al. |
| 10,646,217 B2 | 5/2020 | Pisarnwongs et al. |
| D887,125 S | 6/2020 | Schubert |
| D887,126 S | 6/2020 | Schubert |
| D888,240 S | 6/2020 | Parcon |
| D888,435 S | 6/2020 | Damavandi et al. |
| D888,957 S | 6/2020 | Pikkula et al. |
| 10,682,223 B2 | 6/2020 | Loria |
| D890,341 S | 7/2020 | Wohnhaas et al. |
| D890,987 S | 7/2020 | Lorenz et al. |
| D891,117 S | 7/2020 | Theodosis et al. |
| D892,323 S | 8/2020 | Sloss |
| D893,198 S | 8/2020 | Kaicker |
| D894,610 S | 9/2020 | Albay et al. |
| D895,828 S | 9/2020 | Marshall |
| D896,385 S | 9/2020 | Lim et al. |
| D898,531 S | 10/2020 | Kerr |
| D901,178 S | 11/2020 | Kim et al. |
| D903,111 S | 11/2020 | Pupino et al. |
| D904,616 S | 12/2020 | DaCosta et al. |
| 10,925,718 B2 | 2/2021 | Loria |
| 2003/0036770 A1 | 2/2003 | Markman |
| 2003/0195625 A1 | 10/2003 | Castro et al. |
| 2004/0149301 A1 | 8/2004 | Arroyo et al. |
| 2005/0191748 A1 | 9/2005 | Barrows |
| 2005/0267506 A1 | 12/2005 | Harris |
| 2007/0067033 A1 | 3/2007 | Bonati |
| 2007/0282364 A1 | 12/2007 | Haber |
| 2010/0305699 A1 | 12/2010 | Kim |
| 2011/0046639 A1 | 2/2011 | Giotis |
| 2012/0245612 A1* | 9/2012 | Keren ............... A61F 2/10 606/187 |
| 2016/0345648 A1 | 12/2016 | Miniello et al. |
| 2017/0099901 A1 | 4/2017 | Lee |
| 2017/0265896 A1 | 9/2017 | Keren |
| 2019/0117378 A1 | 4/2019 | Loria |
| 2019/0160289 A1 | 5/2019 | Kluger et al. |
| 2019/0380827 A1 | 12/2019 | Loria |
| 2020/0155300 A1 | 5/2020 | Bae et al. |
| 2020/0253716 A1 | 8/2020 | Lim |
| 2021/0145476 A1 | 5/2021 | Franco et al. |

FOREIGN PATENT DOCUMENTS

| | | |
|---|---|---|
| DE | 2912043 A1 | 1/1980 |
| JP | H10234754 | 9/1998 |
| JP | 2014065981 | 4/2014 |
| KR | 101503014 B1 | 3/2015 |
| KR | 20160107021 A | 9/2016 |
| WO | WO8909575 A1 | 10/1989 |
| WO | WO 00/15270 | 3/2000 |
| WO | WO 2006/041265 | 4/2006 |
| WO | WO2007/068401 A1 | 6/2007 |
| WO | WO 2010/078311 | 7/2010 |
| WO | WO 2014/196643 | 12/2014 |
| WO | WO2016/016722 A2 | 2/2016 |
| WO | WO 2017/180370 | 10/2017 |
| WO | WO 2019/027864 | 2/2019 |

OTHER PUBLICATIONS

International Search Report for related European Patent Application No. EP18841122 dated Mar. 19, 2021.
English Abstract of WO 00/15270.
Office Action re related Chilean Patent Application No. 202000280 dated May 25, 2021 (with English translation).
International Search Report for related PCT Application No. PCT/US2018/044298 dated Oct. 1, 2018.
Ahdout et al. (2012). Weft hair extensions causing a distinctive horseshoe pattern of traction alopecia. Journal of the American Academy of Dermatology, 67(6), e294-e295.
Aktas et al. (2016) Could Topical Minoxidil Cause Non-Arteritic Anterior Ischemic Optic Neuropathy?. Journal of clinical and diagnostic research: JCDR, 10(8), WD01:1-2.
Avitzur, O. (2013). The dangers of hair extensions: The beauty trend can cause headaches, baldness, and allergic reactions. Consumer Reports. Retrieved on Aug. 7, 2017 from https://www.consumerreports.org/cro/2013/02/the-dangers-of-hair-extensions/index.htm.
Avram et al. (2014). Side-effects from follicular unit extraction in hair transplantation. Journal of cutaneous and aesthetic surgery, 7(3), 177-179.
Barrera, A. (2005). Reconstructive hair transplantation of the face and scalp. In Seminars in Plastic Surgery 19(2): pp. 159-166.
Barrese et al. (2016). Scanning electron microscopy of chronically implanted intracortical microelectrode arrays in non-human primates. Journal of neural engineering, 13(2), 026003: 1-44.
Bascom, J. (1983). Pilonidal disease: long-term results of follicle removal. Diseases of the colon & rectum, 26(12), 800-807.
Benedetto et al. (2005). Pilonidal sinus disease treated by depilation using an 800 nm diode laser and review of the literature. Dermatologic surgery, 31(5), 587-591.
Bernard, B. A. (2016). Advances in understanding hair growth. F1000Research, 5: 1-8.
Bernstein, R. (2009). Psychological Aspects of Balding. Bernstein Medical Center for Hair Restoration. Retrieved on Aug. 4, 2017 from https://www.bernsteinmedical.com/hair-loss/basics/psychology-of-balding/.
Biofibre (2015). Hair Implant Safety. Biofibre: High Technology Hair Implant System. Retrieved on Aug. 7, 2017 from http://www.biofibre.com/en/hair-implants/safety/.

(56) References Cited

OTHER PUBLICATIONS

Biofibre (2015). Results. Biofibre: High Technology Hair Implant System. Retrieved on Aug. 7, 2017 from http://wwwbiofibre.com/en/results/.

Bryers et al. (2012). Engineering biomaterials to integrate and heal: the biocompatibility paradigm shifts. Biotechnology and bioengineering, 109(8), 1898-1911.

Cash, T. F. (1992). The psychological effects of androgenetic alopecia in men. Journal of the American Academy of Dermatology, 26(6), 926-931.

Chavoin et al. (2016). Correction of congenital malformations by custom-made silicone implants: Contribution of computer-aided design. Experience of 611 cases. In Annales de chirurgie plastique et esthetique, vol. 61, No. 5, pp. 694-702.

Chellini et al. (2015). Generalized hypertrichosis induced by topical Minoxidil in an adult woman. International journal of trichology, 7(4), 182-183.

Cochrane Database of Systematic Reviews: Plain Language Summaries (2008). Treatments for alopecia areata, alopecia totalis, and alopecia universalis. Plain Language Summary of Delamere (2008). Interventions for alopecia areata. The Cochrane Library. Art. No. CD004413. p. 1.

Cochrane Database of Systematic Reviews: Plain Language Summaries (2016). Treatments for female pattern hair loss. Plain Language Summary of van Zuuren et al. (2016). Interventions for female pattern hair loss. Cochrane Database of Systematic Reviews 2016, Issue 5. Art. No. CD007628, p. 1-2.

Cotsarelis et al. (2001). Towards a molecular understanding of hair loss and its treatment. Trends in molecular medicine, 7(7), 293-301.

Duverger et al. (2014). To grow or not to grow: hair morphogenesis and human genetic hair disorders. Seminars in Dell & developmental biology. vol. 25: pp. 22-33.

Erlich et al. (2003). Nasal dorsal augmentation with silicone implants. Facial plastic surgery, 19(04), 325-330.

Fanous et al. (2003). Estimating implant size in chin augmentation: A simplified approach. Canadian Journal of Plastic Surgery, 11(3), 161-165.

Farrell et al. (2014). Effects of pore size, implantation time, and nano-surface properties on rat skin ingrowth into percutaneous porous titanium implants. Journal of Biomedical Materials Research Part A, 102(5), 1305-1315.

Federal Drug Administration (2016). Sec. 895.101 Prosthetic Hair Fibers. CFR Title 21, vol. 8, Chapter 1, Subchapter H, Part 895, Subpart B. Retrieved on Aug. 4, 2017 from https://www.accessdata.fda.gov/scripts/cdrh/cfdocs/cfcfr/CFRSearch.cfm?fr=895.101.

Fleckman et al. (2008). Models for the histologic study of the skin interface with percutaneous biomaterials. Biomedical Materials, 3(3), 034006:1-24.

Fleckman et al. (2012). Cutaneous and inflammatory response to long-term percutaneous implants of sphere-templated porous/solid poly (HEMA) and silicone in mice. Journal of Biomedical Materials Research Part A, 100(5), 1256-1268.

Fox et al. (2007). Traction folliculitis: an underreported entity. Cutis, 79(1), 26-30.

Gooding et al. (2004) The cadherin-catenin complex as a focal point of cell adhesion and signalling: new insights from three-dimensional structures. Bioessays, 26(5), 497-511.

Grice et al. (2011). The skin microbiome. Nature reviews. Microbiology, 9(4), 244-253.

Hanke et al. (1981). Hair implant complications. JAMA, 245(13), 1344-1345.

Hanke et al. (1981). Fiber implantation for pattern baldness. Am Acad Dermatol 4(3): 278-283.

Hartsock et al. (2008). Adherens and tight junctions: structure, function and connections to the actin cytoskeleton. Biochimica et Biophysica Acta (BBA)-Biomembranes, 1778(3), 660-669.

Hinderer, U. T. (1991). Nasal base, maxillary, and infraorbital implants—alloplastic. Clinics in plastic surgery, 18(1), 87-105.

Hirshburg et al. (2016). Adverse effects and safety of 5-alpha reductase inhibitors (finasteride, dutasteride): a systematic review. The Journal of clinical and aesthetic dermatology, 9(7), 56-62.

International Society of Hair Restoration Surgery (2003). Psychological effects of hair loss in women. Retrieved on Aug. 4, 2017 from http://www.ishrs.org/articles/hair-loss-effects.htm.

Jasterzbski et al. (2015). Pseudofolliculitis cutis: a vexing disorder of hair growth. British Journal of Dermatology, 172(4), 878-884.

Jones et al. (2013). Characterization of X-linked hypohidrotic ectodermal dysplasia (XL-HED) hair and sweat gland phenotypes using phototrichogram analysis and live confocal imaging. American Journal of Medical Genetics Part A, 161(7), 1585-1593.

Kaplan et al. (2012). A 5-year retrospective analysis of 5α-reductase inhibitors in men with benign prostatic hyperplasia: finasteride has comparable urinary symptom efficacy and prostate volume reduction, but less sexual side effects and breast complications than dutasteride. International journal of clinical practice, 66(11), 1052-1055.

Karaçal et al. (2012). Necrosis of the donor site after hair restoration with follicular unit extraction (FUE): a case report. Journal of Plastic, Reconstructive & Aesthetic Surgery, 65(4), e87-e89.

Karaman et al. (2006). Androgenetic alopecia: Does its presence change our perceptions?. International journal of dermatology, 45(5), 565-568.

Khanna et al. (2011). Pilonidal disease. Clinics in colon and rectal surgery, 24(01), 046-053.

Kong et al. (2012). Skin microbiome: looking back to move forward. Journal of Investigative Dermatology, 132(3), 933-939.

Konishi et al. (2012). Reshaping the eyebrow by follicular unit transplantation from excised eyebrow in extended infrabrow excision blepharoplasty. Clinical ophthalmology (Auckland, NZ), 6, 247-252.

Lei et al. (2016). Biofunctionalization of silicone rubber with microgroove-patterned surface and carbon-ion implantation to enhance biocompatibility and reduce capsule formation. International journal of nanomedicine, 11, 5563-5572.

Lepaw, M. I. (1979). Complications of implantation of synthetic fibers into scalps for "hair" replacement: experience with fourteen cases. The Journal of dermatologic surgery and oncology, 5(3), 201-204.

Lepaw, M. I. (1980). Therapy and histopathology of complications from synthetic fiber implants for hair replacement: A presentation of one hundred cases. Journal of the American Academy of Dermatology, 3(2), 195-204.

Mapes, D. (2008). The fallout of hair loss: Suffering in silence. Skin and beauty. NBC News. Retrieved on Aug. 4, 2017 from http://www.nbcnews.com/id/26895411/ns/health-skin_and_beauty/t/fallout-hair-loss-suffering-silence/#. WaWCdMmYbF5.

Medlineplus (2017). Hair loss. Health Topics. MedlinePlus. Retrieved on Aug. 4, 2017 from https://medlineplus.gov/hairloss.html.

Medlineplus (2017). Hair loss. Medical Encyclopedia. MedlinePlus. Retrieved on Aug. 4, 2017 from https://medlineplus.gov/ency/article/003246.htm.

English abstract of DE2912043A1.

English abstract of WO8909575A1.

Medlineplus (2017). Pilonidal sinus disease. Medical Encyclopedia. MedlinePlus. Retrieved on Aug. 4, 2017 from https://medlineplus.gov/ency/article/003253.htm.

Mirmirani et al. (2014). Traction Alopecia. Dermatologic clinics, 32(2), 153-161.

Moore et al. (2015). Molecular characterization of macrophage-biomaterial. Adv Exp Med Biol. 865: 109-122.

Motofei et al. (2017). Safety Profile of Finasteride: Distribution of Adverse Effects According to Structural and Informational Dichotomies of the Mind/Brain. Clinical Drug Investigation, 37(6), 511-517.

Murphy et al. (2010). The effect of mean pore size on cell attachment, proliferation and migration in collagen-glycosaminoglycan scaffolds for bone tissue engineering. Biomaterials, 31(3), 461-466.

Mysore, V. (2010). Controversy: Synthetic hairs and their role in hair restoration?. International journal of trichology, 2(1), 42-44.

(56) References Cited

OTHER PUBLICATIONS

Nayyer et al. (2016). A biodesigned nanocomposite biomaterial for auricular cartilage reconstruction. Advanced healthcare materials, 5(10), 1203-1212.
Nido Ltd (2006). What's new. Retrieved on Aug. 4, 2017 from http://www.nidohq.co.jp/nido_english/what/what.html.
Niechajev, I. (2012). Facial reconstruction using porous high-density polyethylene (medpor): long-term results. Aesthetic plastic surgery, 36(4), 917-927.
Oh et al. (2016). A guide to studying human hair follicle cycling in vivo. Journal of Investigative Dermatology, 136(1), 34-44.
Otberg et al. (2004). Variations of hair follicle size and distribution in different body sites. Journal of Investigative Dermatology, 122(1), 14-19.
Pae et al. (1975). Design and evaluation of a percutaneous transthoracic cannula. Transactions—American Society for Artificial Internal Organs, 22, 135-148.
Palmieri et al. (2000). Evaluation of polyamide synthetic hair. A long-term clinical study. Panminerva medica, 42(1), 49-53.
Patel et al. (2016). Solid implants in facial plastic surgery: potential complications and how to prevent them. Facial Plastic Surgery, 32(05), 520-531.
Peluso et al. (1992). Cutaneous complications of artificial hair implantation: a pathological study. Dermatology, 184(2), 129-132.
Perry et al. (2002). Defining pseudofolliculitis barbae in 2001: a review of the literature and current trends. Journal of the American Academy of Dermatology, 46(2), S113-S119.
Poswal et al. (2011). When FUE goes wrong!. Indian journal of dermatology, 56(5), 517-519.
Raposio et al. (2015). Scalp surgery: quantitative analysis of follicular unit growth. Plastic and Reconstructive Surgery Global Open, 3(10): 1-4.
Rose, P. T. (2015). Hair restoration surgery: challenges and solutions. Clinical, cosmetic and investigational dermatology, 8, 361-370.
Rutala et al. (2008). Guideline for disinfection and sterilization in healthcare facilities, 2008. Department of Health and Human Services. Centers for Disease Control and Prevention, pp. 1-161.
Santiago et al. (2007). Artificial hair fiber restoration in the treatment of scalp scars. Dermatologic surgery, 33(1), 35-44.
Scharschmidt et al. (2013). What lives on our skin: ecology, genomics and therapeutic opportunities of the skin microbiome. Drug Discovery Today: Disease Mechanisms, 10(3), e83-e89.
Schneeberger et al. (2004). The tight junction: a multifunctional complex. American Journal of Physiology—Cell Physiology, 286(6), C1213-C1228.
Sengul et al. (2009). Axillary pilonidal sinus: A case report. North American journal of medical sciences, 1(6), 316-318.
Serdev et al. (2015). Polyamide hair implant (biofibre®): evaluation of efficacy and safety in a group of 133 patients. Journal of Biological Regulators & Homeostatic Agents, 29(1), 107-113.
Shao et al. (2014). Follicular unit transplantation for the treatment of secondary cicatricial alopecia. Plastic Surgery, 22(4), 249-253.
Shiell et al. (1990). Problems associated with synthetic fibre implants for hair replacement ("NIDO" process). The Medical journal of Australia, 152(10), 560.
Sinclair et al. (2015). Androgenetic alopecia: new insights into the pathogenesis and mechanism of hair loss. F1000Research, 4(F1000 Faculty Rev): 585: 1-9.
Sluysmans et al. (2017) The role of apical cell-cell junctions and associated cytoskeleton in mechanotransduction. Biology of the Cell (109): 139-161.
Tang, V. W. (2006). Proteomic and bioinformatic analysis of epithelial tight junction reveals an unexpected cluster of synaptic molecules. Biology direct, 1(1), 37: 1-30.
Tchernev et al. (2016). Biofibre hair implant: what is new, what is true?. Journal of biological regulators and homeostatic agents, 30(2 Suppl 2), 49-56.
Figure 1 of Teumer et al. (May 2005). Follicular cell implantation: an emerging cell therapy for hair loss. In Seminars in Plastic Surgery (vol. 19, No. 02, pp. 193-200).
Thiedke, C. C. (2003). Alopecia in women. American family physician, 67(5), 1007-1014.
Toyoshima et al. (2012). Fully functional hair follicle regeneration through the rearrangement of stem cells and their niches. Nature communications, 3, 784: 1-12.
Uebel, C. O. (2005). The punctiform technique in hair transplantation. Seminars in Plastic Surgery, vol. 19, No. 02, pp. 109-127.
Underwood et al. (2011). Quantifying the effect of pore size and surface treatment on epidermal incorporation into percutaneously implanted sphere-templated porous biomaterials in mice. Journal of Biomedical Materials Research Part A, 98(4), 499-508.
Unknown. (2017). Image of hair root. Trends in Molecular Medicine. Retrieved on Aug. 24, 2017 from http://www.cell.com/cms/attachment/553998/3951952/gr1.jpg.
Unknown. (2015). Image of Hair transplant surgery scars in donor area with follicular unit extraction technique. Retrieved on Aug. 25, 2017 from http://ae154zl15g.previewdomain.jp/wp-content/uploads/2015/11/003_BK2.jpg.
Unknown. (2013). Image of Galea aponeurotica seen though scalp incision. Retrieved on Aug. 24, 2017 from http://www.the-dermatologist.com/sites/default/files/issues/Screen%20Shot%202013-08-20%20at%209.00.40%20AM.png.
Unknown (2015). Galea aponeurotica diagram. Retrieved on Aug. 25, 2017 from http://www.learnneurosurgery.com/uploads/1/6/6/8/16689668/1813531.jpg?702.
Unknown (2015). Galea aponeurotica diagram with head in view. Retrieved on Aug. 24, 2017 from http://www.buism.com/hairloss_files/image001.jpg.
Vanhoestenberghe et al. (2013). Corrosion of silicon integrated circuits and lifetime predictions in implantable electronic devices. Journal of neural engineering, 10(3), 031002: 1-13.
Wai, S. (2014). What is hair implant?. Skin health: the creation of beauty is art. Retrieved on Aug. 24, 2017 from http://skinhealthsubang.blogspot.com/2014/08/what-is-hair-implant.html.
Abstract of Wan et al. (2017). Solvent Bonding for Fabrication of PMMA and COP Microfluidic Devices. JoVE (Journal of Visualized Experiments), (119), e55175-e55175.
Wikipedia (2017). Injection molding of liquid silicone rubber. Wikipedia, the free encyclopedia. Retrieved on Aug. 24, 2017 from https://en.wikipedia.org/w/index.php?title=Injection_molding_of_liquid_silicone_rubber&oldid=787919147.
Wikipedia (2017). Injection moulding. Wikipedia, the free encyclopedia. Retrieved on Aug. 7, 2017 from https://en.wikipedia.org/w/index.php?title=Injection_moulding&oldid=794136890.
Wikipedia (2017). Silicone rubber. Wikipedia, the free encyclopedia. Retrieved on Aug. 7, 2017 from https://en.wikipedia.org/w/index.php?title=Silicone_rubber&oldid=788264103.
Wilt et al. (2008). 5-alpha-reductase inhibitors for prostate cancer prevention (review). Cochrane Database of Systematic Reviews, Issue 2: 1-61.
International Search Report for related PCT Application No. PCT/US2019/038950 dated Sep. 13, 2019.
International Search Report for related PCT Application No. PCT/US2020/020389 dated Apr. 21, 2020.
Office Action for related Colombia Patent Application No. NC2020/0002241 dated Apr. 29, 2022.
Supplemental European Search Report for related European Patent Application No. 20767418.5 dated Apr. 8, 2022.
English translation of KR101503014B1.

* cited by examiner

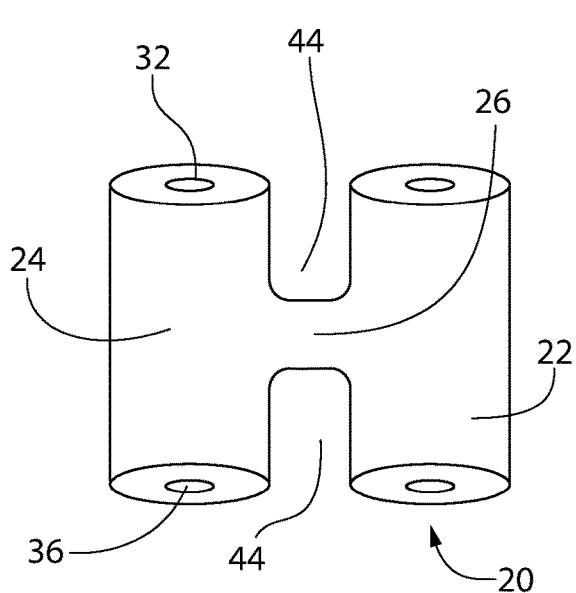 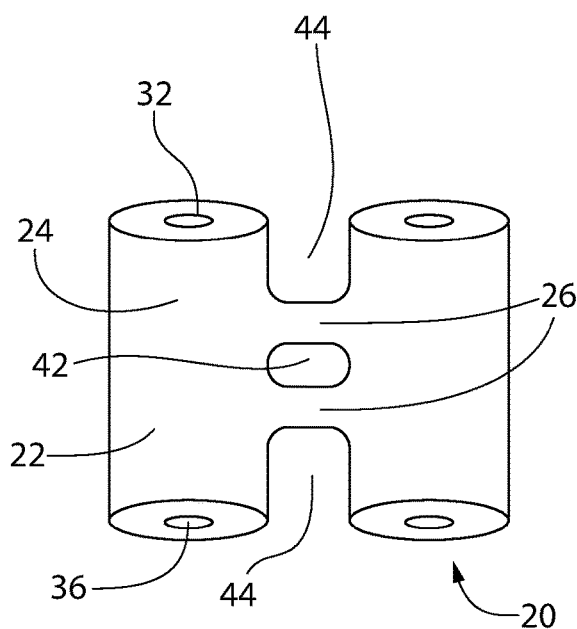
FIG. 4A          FIG. 4B
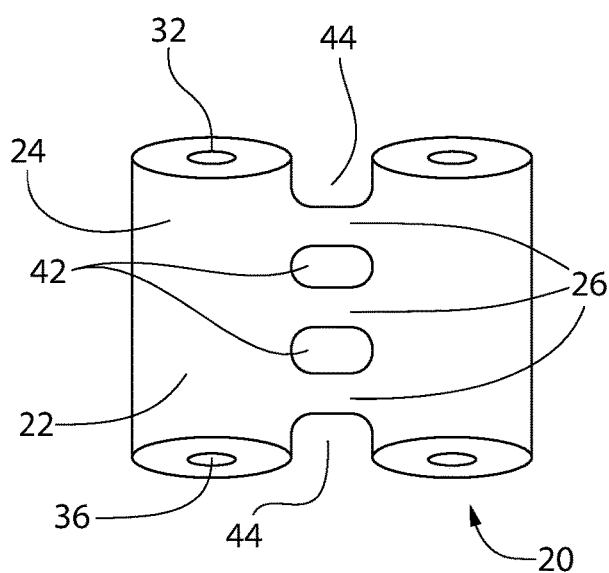
FIG. 4C

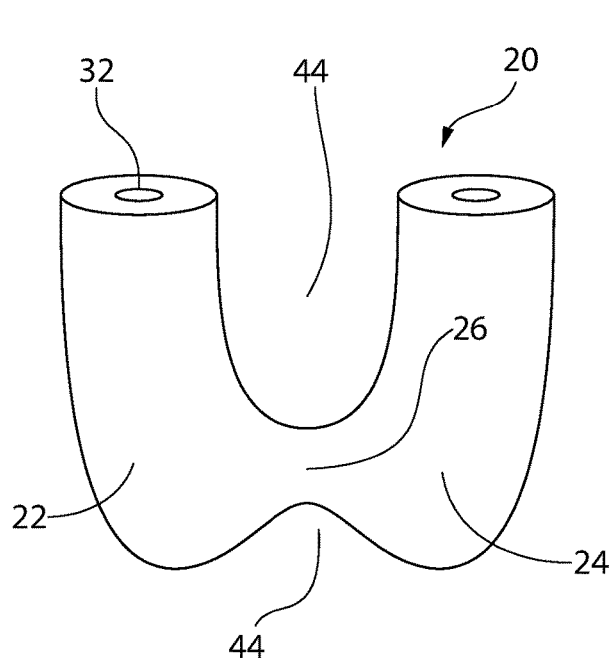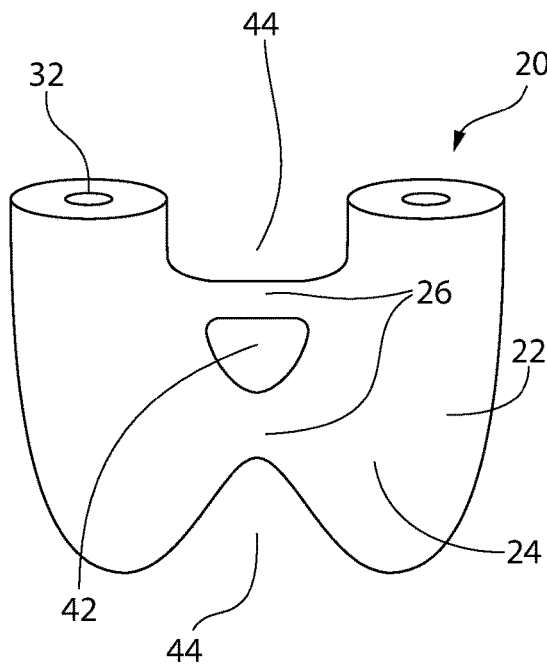
FIG. 5A     FIG. 5B
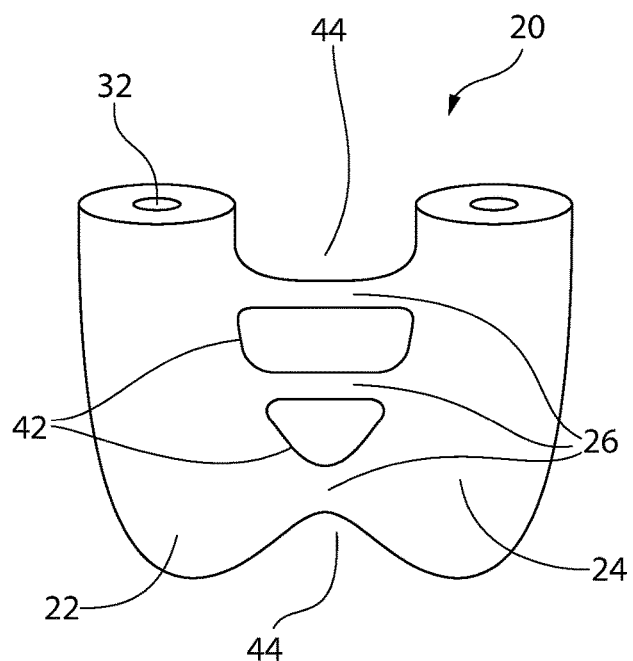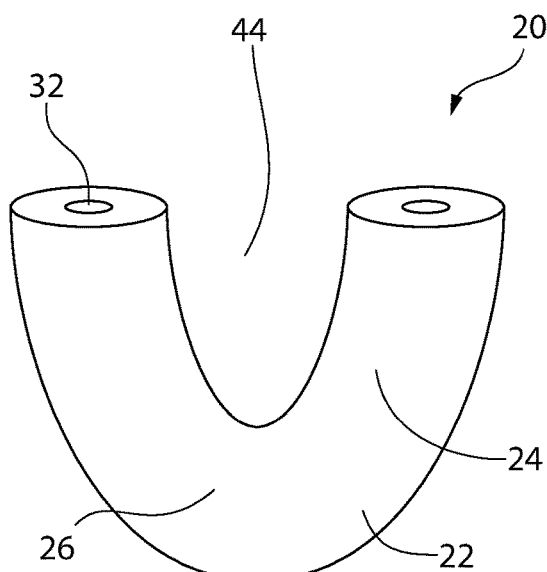
FIG. 5C     FIG. 5D

| | |
|---|---|
| 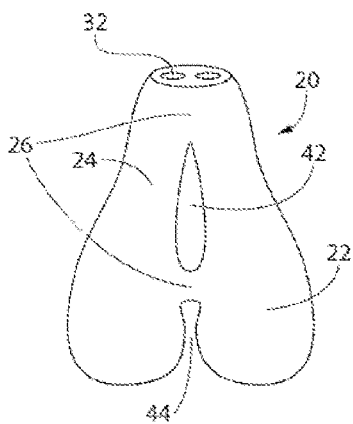 | Present Invention<br>• Tunnel disposed in between first hair chamber and second hair chamber.<br>• A portion of the hair strand is encased within the respective hair chamber to the side of the tunnel, and away from the mid-line of the anchor. |
| 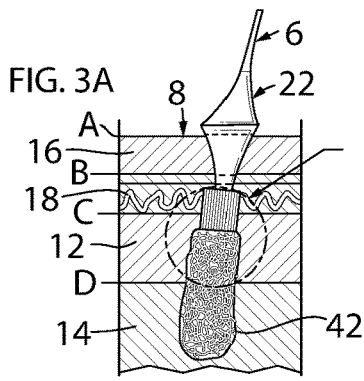 | Erb Prior Art<br>• Reticulated polymer material surrounding hair filament.<br>• Erb teaches the positioning of the hair shaft directly in the middle of the anchor.<br>• As such, Erb teaches away from the present invention. |
| 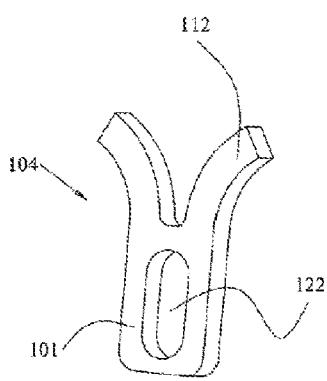 | Keren Prior Art<br>• Two open leaves disposed above non-encasing hair slit.<br>• Keren teaches the positioning of the hair shaft directly in the middle of the anchor.<br>• As such, Keren teaches away from the present invention. |
| 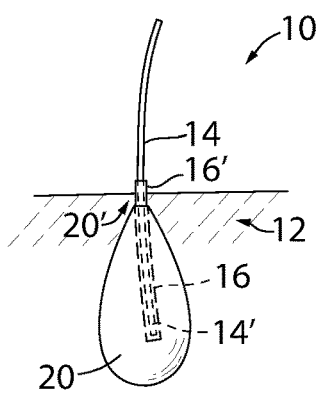 | Laghi Prior Art<br>• Silicone follicle encapsulating end of hair shaft.<br>• Laghi teaches the positioning of the hair shaft directly in the middle of the anchor.<br>• As such, Laghi teaches away from the present invention. |

FIG. 14

HAIR IMPLANTS COMPRISING ENHANCED ANCHORING AND MEDICAL SAFETY FEATURES

CROSS-REFERENCE TO RELATED APPLICATIONS

This application claims the benefit under 35 U.S.C. § 120 of application Ser. No. 15/665,369, filed on Jul. 31, 2017 (now U.S. Pat. No. 9,993,334), and also claims the benefit under 35 U.S.C. § 120 of application Ser. No. 15/718,637 filed on Sep. 28, 2017, both of which are entitled HAIR IMPLANTS COMPRISING ENHANCED ANCHORING AND MEDICAL SAFETY FEATURES and all of whose entire disclosures are incorporated by reference herein. Application Ser. No. 15/718,637 is also a continuation-in-part application and claims the benefit under 35 U.S.C. § 120 of application Ser. No. 15/665,369.

BACKGROUND OF THE INVENTION

1. Field of Invention

This invention relates to the field of hair replacement and more particularly to artificial hair implantation and implants.

2. Description of Related Art

For millennia men and women have been concerned, ridiculed, and even suicidal regarding hair loss and the physical and cosmetic impact it makes upon ones' appearance, especially the loss of scalp or facial hair (2-6). Causes of hair loss are numerous including genetic disorders, genetic inheritance, stress from illness, fever, or physical activity, chemotherapy, pulling on hair, curling irons, chemical processing of hair for shaping or coloring etc., aging, poor diet, thyroid disease, ringworm, and many other skin and non-skin diseases too lengthy to list here (1,7,52,90,91, 114). Treatment for hair loss, including medical and non-medical remedies, have, in most cases, yielded poor to fair results (9-14,51,53,59,92,93).

Treating hair loss with the current available options falls short of meeting the vast majority of patient expectations, regardless of whether the treatment is surgical, medical, or non-medical. Other factors, indirectly associated with not only hair loss, but how the hair loss treatments look as well, have a far greater impact on one's mental and physical health. These factors include the psychological, social, and emotional trauma resulting from how one looks and feels after losing hair and the inadequate solutions available. The extent of psychological, social, and emotional trauma does not end there. Long term anxiety and stress can affect one's physical wellbeing as well (2-6).

A hair restoration treatment that meets most if not all of the patient's key expectations such as the hair looking and feeling natural, providing good hair density, having a low risk of complications, being affordable, and having very low maintenance, would not only be in great demand but would also reduce the stress, anxiety, social, and physical impacts on one's life. In addition, a more natural looking hair loss solution would engender a very happy, confident, positive attitude and sense of wellbeing, which, if it can be calculated, would eliminate many financial, social, and emotions burdens carried by those who are afflicted (2-6).

A variety of hair replacement techniques and methods currently exists, such as hair pieces and toupees, hair weaves and extensions, hair implants, hair transplant surgery, and certain medical treatments that claim to grow hair such as minoxidil, finasteride, and the like. All these remedies provide limited success in one aspect or another, and these limitations not only prevent optimization of expectations but result in emotional setbacks.

Hair pieces, hair weaves, and hair extensions often do not look and feel so natural, resulting in not only ridicule but also a self-conscious sense or real awareness of how unnatural the hair system may look. In addition, these hair pieces or weaves may cause chronic skin irritation resulting in damage and permanent loss of the remaining natural healthy hair.

Hair transplant surgery, another remedy to hair loss (51, 53), is not only very expensive, but is a very invasive surgical procedure having numerous medical risks including infection and scarring of the scalp, hair growth failure, and an unnatural look (26-30,51,54,55,57,104,108,109,113, 114). Even if the hair transplant surgery is deemed a success with no scarring, infection, or hair growth failure, the results, in most cases, will still yield a very thin low density appearance (due to limitations of skin healing capacity), an unnatural appearance at the hairline area due to skin pitting (as a result of recipient site surgical skin trauma), and inappropriate diameter of hair fibers placed (should be fine very thin caliber hair fibers placed into the hairline for a natural transition—which are difficult to harvest) all of which results in an unnatural look.

Medical therapy of the underlying illness causing hair loss may treat the condition but typically does not result in the recovery of hair due to hair follicular organ trauma and death, and thus patients seek a hair restoration solution (1,7). There are some medical conditions that have no medical, non-medical, or surgical treatments such as certain types of alopecia (9).

Medical pharmacological therapy can prevent or stimulate hair growth directly, such as finasteride and minoxidil (10-14,59). These medications not only perform poorly regarding hair regrowth, but are also not benign treatments having no risks or side effects. Finasteride, for example, can not only cause a loss in libido but it can increase the risk of developing a more aggressive type of prostate cancer. Minoxidil, a topical medication, is problematic because it can grow hair in other parts of the body such as the face arms legs and chest, and this is a side effect that many men and especially women find disturbing. In addition, minoxidil can lower your blood pressure and cause to you faint or pass out.

Artificial hair implantation, another type of hair restoration method, is currently illegal in the United States but legal in Europe and other countries (15). Hair implants are associated with many risk factors such as pain, scarring, scalp infections, chronic inflammation, and deep scalp abscess and granuloma formation. There are numerous medical articles recommending not to perform hair implants due to these complications (16-19,60,103).

Hair implants are currently illegal in the United States and the FDA ruling on this matter has now been in force for many decades (15). Even though some isolated reports claim some success with artificial implants (21, 61-65, 87, 116, 117), the FDA banned the use of this artificial hair implant method due to the many patient complaints and complications such as infection, scarring, chronic inflammation, and other problems (15-19, 60). Even though illegal in the United States, it appears that artificial hair implantation is legal in many areas of the world including Asia and Europe. Currently there are two companies that have been manufacturing artificial hairs for implantation, Nido (Japan) (20), and Biofibre (Italy) (21), and have been selling and marketing these artificial hair implants for decades.

An example of a hair implant is taught in U.S. Pat. No. 5,061,284 of Laghi (117), in which a hair plug consists basically in a human hair on which an artificial follicle is formed. Also, U.S. Pat. No. 3,596,292 of Erb (116) teaches a hair implant structure having an anchoring portion extending below the surface of the skin and into the subcutaneous tissue, comprising tissue-pervious structures in the form of microvelours, microporous polymers, reticulated foam polymers or hydrated hydrogels (See FIG. 14)

A further example a hair implant is disclosed in U.S. Pat. No. 9,492,196 of Keren (87), which teaches an anchor formed with a rough surface and a slit or opening through which hair is inserted so that the bulbous root end is implanted into the target tissue. The opening of the slit is sized to restrain the bulbous end of the hair from passing through.

The three most prominent complications resulting from commercially available hair implant products are infection, inflammation, and scarring. The reason as to why these complications occur are related to the type of materials used, the specific design of the materials, and how (the surgical technique) they are anchored to the skin. If the materials, design, and techniques were improved, risks and complications would decrease dramatically making artificial hair implantation an acceptable alternative hair restoration solution for the hundreds of thousands of patients who suffer from hair loss worldwide.

The materials used in the current manufacturing of artificial hair implants involve primarily natural or artificial hair. Hair, whether natural or artificial, is a very antigenic reactive substance when confronted or seen by the immune system (22, 23). Considering the hyper-reactivity and immune response to the materials currently being used, there appears to be little to no medical consideration regarding material selection and how to minimize this negative interaction with the body. When this hair implant is placed deep into the scalp, a lengthy portion of the hair is directly in contact and totally unshielded from the blood or immune system. This deep placement and direct contact of the hair with the body will dramatically increase the potential to invoke an intense and chronic inflammatory response, which is the source of chronic inflammation, pain, infection, granuloma formation, and other serious issues.

The current hair implant design is rather rudimentary, once again, reflecting no medical consideration for natural anatomy, physiology, immunology nor the microbiological factors involved. This design promotes inflammatory interactions with the body and does not provide an appropriate barrier for microbiological (bacterial) protection. In addition, there is no hair implant design element even attempting to stop foreign invaders (bacteria) from entering the body which, by having no barrier as part of the hair implant design, can cause serious acute and long term chronic infections.

The current hair implant technique involves placement of the artificial hair deep into and under the skin. This deep placement involves tunneling the artificial hair under the skin and then attaching it to the deep fascia that lies just above the skull, called the Galea Aponeurotica. Looping and mounting the artificial hair into the Galea is the anchoring mechanism which secures the hair from falling out. Even though this is a very secure mounting technique, it does not allow for, once again, medical consideration regarding adverse immune system interactions or an appropriate bacterial barrier preventing infection, and thus inflammation and infectious complications will follow. Keep in mind that this technique, with very deep and specific placement into fascia type tissue, is limited to the scalp area and does not allow for hair placement in any other part of the body. In addition, there are major problems inherent to this type of mounting technique which involve a high risk of chronic inflammation, abscess formation, severe scarring and granuloma formation, etc. These complications can occur because the implanted artificial (or natural) hair is not shielded, or is in direct contact with the immune system, nor is there a barrier mechanism to prevent bacterial from entering into the body. In addition, the implanted hair fiber may fracture or fragment leaving portions of highly antigenic hair pieces deep in and under the skin resulting in acute and chronic inflammation, potential cyst and granuloma formation, chronic pain and scarring.

Accordingly, it is desired to provide improved artificial hair implants and hair restoration methods using same. It is further desired to provide artificial hair implants, which provide a natural appearance, are configured for secure implantation in the skin, do not elicit an antigenic or inflammatory response, and can be implanted in a variety of densities and patterns.

All references cited herein are incorporated herein by reference in their entireties.

SUMMARY OF THE INVENTION

A first aspect of the invention is a hair implant, comprising: at least two strands comprising at least one of mammalian hair and synthetic hair; and an anchor, which: (a) comprises silicone, (b) is configured for subcutaneous implantation, (c) comprises a fracture line configured to facilitate fracturing of the anchor along the fracture line for ease of removal of the implant after subcutaneous implantation, and (d) is configured to provide a scaffold for collagen growth after subcutaneous implantation, wherein at least one of the at least two strands is joined to the anchor on one side of the fracture line and at least one of the at least two strands is joined to the anchor on an opposite side of the fracture line such that each fragment formed by fracturing the implant comprises at least one of the at least two strands.

In certain embodiments, the at least two strands are synthetic hairs comprising a filament of a polymer selected from the group consisting of polypropylene, polyvinyl chloride, polyamide, polyethylene, polyacrylonitrile, polyvinylidene chloride, polyurethane, polyester and copolymers thereof.

In certain embodiments, the at least two strands have a diameter from 0.01 to 3 mm, or from 0.02 to 0.2 mm.

In certain embodiments, the at least two stands have a length from 1 mm to 500 cm or from 1 cm to 50 cm.

In certain embodiments, the anchor has a largest dimension of 0.1 mm to 2.5 mm or 0.1 to 5 mm.

In certain embodiments, the anchor has a diameter that decreases from a proximal end to a distal end thereof.

In certain embodiments, the anchor has a diameter that increases from a proximal end to a distal end thereof.

In certain embodiments, the anchor has a diameter that is substantially constant from a proximal end to a distal end thereof.

In certain embodiments, the anchor has a mid-section concavity that is roughly equidistant from a proximal end to a distal end of the hair implant.

In certain embodiments, the anchor has an open tunnel on at least one of the distal end and the proximal end of the anchor.

In certain embodiments, the anchor has at least one open tunnel, at least one closed tunnel and at least one bridge between two vertical components.

In certain embodiments, the anchor has an undulation on a distal lateral side thereof, said undulation being effective to inhibit bacterial infection.

In certain embodiments, the anchor has at least one tunnel configured to receive and retain collagen ligatures so as to bind the anchor to the hair implant recipient.

In certain embodiments, the anchor consists of silicone.

In certain embodiments, the anchor is free of hinged leaves.

In certain embodiments, the hair implant is free of metal components.

A second aspect of the invention is a hair restoration method comprising: inserting a needle into the skin to form an incision; inserting an implant of the invention in the incision such that 0.1-2 mm of a silicone coating on a proximal end of each of the at least two strands remains: (a) outside the skin, (b) above the epidermis, (c) under the skin, or (d) below the epidermis; and applying an adhesive to the incision.

In certain embodiments of the method, the incision is made to a depth of 2-8 mm.

In certain embodiments of the method, the adhesive is cyanoacrylate.

In certain embodiments of the method, collagen infiltrates tunnels of the anchor to form ligatures binding the implant.

In certain embodiments of the method, the implant is inserted in the incision such that 0.1-2 mm of the silicone coating on the proximal end of each of the at least two strands remains outside the skin or above the epidermis.

In certain embodiments of the method, the implant is inserted in the incision such that 0.1-2 mm of the silicone coating on the proximal end of each of the at least two strands remains under the skin or below the epidermis.

A third aspect of the invention is a method for manufacturing the implant of the invention, said method comprising: providing a mold comprising at least one cavity for forming the anchor; filling the at least one cavity with a silicone liquid; coating 2-10 mm of a proximal end of the at least one strand with a silicone coating; submersing in the silicone liquid the proximal end of the at least one strand to a depth such that 0.1-2 mm of the silicone coating remains outside of the silicone liquid in the cavity; curing the silicone liquid to provide a solid product; removing the solid product from the mold; and sterilizing the solid product so as to provide the implant.

A fourth aspect of the invention is a hair implant, comprising: at least one strand comprising at least one of mammalian hair and synthetic hair; and an anchor, which: (a) comprises silicone, (b) is configured for subcutaneous implantation, (c) comprises a fracture line configured to facilitate fracturing of the anchor along the fracture line for ease of removal of the implant after subcutaneous implantation, and (d) is configured to provide a scaffold for collagen growth after subcutaneous implantation, wherein the at least one strand is in an internal hair chamber leading from a first distal orifice to a second distal orifice such that each end of the at least one strand remains outside the anchor.

A fifth aspect of the invention is a hair implant suitable for subcutaneous implantation, comprising:
a. a hair strand anchor comprising:
i. an anchor body;
ii. a first hair chamber disposed within said anchor body;
iii. a second hair chamber disposed within said anchor body; and
iv. at least one tunnel disposed through said anchor body, said tunnel further disposed in between said first hair chamber and said second hair chamber, where the tunnel is free of a hair; and
b. at least one hair strand having a portion thereof retained in at least one of the hair chambers, wherein said retained portion of hair strand is further encased by said hair chamber;

wherein said tunnel is configured to support collagen ligature growth after subcutaneous implantation of the hair implant, wherein said tunnel is configured to receive and retain collagen ligatures that are capable of anchoring said hair strand anchor to a hair implant recipient.

In certain embodiments of the hair implant, said hair strand is a human hair strand or a synthetic hair strand.

In certain embodiments of the hair implant, said anchor body is constructed from a biocompatible polymer, silicone, silicone polymer, metal, or metal alloy.

In certain embodiments of the hair implant, at least one end of the hair strand projects from a distal end of the anchor body.

In certain embodiments of the hair implant, said first hair chamber is fluidly connected to said second hair chamber to form a U-shaped hair chamber, wherein said hair strand is retained in said U-shaped hair chamber such that both ends of said hair strand project from a distal end of the anchor body.

In certain embodiments, the hair implant comprises at least two hair strands, wherein a proximal end of each hair strand is disposed and encased within one of said hair chambers.

In certain embodiments of the hair implant, the tunnel is an open tunnel disposed through the anchor body at a distal end or a proximal end thereof.

In certain embodiments of the hair implant, the tunnel is a closed tunnel disposed through the anchor body.

In certain embodiments of the hair implant, the anchor body has at least two tunnels disposed therethrough.

In certain embodiments of the hair implant, the at least two tunnels are parallel open tunnels, disposed on opposing ends of the anchor body.

In certain embodiments of the hair implant, the at least two tunnels are parallel closed tunnels disposed through the anchor body.

In certain embodiments of the hair implant, at least one of the tunnels is an open tunnel disposed on a distal end or a proximal end of the anchor body, and at least one of the tunnels is a closed tunnel disposed through the anchor body.

In certain embodiments of the hair implant, the tunnel through the anchor body effectively creates a longitudinal fracture line through said anchor body that intersects the tunnel.

A sixth aspect of the invention is a hair implant suitable for subcutaneous implantation, comprising:
a. a hair strand anchor comprising:
i. a first anchor body;
ii. a second anchor body; and
iii. at least one bridge connecting said first anchor body to said second anchor body so as to bridge at least one void between said anchor bodies, said void being free of hair; and
b. at least one hair strand having a portion thereof retained in at least one of the anchor bodies, wherein said retained portion of hair strand is further encased by said anchor body;

wherein said bridge connecting said anchor bodies is configured to support and retain collagen ligature growth after subcutaneous implantation of the hair implant, wherein said collagen ligatures are configured to anchor said hair strand anchor to a hair implant recipient.

In certain embodiments of the hair implant, said hair strand is a human hair strand or a synthetic hair strand.

In certain embodiments of the hair implant, said hair strand anchor is constructed from a biocompatible polymer, silicone, silicone polymer, metal, or metal alloy.

In certain embodiments of the hair implant, each of said anchor bodies has a hair chamber disposed therein.

In certain embodiments, the hair implant comprises at least two hair strands, wherein a proximal end of each hair strand is disposed and encased within one of said hair chambers.

In certain embodiments of the hair implant, said hair chamber of the first anchor body is fluidly connected to said hair chamber of the first anchor body to form a U-shaped hair chamber, wherein said portion of the hair strand is retained in said U-shaped hair chamber such that both ends of said hair strand project from a distal end of the hair strand anchor.

In certain embodiments of the hair implant, a portion of said U-shaped hair chamber is disposed in said bridge.

A seventh aspect of the invention comprises a method of subcutaneously implanting a hair implant in a hair implant recipient. The method comprises:

a. providing any one of the hair strand anchors described herein;

b. applying an adhesive to a portion of a first hair strand;

c. inserting said portion of the first hair strand into the first hair chamber;

d. applying the adhesive to a portion of a second hair strand;

e. inserting said portion of the second hair strand into the second hair chamber; and f. inserting the hair strand anchor into a subcutaneous tissue of the recipient, thereby invoking a foreign body reaction such that the anchor becomes encapsulated by collagen and collagen ligature growth is disposed through the tunnel of the anchor, thus anchoring said hair strand anchor to the hair implant recipient.

In a first preferred embodiment of a proximal to distal insertion method, the hair will not be glued first but will first be inserted into the proximal orifice of the vertical component hair chamber, then the hair is pushed through until only 6 mm of the proximal end is visible, then glue is added to this 6 mm end, and finally the hair is continued to be pulled through until completely in the hair chamber.

In a second preferred embodiment of a proximal to distal insertion method, the hair will not be glued first but will first be knotted at its proximal end or otherwise treated or handled (e.g., by melting or by augmenting with a bolus of bonding agent, such as glue) to provide a bulbous end smaller than the larger opening of the knot chamber and larger than the smaller opening of the knot chamber, and then fed into the proximal opening of the knot chamber until only about 6 mm of the proximal end of the hair is visible. Glue is then applied to this 6 mm end (which will contain the knots), and then the hair is continued to be fed through the hair chamber until reaches the most distal end of the knot chamber.

In certain embodiments of the hair implant, said at least one void effectively creates a longitudinal fracture line through said hair strand anchor that intersects said bridge.

In certain embodiments, the hair implant further comprises at least a second bridge connecting said first anchor body to said second anchor body, and bridging at least one void between said anchor bodies.

In certain embodiments of the hair implant, said second bridge is parallel to the first bridge.

A eight aspect of the invention is an anchor comprising: (a) a first hair chamber configured to receive at least one hair strand; (b) a second hair chamber configured to receive at least one hair strand; and (c) at least one tunnel disposed through said anchor between the first hair chamber and the second hair chamber, wherein: (i) the anchor is configured for subcutaneous implantation with at least one hair strand fixed in at least one of the first hair chamber and the second hair chamber; (ii) the tunnel is configured to support collagen ligature growth after subcutaneous implantation by receiving and retaining collagen ligatures that are capable of anchoring the anchor to a hair implant recipient.

In certain embodiments of the anchor, at least one tunnel defines a longitudinal fracture line through the anchor that intersects the tunnel, such that the anchor is configured to fracture along the fracture line upon application of sufficient force to facilitate removal of the anchor.

One of the unique and inventive technical features of the present invention is the tunnel, or void, being located interior (e.g., middle) of the anchor between the hair chambers, which allows for the surrounding anchor body around the tunnel to protect the tunnel from fracturing into multiple pieces, unlike the porous mesh of Erb (116). For instance, the porous mesh of Erb has holes that are not surrounded by a substantial anchor body, and the thin walls between the pores would be vulnerable to fragmentation into multiple pieces. Further still, if the tunnel were to fragment, despite the thick surrounding anchor body, the tunnel will fragment in a defined way as to be right down the middle between the two hair chambers.

A ninth aspect of the invention is an anchor comprising (a) a hair strand anchor comprising: (i) an anchor body; (ii) a hair chamber disposed within the anchor body; and (iii) at least one tunnel disposed through the anchor body; and (b) at least one hair strand having a portion thereof retained in and encased by the hair chamber; wherein the at least one tunnel is configured to support collagen ligature growth after subcutaneous implantation of the hair implant, wherein the at least one tunnel is configured to receive and retain collagen ligatures that are capable of anchoring the hair strand anchor to a hair implant recipient.

In certain embodiments of the anchor a single closed tunnel is disposed through the anchor body and adjacent a proximal end thereof; and a single hair chamber is positioned along a central longitudinal axis of the hair implant.

In certain embodiments of the anchor a single open tunnel is disposed through the anchor body at a proximal end thereof; and a plurality of closed tunnels is also disposed through the anchor body.

In certain embodiments of the anchor the plurality of closed tunnels are two parallel closed tunnels.

In certain embodiments of the anchor, the single open tunnel is positioned between the parallel closed tunnels.

A tenth aspect of the invention is a hair implant suitable for subcutaneous implantation, comprising: (a) an anchor comprising: (i) an anchor body; and (ii) at least one collagen receiving structure selected from the group consisting of a tunnel disposed through the anchor body and an external surface feature of the anchor body; and (b) at least one hair strand projecting from a distal end of the anchor body, wherein the at least one collagen receiving structure is configured to support collagen ligature growth after subcutaneous implantation of the hair implant so as to anchor the anchor to a hair implant recipient.

In certain embodiments of the hair implant, the at least one hair strand has a diameter from 0.02 to 0.2 mm.

In certain embodiments of the hair implant, the at least one hair strand has a length from 1 cm to 50 cm.

In certain embodiments of the hair implant, the at least one hair strand is a human hair strand or a synthetic hair strand.

In certain embodiments of the hair implant, the at least one hair strand is a synthetic hair comprising polymer filaments selected from the group consisting of polypropylene, polyvinyl chloride, polyamide, polyethylene, polyacrylonitrile, polyvinylidene chloride, polyurethane, polyester and copolymers thereof.

In certain embodiments of the hair implant, the anchor has a largest dimension of 0.1 2.5 mm.

In certain embodiments of the hair implant, the anchor body comprises a biocompatible polymer, silicone, a silicone polymer, a metal or a metal alloy.

In certain embodiments of the hair implant, the anchor consists of silicone.

In certain embodiments of the hair implant, the anchor is free of hinged leaves.

In certain embodiments of the hair implant, the hair implant is free of metal components.

In certain embodiments of the hair implant, a retained portion of the at least one hair strand is retained in an internal hair chamber of the anchor body.

In certain embodiments of the hair implant, the internal hair chamber leads from a first distal orifice to a second distal orifice such that both ends of the at least one hair strand project from the distal end of the anchor body.

In certain embodiments of the hair implant, a proximal end of the at least one hair strand is disposed and encased within the internal hair chamber, and a distal end of the at least one hair strand projects from the distal end of the anchor body.

In certain embodiments, the hair implant is unitary in structure.

In certain embodiments of the hair implant, the at least one collagen receiving structure comprises at least one tunnel.

In certain embodiments of the hair implant, the at least one tunnel comprises an open tunnel disposed through the anchor body at a distal end or a proximal end thereof.

In certain embodiments of the hair implant, the at least one tunnel comprises a closed tunnel disposed through the anchor body.

In certain embodiments of the hair implant, the anchor body has at least two tunnels disposed therethrough.

In certain embodiments of the hair implant, the at least two tunnels comprise parallel open tunnels disposed on opposing ends of the anchor body.

In certain embodiments of the hair implant, the at least two tunnels comprise parallel closed tunnels disposed through the anchor body.

In certain embodiments of the hair implant, at least one of the tunnels is an open tunnel disposed on a distal end or a proximal end of the anchor body, and at least one of the tunnels is a closed tunnel disposed through the anchor body.

In certain embodiments of the hair implant, the at least one tunnel defines a longitudinal fracture line through the anchor body that intersects the at least one tunnel.

In certain embodiments of the hair implant, the anchor has an undulation on a distal lateral side thereof, said undulation being effective to inhibit bacterial infection.

In certain embodiments of the hair implant, the anchor has a diameter that decreases from a proximal end to a distal end thereof.

In certain embodiments of the hair implant, the anchor has a diameter that increases from a proximal end to a distal end thereof.

In certain embodiments of the hair implant, the anchor has a diameter that is substantially constant from a proximal end to a distal end thereof.

In certain embodiments of the hair implant, the anchor has a mid-section concavity that is roughly equidistant from a proximal end to a distal end of the hair implant.

In certain embodiments of the hair implant: (a) the anchor comprises silicone; (b) the anchor is configured for subcutaneous implantation; (c) the anchor comprises a fracture line configured to facilitate fracturing of the anchor along the fracture line for ease of removal of the implant after subcutaneous implantation; (d) the anchor is configured to provide a scaffold for collagen growth after subcutaneous implantation; (e) the hair implant comprises at least two hair strands; and (f) at least one of the at least two hair strands is joined to the anchor on one side of the fracture line and at least one of the at least two hair strands is joined to the anchor on an opposite side of the fracture line such that each fragment formed by fracturing the implant comprises at least one of the at least two hair strands.

In certain embodiments of the hair implant, the anchor body comprises a first internal hair chamber and a second internal hair chamber, the at least one collagen receiving structure comprises at least one tunnel disposed between the first internal hair chamber and the second internal hair chamber, the at least one tunnel is free of hair, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the at least one collagen receiving structure comprises at least one tunnel, the anchor comprises a first anchor body and a second anchor body connected by at least one bridge that spans the at least one tunnel, the at least one tunnel is free of hair, the first anchor body comprises a first internal hair chamber, the second anchor body comprises a second internal hair chamber, the hair implant comprises a plurality of hair strands, the first internal hair chamber encases a retained portion of at least a first one of the hair strands and the second internal hair chamber encases a retained portion of at least a second one of the hair strands.

In certain embodiments of the hair implant: (a) the at least one collagen receiving structure comprises at least one tunnel; (b) the at least one tunnel is free of hair; and (c) the anchor body comprises a first tapered side, a second tapered side, a first internal hair chamber disposed within the anchor body parallel to the first tapered side and encasing a retained portion of at least one first hair strand, a second internal hair chamber disposed within the anchor body parallel to the second tapered side and encasing a retained portion of at least one second hair strand.

In certain embodiments of the hair implant: (a) the at least one collagen receiving structure comprises at least one tunnel; (b) the at least one tunnel is free of hair; and (c) the anchor body comprises a first vertical side, a second vertical side, a first internal hair chamber disposed within the anchor body parallel to the first vertical side and encasing a retained portion of at least one first hair strand, a second internal hair chamber disposed within the anchor body parallel to the second vertical side and encasing a retained portion of at least one second hair strand.

In certain embodiments of the hair implant, a retained portion of the at least one hair strand is retained in a single internal hair chamber positioned along a central longitudinal axis of the hair implant, and the at least one collage receiving structure comprises two parallel closed tunnels at a distal end of the hair implant.

In certain embodiments of the hair implant, a retained portion of the at least one hair strand is retained in a single internal hair chamber positioned along a central longitudinal axis of the hair implant, and wherein the at least one collage receiving structure comprises one closed tunnel at a distal end of the hair implant.

In certain embodiments of the hair implant, the at least one bridge comprises four parallel bridges which are oval-shaped in cross-section and span three closed tunnels and two open tunnels.

In certain embodiments, the hair implant comprises five parallel closed tunnels disposed through the anchor body along a central longitudinal axis, wherein: (a) the tunnels are flanked by the first internal hair chamber and the second internal hair chamber; (b) the three uppermost tunnels are substantially identical in size; (c) the two lowermost tunnels are larger than the three uppermost tunnels; (d) the lowest tunnel is the largest tunnel; and (e) the anchor has a diameter that decreases from a proximal end to a distal end thereof.

In certain embodiments of the hair implant, the anchor body comprises a first internal hair chamber and a second internal hair chamber, the at least one collagen receiving structure comprises an external surface feature of the anchor body comprising three protrusions on each of two opposite sides of the hair implant, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the anchor body has a cruciform configuration comprising two hair element arms and two anchor arms, a first hair element arm comprises a first internal hair chamber, a second hair element arm comprises a second internal hair chamber, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the anchor body has an inverted Y-shaped configuration comprising one hair element arm and two anchor arms, a first internal hair chamber in the hair element arm, a second internal hair chamber in the hair element arm, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the anchor body comprises a first internal hair chamber and a second internal hair chamber, the at least one collagen receiving structure comprises an external surface feature of the anchor body comprising a plurality of protrusions on a proximal end of the anchor body that curve upward toward the distal end of the anchor body, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the anchor body comprises a first internal hair chamber and a second internal hair chamber, the at least one collagen receiving structure comprises an external surface feature of the anchor body comprising a plurality of cup-shaped protrusions encircling the anchor body with concavities opened toward the distal end of the anchor body, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the anchor body comprises a first internal hair chamber and a second internal hair chamber, the at least one collagen receiving structure comprises an external surface feature of the anchor body comprising a thread helically encircling the anchor body, the hair implant comprises a plurality of hair strands, the first internal hair chamber encases a retained portion of at least a first one of the hair strands and the second internal hair chamber encases a retained portion of at least second one of the hair strands.

In certain embodiments of the hair implant, the anchor body has a cuboid configuration, the anchor body comprises at least four internal hair chambers each of which contains a retained portion of at least one hair therein, the at least one collage receiving structure comprises at least one tunnel running lengthwise between hair chambers and at least one tunnel running widthwise between hair chambers, and the tunnels are free of hair.

In certain embodiments of the hair implant, the anchor body has an ovoid configuration, the anchor body comprises more than two internal hair chambers, the at least one collagen receiving structure comprises at least one tunnel disposed at a proximal end of the anchor body, the at least one tunnel is free of hair, and the hair implant comprises a plurality of hair strands with retained portions thereof being encased in the hair chambers.

In certain embodiments of the hair implant, the at least one collagen receiving structure comprises at least one closed tunnel and at least one open tunnel, which are disposed in parallel through the anchor body along a central longitudinal axis, and wherein 1-5 hair strands are disposed at a distal end of the hair implant.

An eleventh aspect of the invention is a hair restoration method comprising: (1) forming an incision in the skin; (2) inserting an implant of the invention in the incision such that 0.1-2 mm of a silicone coating on a proximal end of each of the at least two hair strands remains: (a) outside the skin, (b) above the epidermis, (c) under the skin, or (d) below the epidermis; and (3) applying an adhesive to the incision.

In certain embodiments of the hair restoration method, the incision is made to a depth of 2-8 mm.

In certain embodiments of the hair restoration method, the adhesive is cyanoacrylate.

In certain embodiments of the hair restoration method, collagen infiltrates tunnels of the anchor to form ligatures binding the implant.

In certain embodiments of the hair restoration method, the implant is inserted in the incision such that 0.1-2 mm of the silicone coating on the proximal end of each of the at least two hair strands remains outside the skin or above the epidermis.

In certain embodiments of the hair restoration method, the implant is inserted in the incision such that 0.1-2 mm of the silicone coating on the proximal end of each of the at least two hair strands remains under the skin or below the epidermis.

BRIEF DESCRIPTION OF SEVERAL VIEWS OF THE DRAWINGS

The invention will be described in conjunction with the following drawings in which like reference numerals designate like elements and wherein:

FIGS. 4A, 4B and 4C show front views of three other embodiments of anchors of the invention;

FIGS. 5A, 5B, 5C and 5D show front views of four other embodiments of anchors of the invention;

FIG. 14 is a table showing a summary of the present invention compared to the prior art;

DETAILED DESCRIPTION OF PREFERRED EMBODIMENTS OF THE INVENTION

Figure 1:
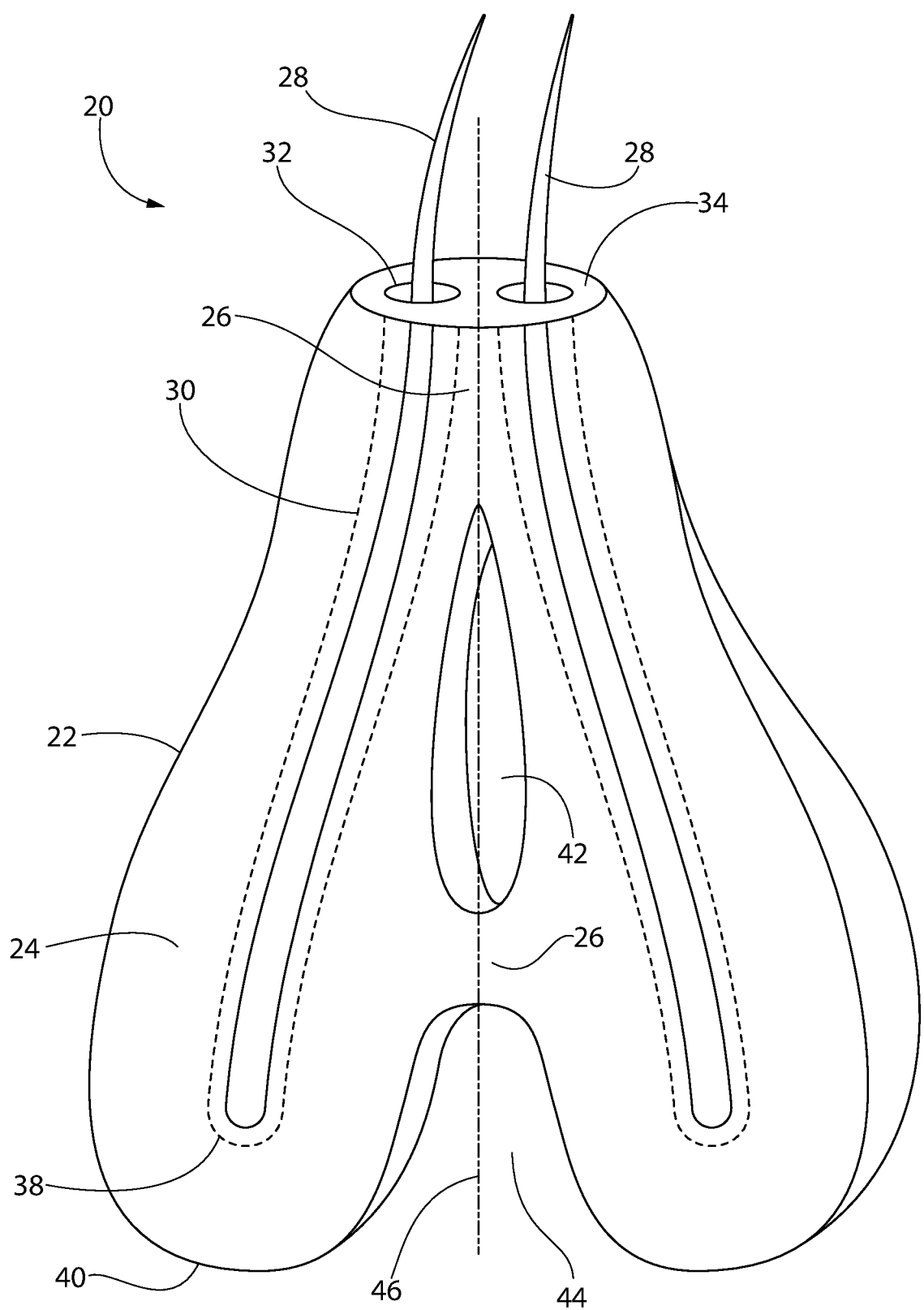
FIG. 1 is a front perspective view of an embodiment of an implant of the invention.

The goal of implanting artificial hair into the body is to achieve a natural appearance with minimal to no side effects. Artificial hair implantation in accordance with the invention achieves this goal by providing a viable and safe patient option for hair loss restoration, which will meet and exceed the expectations of patients not only desiring additional scalp hair but also hair on any part of the body including facial, limb, torso, and pubic areas as well, without the untoward effects from prior and current methods.

Observing the natural form of existing living hair follicles and their anatomy has provided valuable information regarding desirable structural and functional elements of artificial hair implant materials, design, and placement technique.

Natural hair visibly appears exiting from the skin from the deeper dermal layer. This is a very important observation (57,86). If one examines hair weaves, hair extensions, or similar hair systems, the hair exits from above the skin and often looks not only unnatural but does not match the natural hair color or hair density patterns that are found with natural hair growth on the sides and back of the scalp. Upon close inspection of these hair systems, it is possible to see the artificial substrate to which the hair is anchored. In addition, the hair system requires some type of mechanism for anchoring the substrate to the skin, such as tape, glue, or some type of clip. This type of system is like wearing a thick wooly hat which can be uncomfortable at times regarding heat, sweating, and irritation.

Natural anatomic hair density and patterns will vary according to a person's age, sex and genetics. Very natural and thick looking hair can be achieved with hair implantation because unlike hair transplant surgery, there is an unlimited amount of hair available to implant. Mass production of the hair implants is possible, unlike natural living hair follicles. Achieving the appropriate hair density results is also accomplished by utilizing a sleek and narrow implant design which will allow close placement or approximation between each hair implant in addition to having the capability to add emerging hairs (ancillary hair and bud elements described below) to volumize. The hair implant design preferably mimics the general size and shape of the natural hair follicle (88,89). This issue of achieving high hair densities becomes critical for women and young men because, in a far majority of times, they have very full and dense hair patterns showing no signs of hair loss, hair recess patterns, or any balding patterns whatsoever. Any type of hair restoration, whether medical, surgical, non-medical, that yields a low-density look will result in a sub-optimal look for such patients, which results in disappointment and low self-esteem.

Medical treatment, such as minoxidil or finasteride, is not capable of such success. Hair transplant surgery cannot achieve the density goals due to limited "living" hairs to transplant from the donor area, and placing living hair grafts too close together result in trauma and hair follicular death. Even with the best medical and surgical efforts, 80 to 90 follicular units per square centimeter, which is the natural density of scalp hair, cannot be achieved (55). Artificial hair, such as hair pieces, weaves, wigs, etc., can achieve the hair density and pattern, but these systems are just too unnatural looking and are very uncomfortable generating heat, sweat, and, in addition, skin irritation, inflammation and traction alopecia resulting in further natural hair loss (90-93).

Cells in the body, including cells of the skin, have natural attachments to each other. These attachments provide not only communication channels but protect the body from bacteria entering. These attachment mechanisms, also called tight junctions, or desmosomes (33-38), provide for hair follicle anchoring, protection from invading bacteria, and protection from the immune system cells approaching or contacting the hair fiber itself.

The natural flora or microbiological organisms of the skin are numerous. These microorganisms are mostly harmless and provide benefits by immune system communication and cooperation in assisting in the defense of the body. However, these living quarters are limited by the natural physical barriers present in the skin. The structural anchoring and physical barrier mechanisms of the skin, including the hair follicle and its close association to the surrounding skin, glandular elements, and desmosomal cellular junctions between the cells, and the natural collagen layer surrounding the follicles, limit the natural flora of the skin to penetrate the deeper skin layers and blood circulation. (39,40,41). The natural flora will change under certain circumstances such as when hair loss occurs. If there is loss of the hair follicle, and its anatomic structure which penetrates deep into the skin is no longer present, the normal flora will no longer live there. When a hair implant is placed, this follicular anatomy will be re-created and bacteria will, once again, reside in the superficial skin surface area. When the hair implant forms the outer collagen shell, or collagen envelope from the foreign body reaction, a channel (or slight spacing) between the implant and collagen will exist to a certain distance distally, which will mimic the natural follicular anatomy with its natural flora to some degree. With the formation of the collagen envelop, a strong physical barrier will exist to eliminate bacterial entrance into deeper layers of the skin and into the blood or lymphatic circulation. This type of collagenous barrier is the very same barrier found in the normal anatomy and histology of the natural hair follicle (89).

Natural hair fibers are known to be antigenic and very reactive and highly inflammatory when they are exposed to the immune system. A collagen envelope surrounding the natural hair follicle prevents the immune system from "seeing" and attacking or killing the living hair follicle organ (30,42,43,44). When the hair or hair follicle is found out of place, and is outside of the natural envelope, such as when there is ingrown hair for example, the hair encounters the immune system. Ingrown hair invokes a foreign body giant cell reaction (cells involved in the foreign body reaction) whereby the immune system attempts to encapsulate the hair or hair particles with collagen (45,46). This is the very reaction that will be exploited in a positive fashion to direct and form a collagen envelop around the hair implant of the invention.

Figure 12:
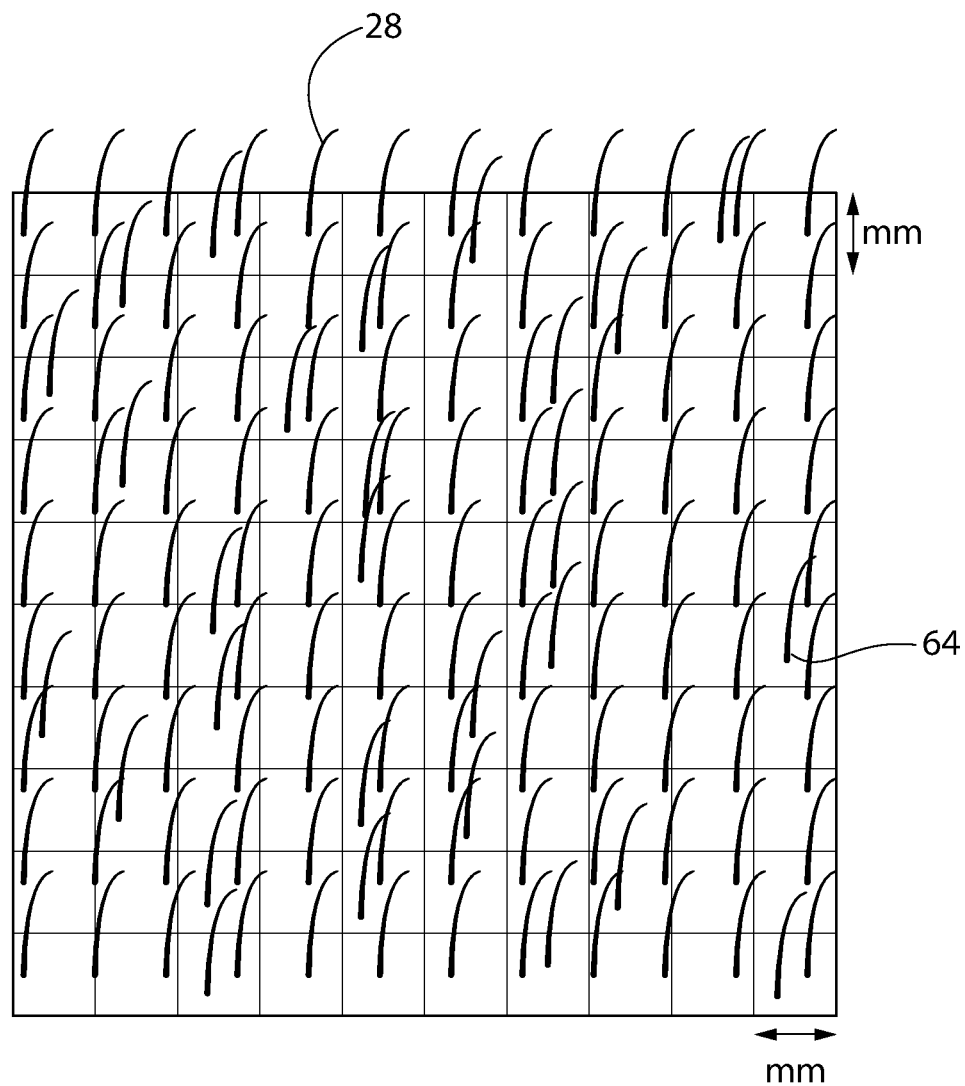
FIG. 12 is a schematic view of a scalp not in need of hair implantation.

There are about 100,000 hairs on the human scalp, and about 5 million on the human body. There are about 120 square inches of hair bearing skin on the scalp. Each square inch, or 6.4 square centimeters, comprises 833 hairs, or about 130 hairs per square centimeter. See FIG. 12.

Hair loss is not perceived or observed until about 50% is lost. The ultimate goal in hair restoration is to achieve the appearance of a full head of hair, which can be achieved by providing only 50% of the normal quantity of hair per unit area. The invention can provide the appearance of a full head of hair or something less for those whose hair restoration goals are more modest.

Assuming total hair loss from the human scalp, replacement of 50% of the original quantity requires the implantation of 65 hairs per square centimeter. The invention preferably enables implantation of up to 65 or up to 100 hairs per square centimeter. In embodiments of the invention comprising emergent hairs, hair density can range up to about 200 hairs per square centimeter. This is greater than the required 65 hairs, but allows for hair loss over time. The extra density will maintain the appearance of a full head of hair for a greater length of time between hair implant sessions.

Figure 13:
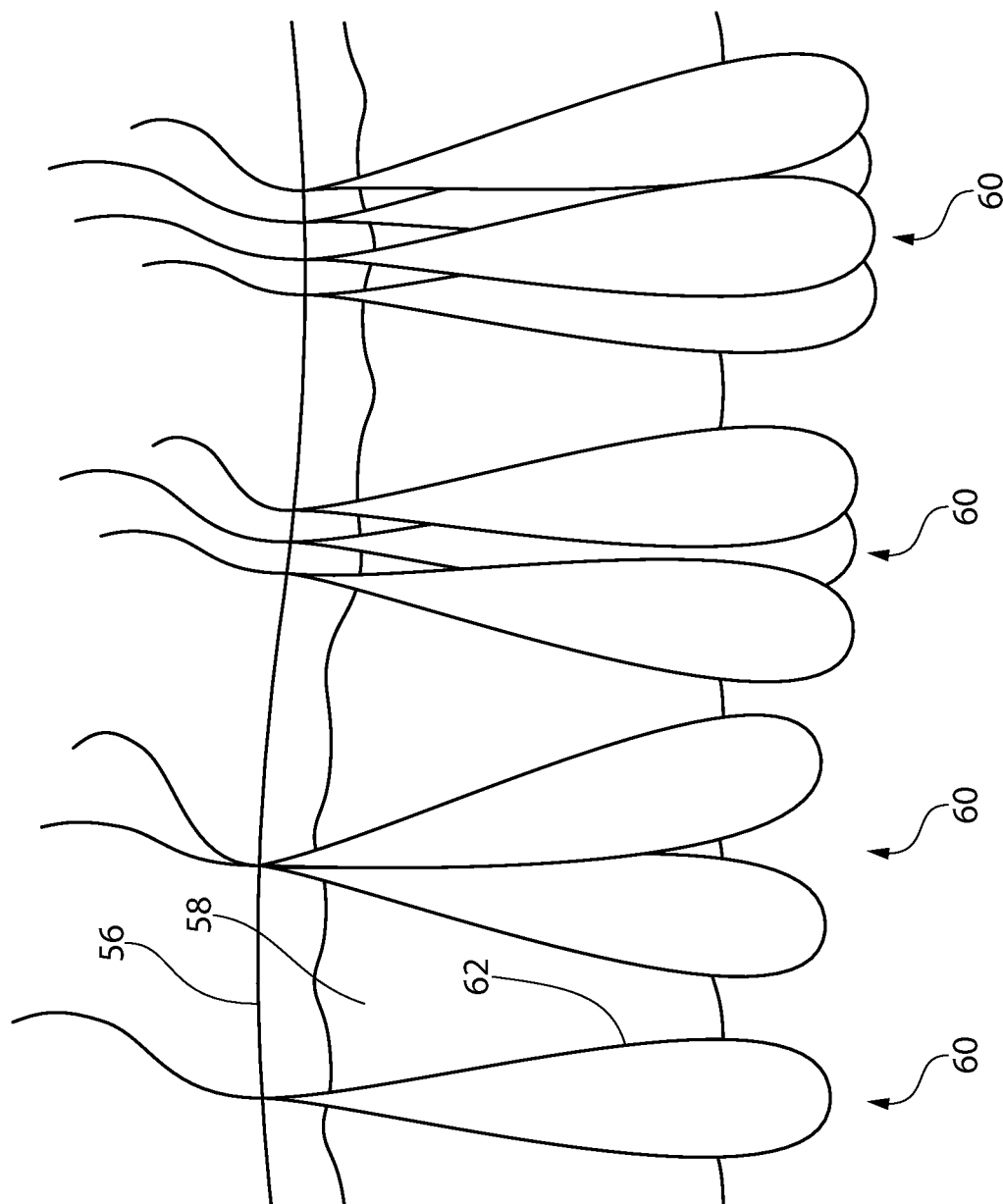
FIG. 13 is a schematic cross-section of skin showing the natural anatomy of hair follicles and follicular units.

Upon examining the scalp, it will be observed that most hair follicles naturally group close together in clusters, and typically are not isolated as single hair follicles. These natural groupings are termed "follicular units" or FUs. As shown in FIG. 13, follicular units 60 typically include 1, 2, 3 or 4 hairs 28. See (52). Hair 28 grows out of follicle 62 within dermis 58 and exits epidermis 56. This aspect of natural anatomy has been taken into consideration in the design and manufacturing of the artificial hair implants.

Hair follicle density and depth into the skin is also observed. Surgical photos demonstrate the depth and density of hair follicles (51,54,55).

In addition to these key anatomic observations of the natural hair follicle, there are other functional elements such as sensory nerves, blood vessels feeding the hair follicle, sebaceous and other glandular elements involved with certain liquid secretions that are associated with the natural living hair follicle. The absence of such functional elements from artificial hair implants does not impede the goals of very natural feeling and looking hair.

Thus, there are several features in the natural anatomic design that can be emulated in the artificial design to meet the patient's goals of achieving a full or near full complement of naturally feeling and looking hair. Artificial implants of the invention preferably provide one or more of the following features: (1) the natural look of hair exiting the scalp, (2) natural hair density and pattern, (3) appropriate anchoring of the hair implant to prevent undesirable fall out, and (4) protecting the artificial hair implant from the immune system and preventing short and long term inflammation.

Hair Implantation: Structure, Function, And New Innovative Considerations

Materials

Introduction

Medical grade silicone rubber and similar materials have been used for cosmetic and medical use for decades as major components of implantable medical devices. These materials have been used in millions of people over the last few decades for facial, breast, and other body enhancements. These implants have been proven safe for permanent implantation into the body. Even though safe, it is recognized that there is the possibility of the need for future replacement of such implants over time. Implant replacement is indicated, for example in the case of long standing, malformed or ruptured silicone breast implants (and other cosmetic implants), when severe contracture, pain, psychological issues, or an aggressive foreign body reaction with collagen encapsulation of the medical device results. (66-70,73-75).

The anchor portion of the implant, with or without any assistance or need of an additional chemical coating to help provide longevity, will be in direct contact with the body and immune system. This material will invoke a foreign body reaction. The foreign body reaction will result in walling off or encapsulating the implant with collagen. This reaction will continue until the entire implant is surrounded with collagen. This enveloping of collagen around the implant is favorable for many reasons. First, the complete collagen envelope around the implant will shield the immune system from the implant itself, which is the goal of the foreign body reaction to any foreign body. Second, the collagen will form a chemical bond directly with the implant material resulting in an attachment or implant stabilizing anchoring feature. Third, the collagen formation, over time, will contract, which will add additional anchoring and stabilization of the implant along concave aspects of the implant. Lastly, and most importantly, this collagen envelope is naturally found in the normal anatomy of the hair follicle, which provides a natural collagen barrier for the highly antigenic hair follicle from the immune system, and thus, will provide the same function for the hair implant.

The foreign body reaction is the body's response to a foreign body invading or entering the body such as a piece of metal, plastic, or foreign substance. The ultimate goal of this reaction is to protect the body by quarantine or encapsulating the foreign substance with collagen, and thereby entombing and subsequently rendering this substance harmless to the body. Once this immune system response has been completed, this encapsulation reaction will cease.

Considering that the immune system's foreign body reaction results in collagen encapsulation, this mechanism can be exploited and used in a special way regarding the hair implant healing and anchoring process. This reaction can assist in producing collagen in a controlled and precise manner. The desired objectives would be to surround and form an envelope of collagen around the hair implant, provide anti-bacterial protection, provide significant anchoring features needed for stability and the success of hair implantation, and protect the implant from further immune system reactions, such as chronic inflammation, etc. The foreign body reaction and the sequence of events will be discussed below.

After placement of the hair implants, the body will see that a foreign substance has been introduced into the body. The hair implant itself, with the silicone tip or anchor will be exposed or in direct contact with the body. This direct contact will initiate the very special biochemical immune system reaction, the foreign body reaction.

This foreign body reaction is typically seen as the end-stage response of the inflammatory and wound healing process following implantation of a medical device or prosthesis. The objective of this special type of reaction is to wall off or quarantine this foreign substance in an effort to protect the body. This reaction, which is quite different from a white blood cell response to a bacterial infection, is composed of very special cells called macrophages and foreign body giant cells. These cells initiate an inflammatory response resulting in collagen formation which will ultimately surround or wall off the foreign body in total if possible, essentially entombing it in collagen and rendering it safe or harmless while remaining in the body. This also results in immune system dormancy.

This resulting envelope of collagen formation around the implant will prevent a chronic inflammatory reaction by completely shielding it from the immune system. This reaction towards the hair implant is desirable.

In addition, the collagen formation will help anchor the hair implant to the skin by a combination of biochemical reactions and physical interactions. The biochemical reaction is the direct attachment of the collagen to the silicone material.

A physical interaction between the newly formed collagen and the hair implant anchor will also occur. Considering that in certain embodiments the shape of the anchor is concave, the collagen will hug or tighten around the anchor preventing the anchor from release from the skin. Another physical feature of the anchor are tunnels. These tunnels will allow the collagen to infiltrate the anchor forming a loop of collagen which will help bind the implant with a living biological ligature. The biological collagen ligatures will be one of the main mechanisms by which the anchor is held in. If the anchor were to fracture along the fracture line, which it is designed to do if excessive erosion or stress is placed on the anchor, the collagen ligatures will release causing instability of the resulting two parts of the anchor. This destabilization permits easy release of the anchor thus prevent fragment retention within the body.

Lastly, the combination of the collagen enveloping and direct physical anchoring effects result in a tightening effect of the collagen around the anchor, which adds an additional protective feature, preventing bacteria from entering in between the anchor and the collagen envelope due to the limited space formed there. Now, with the foreign body (the anchor) entombed in collagen, the body's immune system has accomplished its protective function and will allow the entombed substance to remain within the body, without further acute or chronic inflammatory reactions, for the rest of one's life.

It is critical to note that natural hair follicles have a collagen shell or envelope as well, which is a very important and interesting parallel to not only mention but to emulate. As natural hair fibers are developing embryologically, this protective collagen envelope is seen forming around the hair follicle. This is not by accident but by design because without this outer collagen shell, the body would attack the hair follicle thinking it was a foreign body, and destroy it.

Thus, the foreign body reaction is exploited to serve the many aforementioned hair implant functions and goals such as hair implant anchoring and stability, infection prevention, immune reaction dormancy eliminating chronic inflammatory conditions, and preventing subsequent pain, discomfort and scarring.

Natural Look

Obtaining the natural look of hair exiting the skin at the epidermal level can be accomplished by using natural (or synthetic) hair fiber strands, and implanting these fibers in such a fashion as to emulate the normal hair fiber—epidermal junction anatomy (with no pitting, or unusual anatomic aberrations). The materials needed to accomplish this are the natural looking hair strands, whether natural or synthetic, and, for simplicity of the discussion, silicone rubber to coat the tip of the hair. The hair tip portion that is coated with silicone rubber will be in direct contact or implanted into the skin itself. The key to a natural hair exit look from the scalp or any hair bearing skin areas, is closely associated with the type of incision made (discussed in the implant technique section) and the shape of the silicone implant at the epidermal level (discussed in the design section).

The hair strand(s), whether natural or artificial, can be tailored in color, shape, length, etc., to the anatomic location and cosmetic desires and needs of the patient. For example, hair implants for the scalp can be custom designed to be long, short, straight, curly, black, or blonde, etc. Hair implants can also be customized for the eyebrows, pubic, and other areas of the body. See, e.g., Otberg et al. (58).

In embodiments wherein the hair component, whether natural or synthetic, will be coated with another material and then implanted into the skin, the type of hair used is not critical since the hair is not visible to the body or immune system. Only the coating on the hair will be in direct contact with the skin and subcutaneous tissues or immune system. This optional coating substance, such as medical grade silicone (or other or combination of materials such as an additional outer layer of polycarbonate), will be in direct contact with the skin and immune system and thereby play a role to not only biochemically bind, physically hold, ligature anchor, to stabilize the implant but also to reduce the oxidation reaction in efforts to preserve the integrity of the implant long term from fracture or breakdown.

Materials suitable for the hair component of the inventive implant include but are not limited to human hair, animal hair and synthetic polymers. Non-limiting examples of polymers suitable for synthetic hair include one or more of polypropylene, polyvinyl chloride, polyamide, polyethylene, polyacrylonitrile, polyvinylidene chloride, polyurethane and polyester.

Hair suitable for use in the invention can be straight, tightly curled or loosely curled. Suitable hair can be colored, partially colored or uncolored. The length of the hair fibers is not particularly limited, but suitable hair fibers are preferably at least 5 cm or at least 10 cm or at least 15 cm in length for ease of styling after implantation. Hair materials suitable for use in the invention preferably have a diameter similar to naturally occurring hair, for example, ranging from 0.02 to 0.2 mm. The cross-sectional shape of the hair is preferably elliptical or round, like naturally occurring hair.

Hair Density and Pattern

The anchor preferably has a very narrow design, simulating the actual size of the natural hair follicle, which enables close placement or approximation of the hair implants, yielding a greater density of hairs per unit area. The anchor preferably has significant material strength and durability to withstand pulling forces and oxidation reactions from the immune system.

Anchoring of the Hair Implant

The composition of the anchor of the inventive implant plays a major role in anchoring of the hair implant; however, there are other major factors involved with anchoring such as the shape and internal structure of the implant which will be discussed in the design section. The implant material allows for the stimulation of the foreign body reaction to take place, resulting in a collagen envelope forming directly around the implant. This close association will then result in a biochemical bond between the collagen and the base (i.e., anchor). This bond, whether covalent and/or non-covalent, will provide an anchoring force. Another factor is that the material promotes collagen formation external and internal to the implant. The anchor preferably comprises tunnels (defined herein as voids of varying dimensions that are configured for infiltration by host tissues, which include but are not limited to pores, grooves and channels) so the foreign body reaction and subsequent collagen formation can infiltrate the anchor and act as a ligature to hold the implant in place. The material of the anchor is preferably a stimulant or collagen growth promoter to encourage this to happen.

The hair implantation prior art teaches that the foreign body reaction is detrimental to implantation and is to be avoided. The instant invention proceeds contrary to the prior art by encouraging the foreign body reaction and the resultant formation of a collagen shell or envelope, and collagen ligatures through the tunnels of the inventive implants to anchor them to the scalp or other tissue.

For example, Erb et al. (116) states that the goal is to avoid the foreign body reaction and rejection reactions and Laghi (117) states that the foreign body reaction is destructive. Moreover, Erb et al. teaches tissue growth resulting from a non-foreign body reaction, which is cellular rather than collagenous in nature.

Protecting the Hair Implant from the Immune System

The anchor material assists in protecting the hair implant from immune system attacks and oxidation by invoking a foreign body reaction. The foreign body reaction will allow the body to envelope the hair implant with a collagen wall and thus "shut down" the immune system since the goal and final reaction of the foreign body reaction is the quarantining of the foreign body, which is, in this case, the hair implant itself. In addition, a more durable material will resist oxidation from interaction between the implant material and the body. This oxidative process may come from the immune system or local cells releasing certain chemicals causing this reaction. Lastly, the material preferably allows for a linear fracture (or break) line and eliminates fragmenting. The material preferably allows for limited risk of breaking into small pieces. References teaching other implantation methods, such as Erb et al. (116), Laghi (117) and Keren (87), do not recognize the potential problem of fragmentation, which may result in device fragment retention and chronic inflammation, and do not propose a solution to this very significant issue.

Hair Implant Safety Features

The materials used for implantable medical devices for human use have been studied and have been proven safe and subsequently, have been used for over 50 years now. They have been proven safe, of course, but with limitations. For example breast implants typically last 10 or so years. Even though not permanent, it is acceptable to have them removed and then replaced. In this line of thinking, hair implants may last 10 or more years as well, possibly falling out naturally, or simply being pulled out, etc., however, hair implants can be replaced as well.

Design

Introduction

The design used for the hair implant of the invention involves a certain size, shape, and internal structure to optimize certain objectives such as providing secure anchoring, a bacterial barrier, natural and appropriate hair density and pattern placement, and structural integrity of the implant to prevent oxidation and fracture.

Natural Look of Hair Exiting the Scalp

One key design factor for making hair implants to look as natural as possible is to closely look at how natural hair exits the skin at the epidermal level. The standard or objective in hair implant design is for the hair implant to exit the scalp with the same or similar epidermal-dermal anatomy of existing hair. Natural hair exiting the scalp (with all of its natural anatomic features) is the ultimate goal to parallel.

The natural hair exiting the epidermis has certain anatomic features such as a narrow diameter exit pore and a certain epidermal slope angle and depth. These natural anatomic characteristics can be emulated by applying certain design features to the hair implant device. For example, by designing the distal end of the hair implant with a tubular shape, minimal diameter, and with an appropriate distal to proximal widening slope, the hair implant will allow the epidermal opening diameter and internal sloping to be the same or similar to natural hair. Of course, this epidermal development regarding shaping will occur during the healing process which will involve the foreign body reaction and epidermal migration.

This natural look of hair exiting the skin is a rare characteristic with most if not all hair restoration solutions. Wigs and toupees have the hair exiting from above the skin, not very natural at all. Hair transplant surgery will result in hair exiting from under the skin; however, in most cases, the techniques used typically result in skin damage causing the skin pore to widen and deepen in size, often referred to as a pitting skin look.

Hair Density and Hair Pattern

Design of the anchor will also have an impact on the hair density and pattern and the anchor shape with a general sleek narrow design and crimped-angled proximal hair strand will assist in achieving these goals. The sleek or narrow design, preferably not being wider than 300-2500 microns in any particular area, will allow for a greater placement of hair implants per unit area, with the goal of achieving hair densities found naturally in any hair bearing area. In certain embodiments, the anchor is sized to fit within a cube of 10 mm×10 mm×10 mm.

Hair density and patterns vary among men and women, among the young and old, among race and religions. Natural looking hair, whether the implants are sparsely or closely placed, can achieve the desired hair density and pattern goals for each patient. The high density or "very thick look", for the young and women, can be achieved by this sleek narrow design of the hair implant allowing for close approximation of each hair implant, resulting in a dense natural hair pattern look. Conversely, a less dense pattern can be placed for elderly men, as desired.

Closely associated with hair density is hair pattern. This involves hair placement location and angle of exit. For example, if an elderly man wants to not only have a thinning look but also wants a receding hairline with a very thin crown area, this is easily achieved by the physical placement of the implants to the desired skin areas. The angle of exit is a more important feature on the temporal scalp and eyebrow areas. In these locations, the implant will need to angle more acutely than what is surgically permitted when making the recipient site. For example, when making the recipient site the physician can only insert the needle/cutting device at a certain angle, which is not acute enough. The need for this acute angle is critical because if the eyebrow hair does not grow parallel to the skin, but in an upward and outward fashion, this will look very unnatural. To achieve this acute angulation, the hair component itself will be angled or curled. Inserting such a non-linear hair into the silicone portion of the implant will provide that additional hair exit angulation needed to make the hair look natural.

Anchoring of the Hair Implant

Design, involving the external and internal shape, will be the most significant aspects regarding hair implant anchoring.

The internal structure consists of one or more tunnels. The foreign body reaction will produce collagen along all the surfaces of silicone, including the internal tunnel surfaces. When the collagen forms with the silicone lined tunnels, it will form a natural loop of collagen, much like a natural anchoring stitch or ligature helping to anchor the implant from being pulled out.

The external structure, which is preferably provided with certain concave sections, will provide grip points after the collagen has developed around the implant. When the implant has been surrounded with collagen, and since there are concave and convex portions, more physical force to pull out the hair implant from the skin will be needed because of the added drag placed on the implant by the collagen.

Another factor to consider is the collagen contraction that occurs over time. For example, when silicone breast implants are placed the foreign body reaction results in a collagen shell around the implant. This collagen shell will contract, or exert a force on the breast implants over time. This is not favorable for breast implants because it results in patient discomfort and pain; however, this is favorable regarding the hair implant device. This collagen formation and contracture force will help anchor the hair implant. In addition, this contracture force will provide a more secure tight barrier between the implant and skin/subcutaneous area, which will prevent bacterial migration.

Protecting the Hair Implant from the Immune System

Referring to FIG. 1, anchor 22 of implant 20 comprises two vertical components (or anchor bodies) 24 joined by a bridge 26, with closed tunnel (or void) 42 above the bridge and open tunnel 44 below the bridge. In this embodiment of the invention, which mimics a natural follicular unit having two hairs and two hair follicles, each hair 28 is contained within an internal hair chamber 30, which has a distal orifice 32 and a proximal closure 38 near the proximal end of implant 20. Hair 28 exits distal end 34 of implant 20 through distal orifice 32. In accordance with a preferred embodiment of the invention, at least one hair 28 is on each side of fracture line 46 (discussed in greater detail below), such that there is at least one hair in each of the two fragments resulting from fracturing of implant 20.

Anchor 22 is preferably about 2-8 mm or 3-6 mm in length (i.e., along a longitudinal axis defined by the hair strand(s) within the anchor; top to bottom in the perspective shown in FIG. 1), preferably about 500 microns to 2.5 mm in width (i.e., along an axis transverse to the longitudinal axis; left to right in the perspective shown in FIG. 1) and preferably about 500 microns to 2.5 mm in depth (i.e., toward the viewer and away from the viewer in the perspective shown in FIG. 1). The dimensions of the anchor are preferably modified depending on the location of hair placement.

For example, scalp hairs penetrate the skin to a depth of approximately 6 mm, and eyebrow hairs are generally shorter, about 3-4 mm in length. This depth design not only parallels the natural depth penetration of the natural hair follicle but provides additional favorable safety features. This minimal depth design will allow the body to encapsulate or envelope with collagen and conceal the implant from the immune system, unlike prior art hair implant systems. In addition, after the collagen formation has been completed by the immune system via the foreign body reaction, the interaction between the silicone implant and the immune system will cease. This is not the case with the prior art hair implant technique, which exposes a relatively very long piece of very antigenic hair (whether natural or synthetic) to the immune system by placing the hair deep into the scalp and looping or connecting the hair to the deep fascia of the scalp, the Galea Aponeurotica. This prior art system results in a state of chronic inflammation with further sequalae such as infection, scarring, granuloma formation, and pain. The collagen enveloping of such a long hair implant, with a knot at the end, and the hair traversing multiple planes of tissue, has proven to be difficult regarding compete encapsulation of collagen. Without complete encapsulation of the hair implant with collagen, the foreign body reaction will continue in perpetuity not allowing immune system to shut down or remain dormant.

Hair Implant Safety Features

There are two primary concerns with hair implant safety—infection and inflammation.

Infection is caused by living organisms such as bacteria, fungi, and viruses. Living organisms naturally live on the skin surface and in a symbiotic manner (in most cases). If the anatomy of the skin is altered, such as in a skin cut, these bacteria can now enter within the body and cause an infection. Hair implantation will involve a temporary minor needle puncture, then the hair implant is placed in that puncture, then healing will occur. It is important that healing occurs and that infection and inflammation do not occur.

Hair implants need to be designed to prevent the downward flow of microorganisms from around the hair implant thus preventing an infection from occurring. Prevention of infection is accomplished by the hair implant internal and external shape, foreign body reaction and collagen envelope production, collagen envelope contraction over time, biochemical bonding reaction between the collagen-silicone rubber interface, distal design, and patient hair and scalp cleanliness. Such design features are found in the natural anatomy of the hair follicle such as the collagen envelope, biochemical bonds at the cell interface and tight junctions, and distal narrowing.

The external shape, particularly the narrowing of the distal end, will result in a minimal epidermal opening thus limiting the corridor size and exposure to bacteria at the hair implant skin contact areas. In certain embodiments, there will be a distal initial upward then downward slope angulation of the device, tilted upwards by 30-45 degrees, which will prevent an easy downward flow pathway for bacteria. The epithelial cell growth that will form along the distal end of the implant and join the newly formed collagen envelope, will provide additional cellular contact and proximity to the implant thus limiting bacterial access.

The general anchoring aspects, which involve the external and internal shape of the hair implant, also support the safety element of preventing bacterial entrance by forming a tight approximation between the implant and living tissue, which prevent an entranceway for bacteria.

The cross-sectional shape of the anchor and subcomponents thereof is round or oval in certain embodiments of the invention.

In certain embodiments, the anchors have overall shapes like letters of the alphabet. These embodiments (collectively referred to as "the Alphabetical Anchors") are identified herein with the term "Anchor" followed by the letter that the anchor most resembles (e.g., Anchor A, Anchor H, Anchor W and Anchor V). There will be some variations to anchors corresponding to a designated letter, but the general designated letter shape will still be evident. Each Alphabetic Anchor comprises at least one tunnel and at least one bridge.

Preferred Anchor A embodiments are shown in FIGS. 3A, 3B, 3C and 3D. Each embodiment includes two vertical components (or anchor bodies) 24 joined by at least one bridge 26 and further includes one open tunnel (or void) 44. The embodiments differ according to the number of closed tunnels they have. The embodiment of FIG. 3A has one closed tunnel 42, the embodiment of FIG. 3B has no closed tunnel, the embodiment of FIG. 3C has two closed tunnels 42, and the embodiment of FIG. 3D has three closed tunnels 42. The tunnels are substantially centered along the fracture line of the anchors.

Preferred Anchor H embodiments are shown in FIGS. 4A, 4B and 4C. Each embodiment includes two vertical components 24 joined by at least one bridge 26 and further includes two open tunnels 44 of substantially similar size. The embodiments differ according to the number of closed tunnels they have. The embodiment of FIG. 4A has no closed tunnel, the embodiment of FIG. 4B has one closed tunnel 42, and the embodiment of FIG. 4C has two closed tunnels 42. The tunnels are substantially centered along the fracture line of the anchors.

Preferred Anchor W embodiments are shown in FIGS. 5A, 5B, 5C and 5D. Each embodiment includes two vertical components 24 that diverge from each other in a distal direction, are joined by at least one bridge 26 and further includes at least one open tunnel 44. The embodiment of FIG. 5A has no closed tunnels and two open tunnels 44, the embodiment of FIG. 5B has one closed tunnel 42 and two open tunnels 44, the embodiment of FIG. 5C has two closed tunnels 42 and two open tunnels 44, and the embodiment of FIG. 5D has one open tunnel 44 and no closed tunnels. The tunnels are substantially centered along the fracture line of the anchors.

Each anchor (alphabetical or otherwise) preferably has two vertical components, at least one horizontal component and at least one tunnel.

The vertical component is the portion of the anchor that will house the hair.

The horizontal component, also called the "bridge", will be the attachment site connecting adjacent vertical components. Bridges are preferably 100 microns to 4 mm long and 100 microns to 4 mm in diameter. The number of bridges present, which attach the vertical components, is related to the number and type of tunnels formed.

Tunnel sizes preferably range from 100 microns to 6 mm in length and 100 microns to 2 mm in diameter.

Figure 2A:
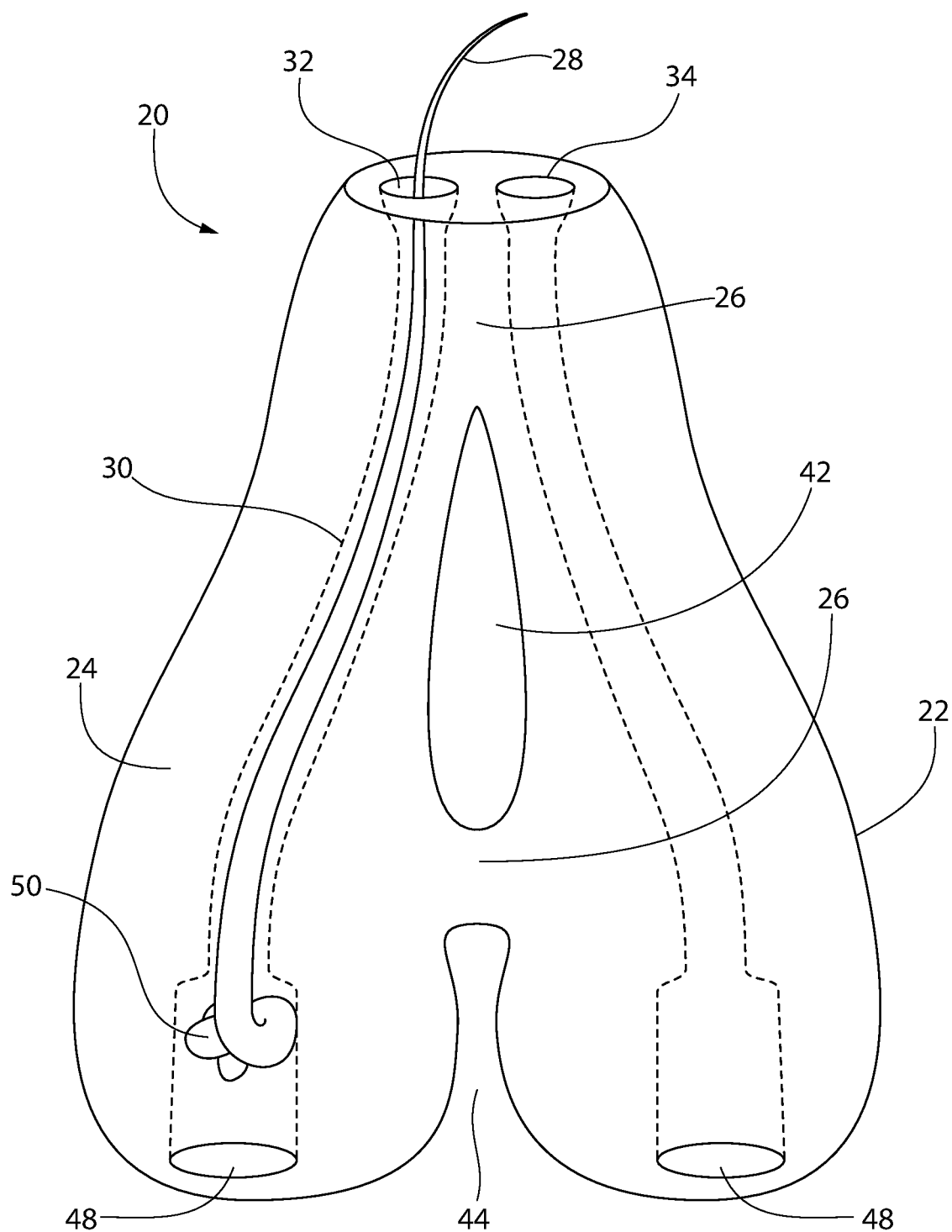
FIGS. 2A, 2B and 2C are front views of three other embodiments of an implant of the invention.
Figure 2B:
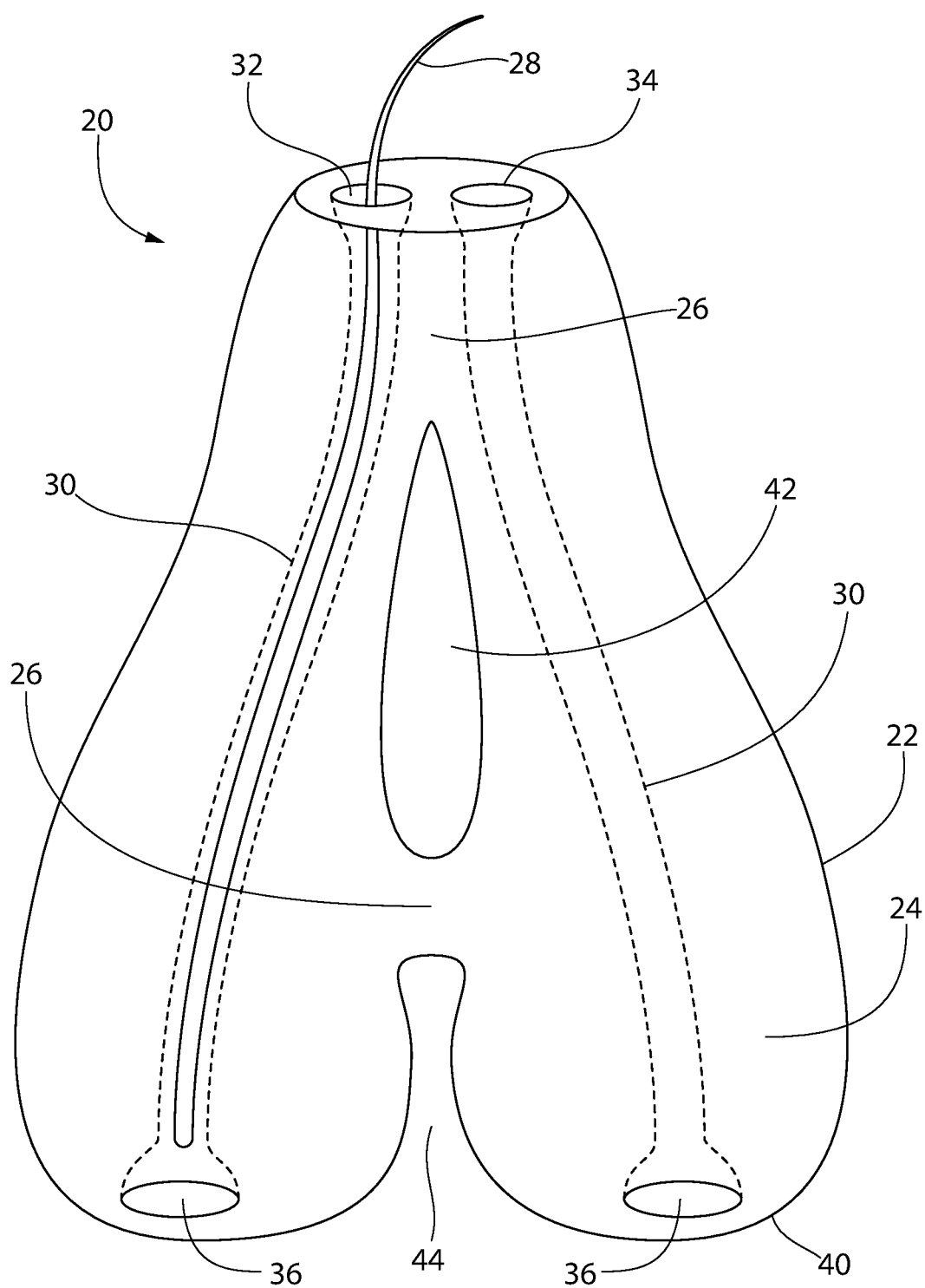

Referring to the embodiments of FIGS. 2A and 2B, each vertical component 24 comprises internal hair chamber 30 having distal orifice 32 at distal end 34 of anchor 22. Internal hair chamber 30 preferably has a diameter from 25-250 microns.

The embodiment of FIG. 2A has knot chamber 48 at a proximal end of each internal hair chamber 30. Each knot chamber 48 has a diameter greater than the respective internal hair chamber 30, such that knot 50 having a diameter greater than the diameter of internal hair chamber 30 is retained within knot chamber and thereby anchors hair 28 to anchor 22. The knot chamber size preferably ranges from 500 microns to 6 mm in length and 100-750 or 100-500 microns in diameter.

The embodiment of FIG. 2B has proximal orifice 36 at proximal end 40 of each internal hair chamber 30.

It is within the scope of the invention for each proximal end of each internal hair chamber within an anchor to have a terminus independently selected from the group consisting of a knot chamber, a proximal orifice and a proximal closure. It is preferred that each proximal end of each internal hair chamber within an anchor have the same type of terminus (e.g., two knot chambers, two proximal orifices or two proximal closures). In certain embodiments, at least one distal orifice 32 and/or at least one proximal orifice 36 is conical and flares open outwardly.

Figure 2C:
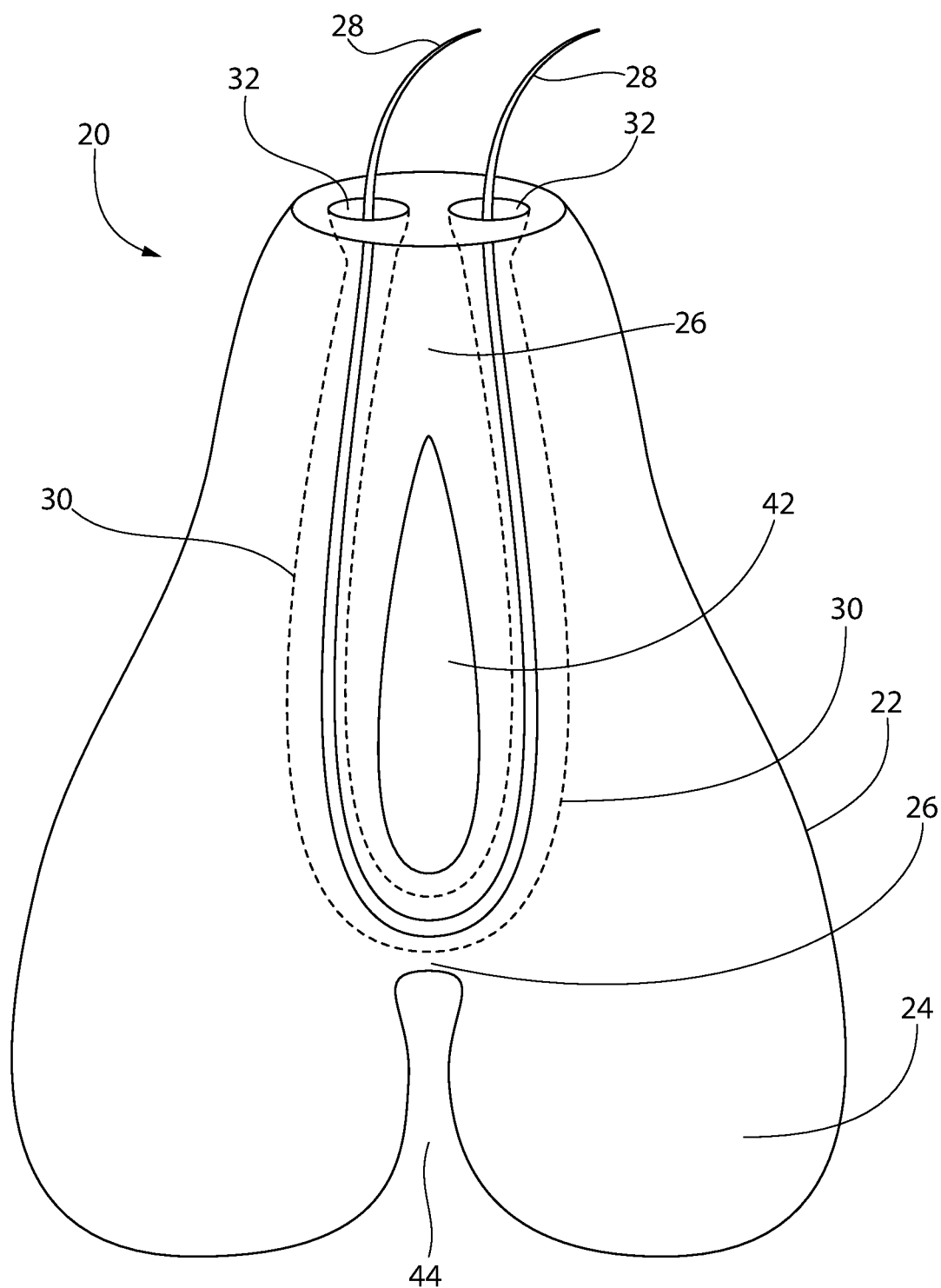
Figure 3A:
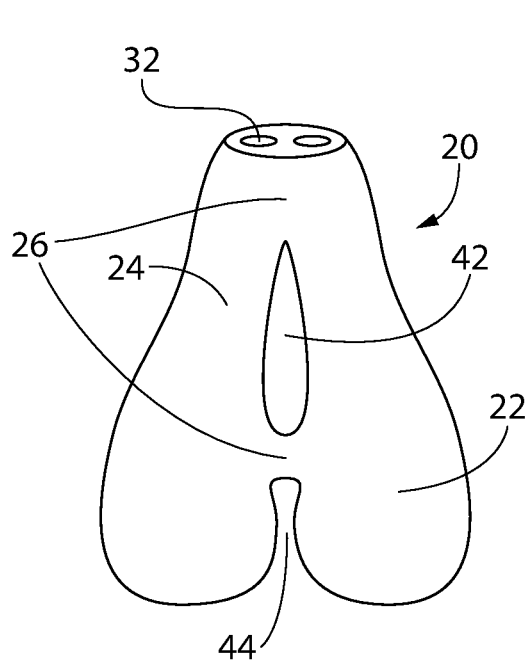
FIGS. 3A, 3B, 3C and 3D show front views of four embodiments of anchors of the invention.
Figure 3B:
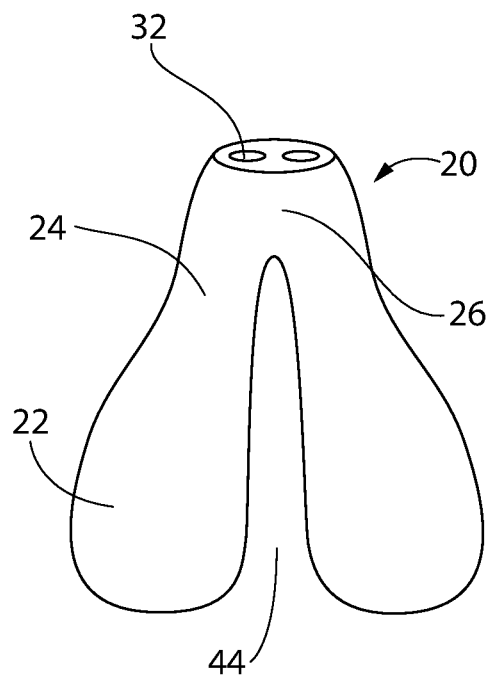
Figure 3C:
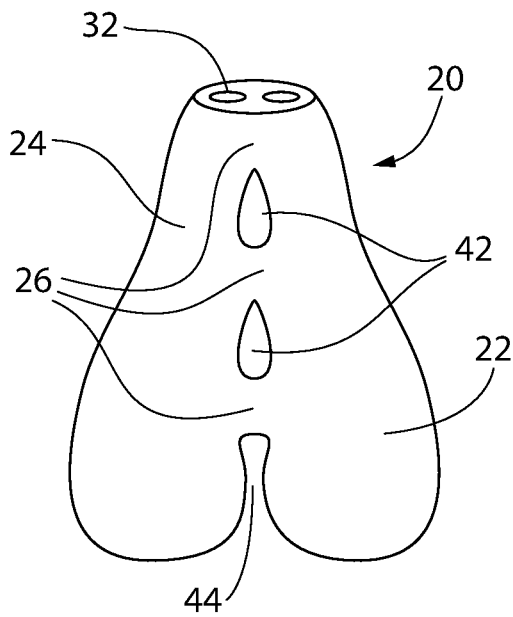
Figure 3D:
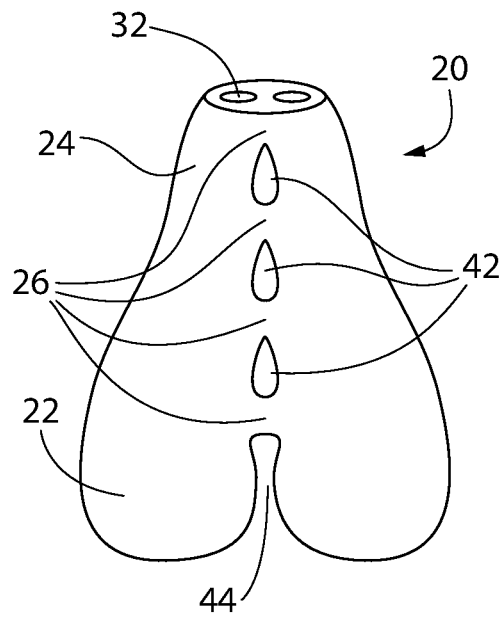

FIG. 2C shows an embodiment with a "looped" internal hair chamber 30, which passes from one vertical component 24 through bridge 26 to the other vertical component 24. A single hair 28 enters internal hair chamber 30 at one distal orifice 32 and exits the chamber at the other distal orifice 32. Placement of hair 28 would preferably involve inserting one strand into one distal orifice 32 and pushing it through the looped internal hair chamber to then exit from the other distal orifice 32 until the exposed lengths of hair differ in length by about 12 mm. A small amount of glue is then placed on the longer exposed segment of hair just above the distal orifice, and the glue-bearing segment of hair is pulled into the internal hair chamber (about 12 mm) such that substantially equal lengths of hair are exposed. The glue is allowed to set, which helps to stabilize or anchor the hair within the internal hair chamber.

Each vertical component preferably has a round or oval cross-sectional shape. Adjacent vertical components can combine with bridges to form many suitable shapes, including the alphabetical shapes discussed above. Thus, for example, adjacent vertical components can be parallel with one another and form an "H" shape in combination with a bridge. Alternatively, adjacent vertical components can be angled relative to each other such that they diverge in a distal direction so as to provide a "W" or "V" shape. Anchor A can be provided when the adjacent vertical components are angled relative to each other such that they diverge in a proximal direction.

The vertical components and their bridges form tunnels. A tunnel is termed "open" if it is not completely enclosed along its length, and termed "closed" if it is open only at the ends thereof.

The external surface of anchor need not be perfectly smooth or linear. Non-limiting examples of external surface variations within the scope of the invention are illustrated by FIGS. 6A-6D in the context of an Anchor A embodiment. Variations of the external surface within the scope of the invention include but are not limited to a vertical component distal upward then downward slope or only a downward slope (undulation 66), a vertical component mid-section concavity 52, a vertical component widening from distal to proximal (most apparent in FIG. 6A), a vertical component proximal bulbous shape 54, and rounded edges on all aspects of the anchor.

Open tunnels 44 are additional examples of external surface features. The open and closed tunnels facilitate a clean fracture of the implant resulting in two parts each including a least one hair. Open tunnels preferably have a length of 0.5-7.5 mm or 1-5 mm, and a depth from 50 microns to 5 mm or from 100 microns to 2 mm.

Figure 6A:
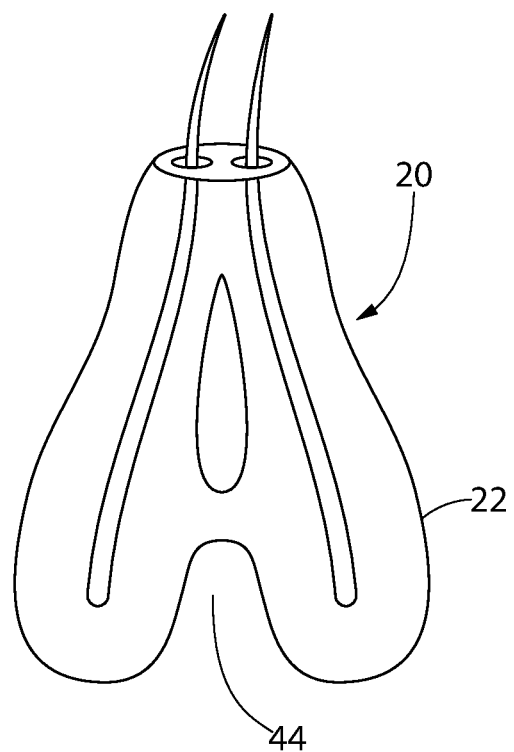
FIGS. 6A, 6B, 6C and 6D show front views of four other embodiments of implants of the invention.
Figure 6B:
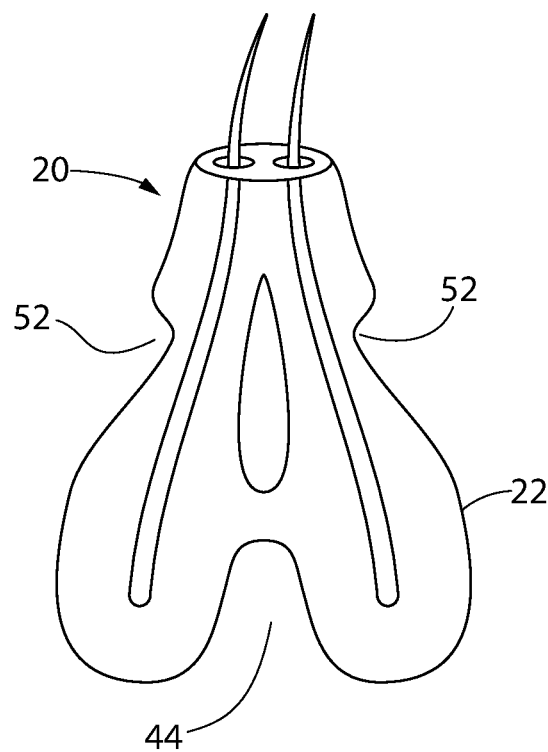
Figure 6C:
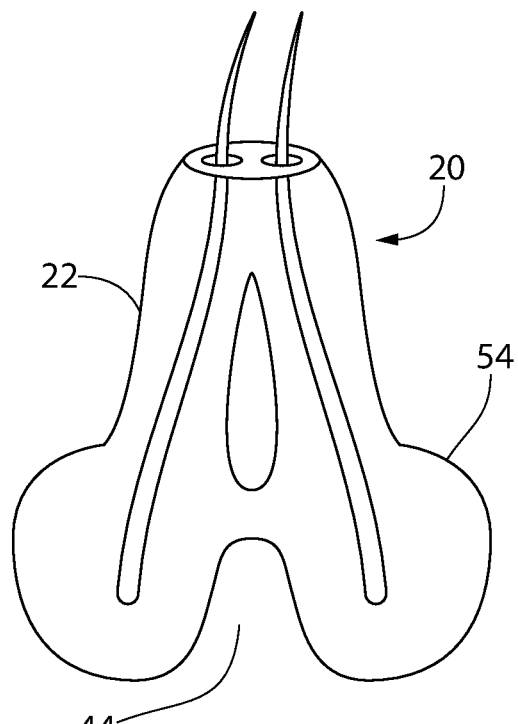
Figure 6D:
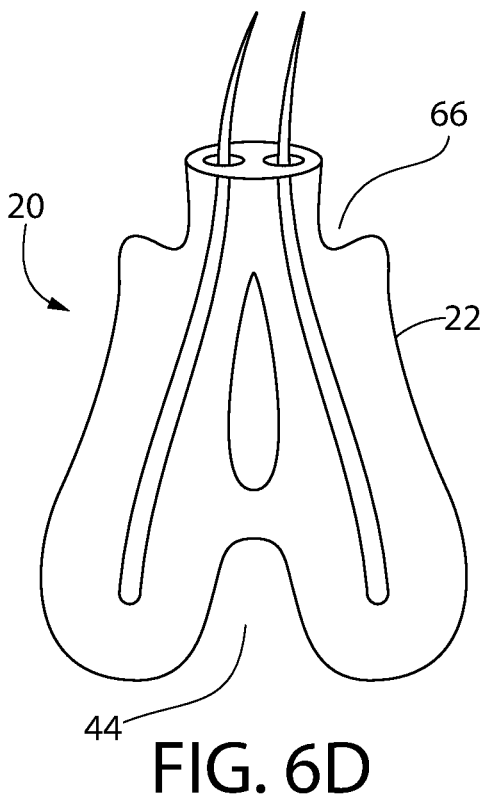

In certain embodiments, the anchor may have an external concavity 52 located at the mid-longitudinal area on both lateral sides (FIG. 6B).

Figure 7:
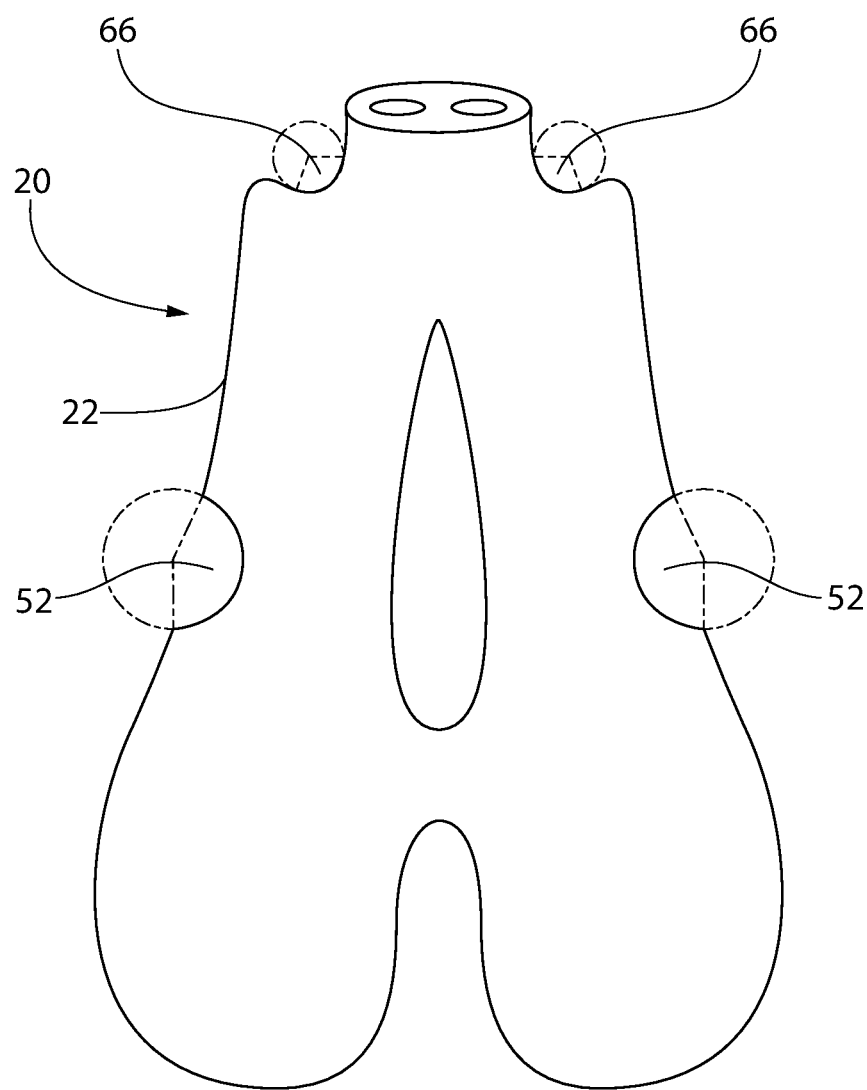
FIG. 7 is a front view of another embodiment of an anchor of the invention.

FIG. 7 shows an embodiment comprising concavity 52 and undulation 66. Concavity 52 and undulation 66 can be described in circle diameter and arc degrees. The circle size diameter preferably ranges from 100 microns to 75 mm or 1 mm to 50 mm, and the arc size preferably ranges from 1 degree to 180 degrees.

Figure 10A:
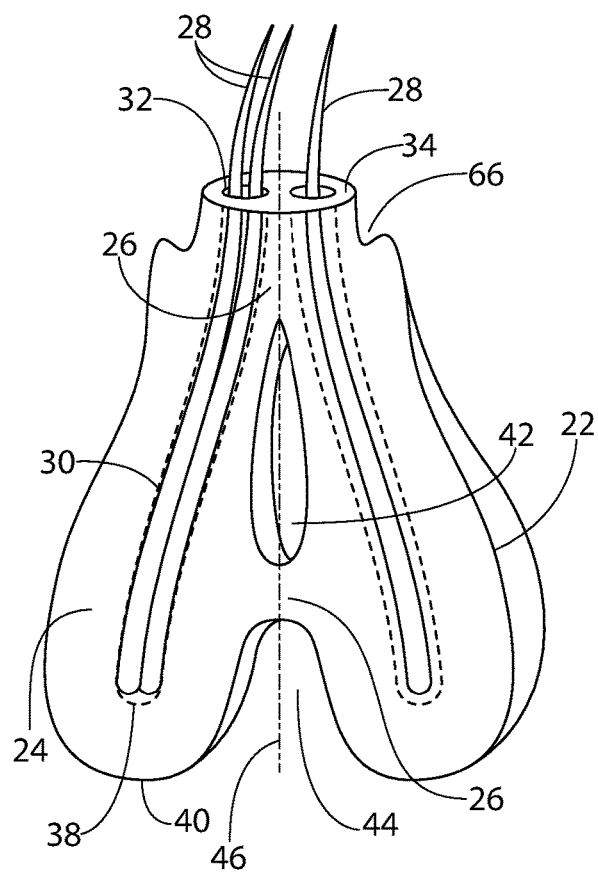
FIGS. 10A and 10B are front perspective views of additional embodiments of an implant of the invention.
Figure 10B:
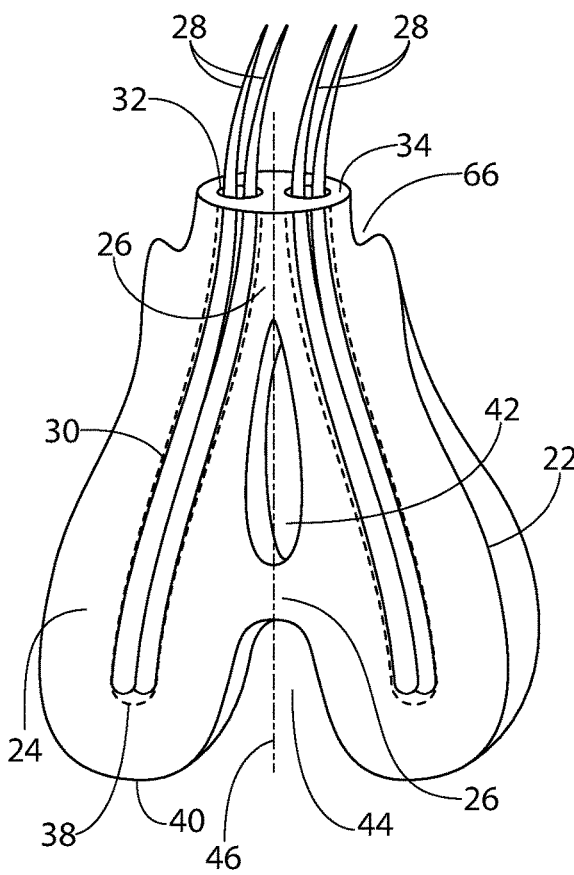

FIGS. 10A and 10B show alternative embodiments of the implant 20, having concavities 52 located at the mid-longitudinal area on both lateral sides, undulations 66 at the distal end of the anchor 22 and three or four hairs 28. It is preferred that each vertical component 24 contain only one internal hair chamber 30 regardless of the number of hairs therein, such that implant 20 has two internal hair chambers 30, with one on each side of the fracture line (excluding the looped hair embodiment described above and shown in FIG. 2C).

Figure 9:
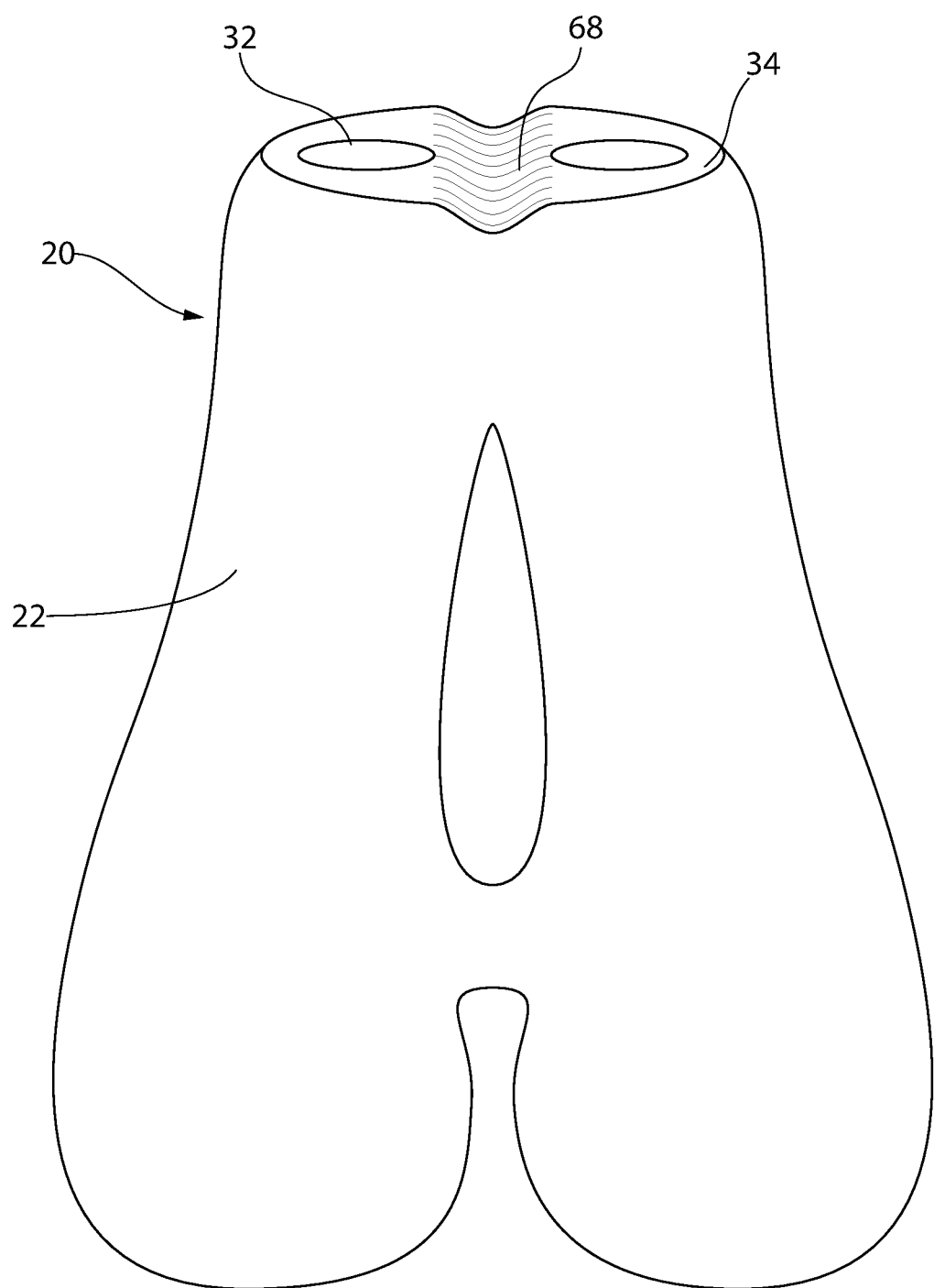
FIG. 9 is a front perspective view of another embodiment of an anchor of the invention.

FIG. 9 shows another external surface feature, wherein rounded indentation 68 is formed in distal end 34 of anchor 22 between distal orifices 32. Rounded indentation 68 is preferably a distal sagittal mid-line U-shaped indentation that will not follow the pattern of a circle and arc description.

Figure 11:
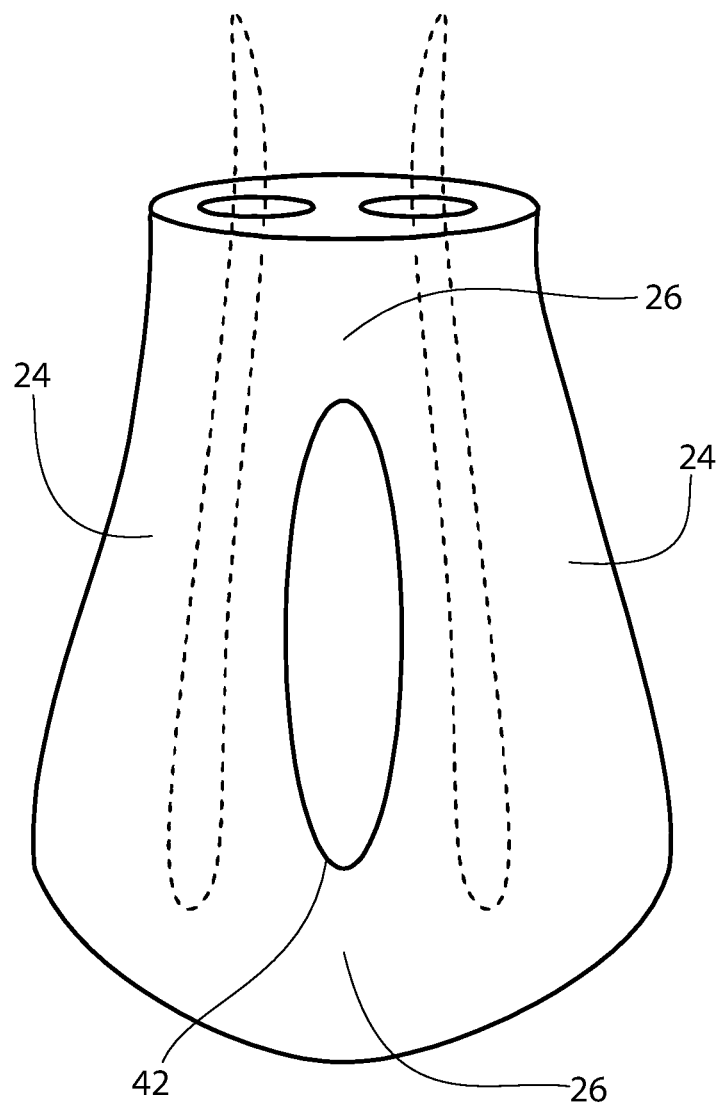
FIG. 11 is a front perspective view of another embodiment of an implant of the invention.

FIG. 11 shows another embodiment of an implant of the invention, which comprises two vertical components 24 joined by bridges 26 and one closed tunnel 42.

FIGS. 15A-15E and 16A-16D depict additional embodiments of the implant anchor 20 that comprises a single internal hair chamber 30 and either two proximal ends 40A/40B (FIGS. 15A-15E) or a single proximal end 40 (FIGS. 16A-16D).

Figure 15A:
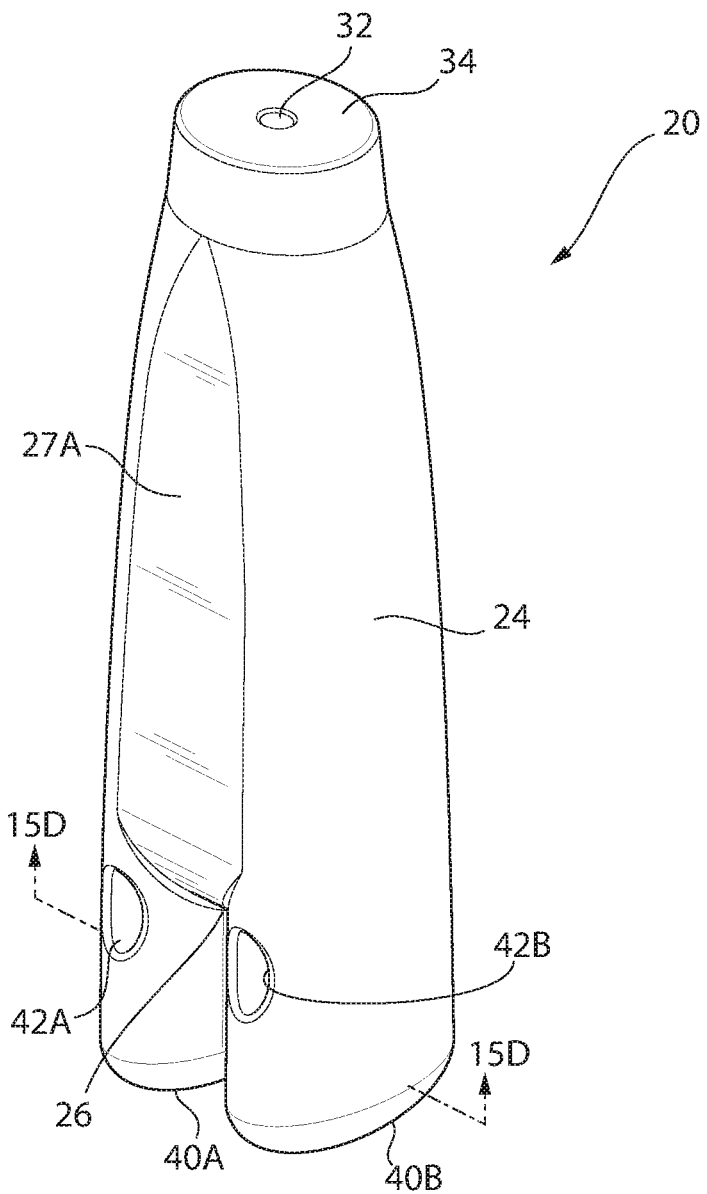
FIG. 15A is a perspective view of another implant anchor embodiment using a single centralized internal hair chamber and two proximal ends.
Figure 15B:
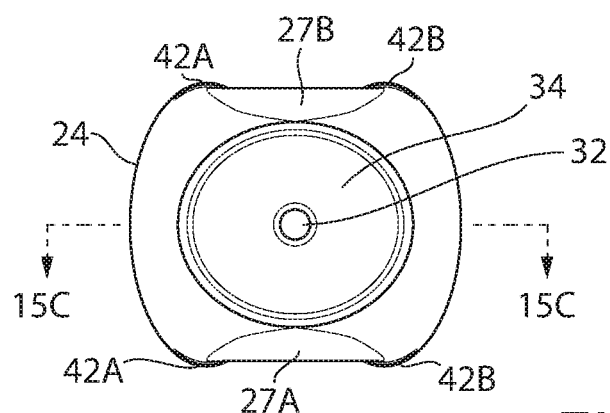
FIG. 15B is a top view of the embodiment of FIG. 15A.
Figure 15C:
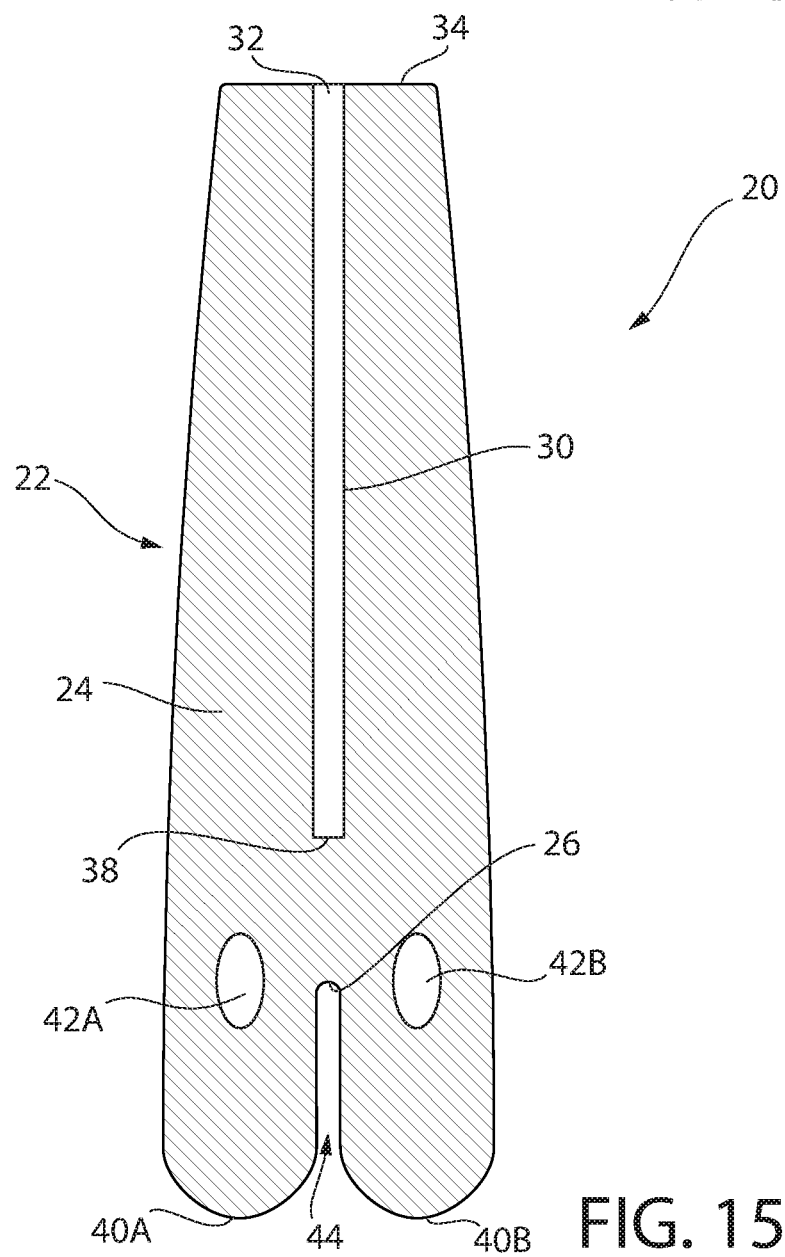
FIG. 15C is a cross-sectional view of the implant anchor of FIG. 15A taken along line 15C-15C of FIG. 15B.
Figure 15D:
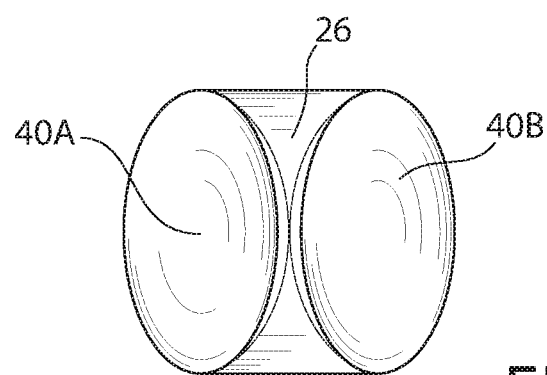
FIG. 15D is bottom view of the implant anchor of FIG. 15A taken along line 15D-15D of FIG. 15A.
Figure 15E:
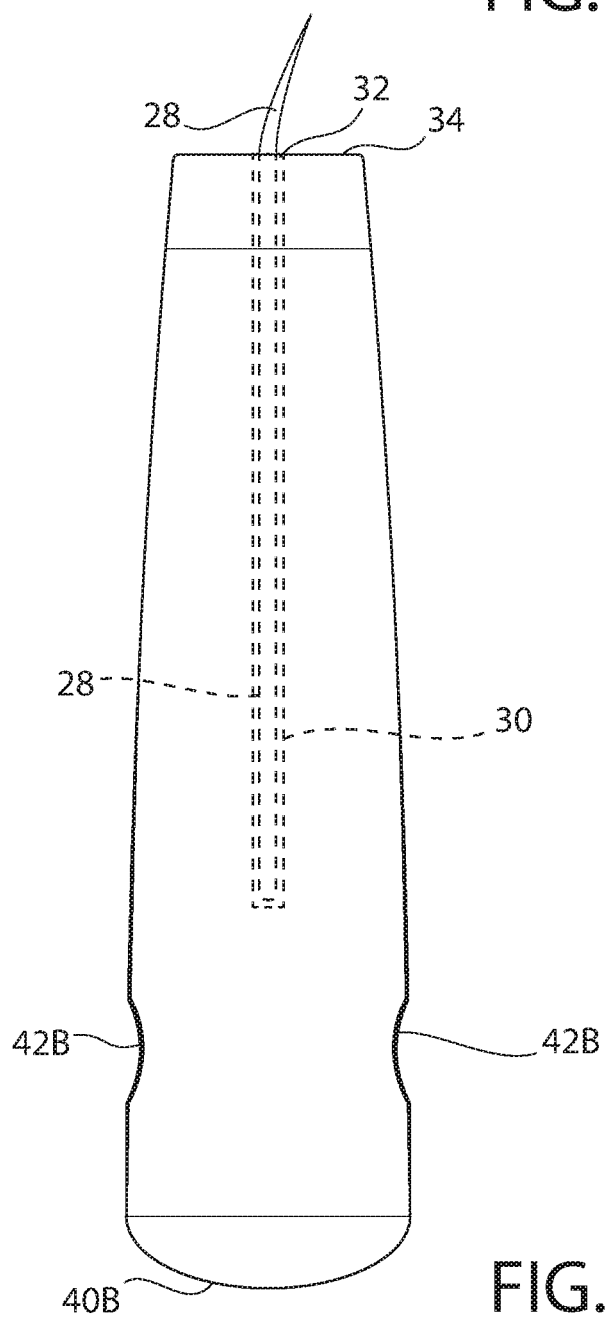
FIG. 15E is a side view of the implant anchor of FIG. 15A with a hair strand shown positioned in the internal channel.

As shown most clearly in FIGS. 15A and 15C, the implant anchor 20 comprises a single anchor body 24 having a centralized internal hair chamber 30. The lower end of the anchor body 24 comprises an open tunnel 44, thereby forming two proximal ends 40A and 40B of the anchor body 24. Adjacent a bridge 26 connecting the two proximal ends 40A/40B at the closed end of the open tunnel 44 are respective closed parallel tunnels 42A and 42B. As can be seen most clearly in FIG. 15B, the outer front and back surfaces of the anchor 20 comprise a respective connecting surface 27A and 27B between the sides of the anchor body 24. FIG. 15D depicts the two rounded proximal ends 40A and 40B and FIG. 15E depicts one hair strand 28 positioned within the centralized internal hair chamber 30 and protruding from the distal orifice 32 at the distal end 34.

Figure 16A:
FIG. 16A is a perspective view of another implant anchor embodiment using a single centralized internal hair chamber and a single proximal end.
Figure 16B:
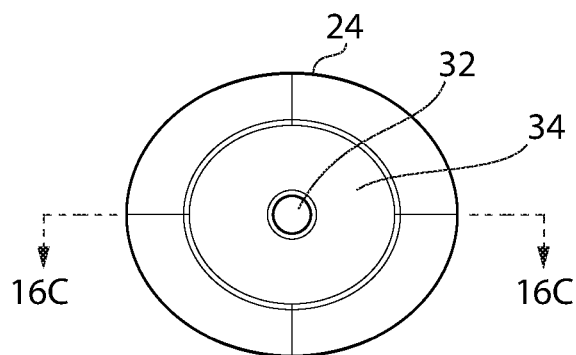
FIG. 16B is a top view of the embodiment of FIG. 16A.
Figure 16C:
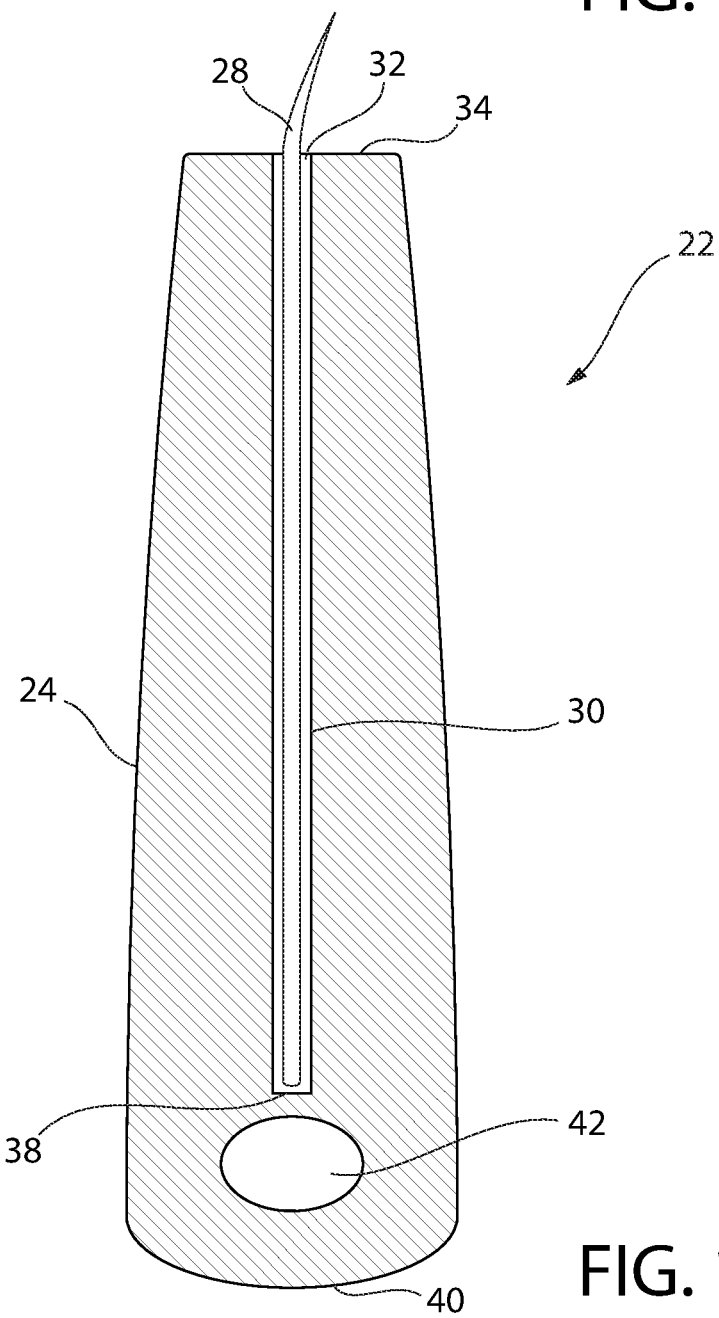
FIG. 16C is a cross-sectional view of the implant anchor of FIG. 16A taken along line 16C-16C of FIG. 16B.
Figure 16D:
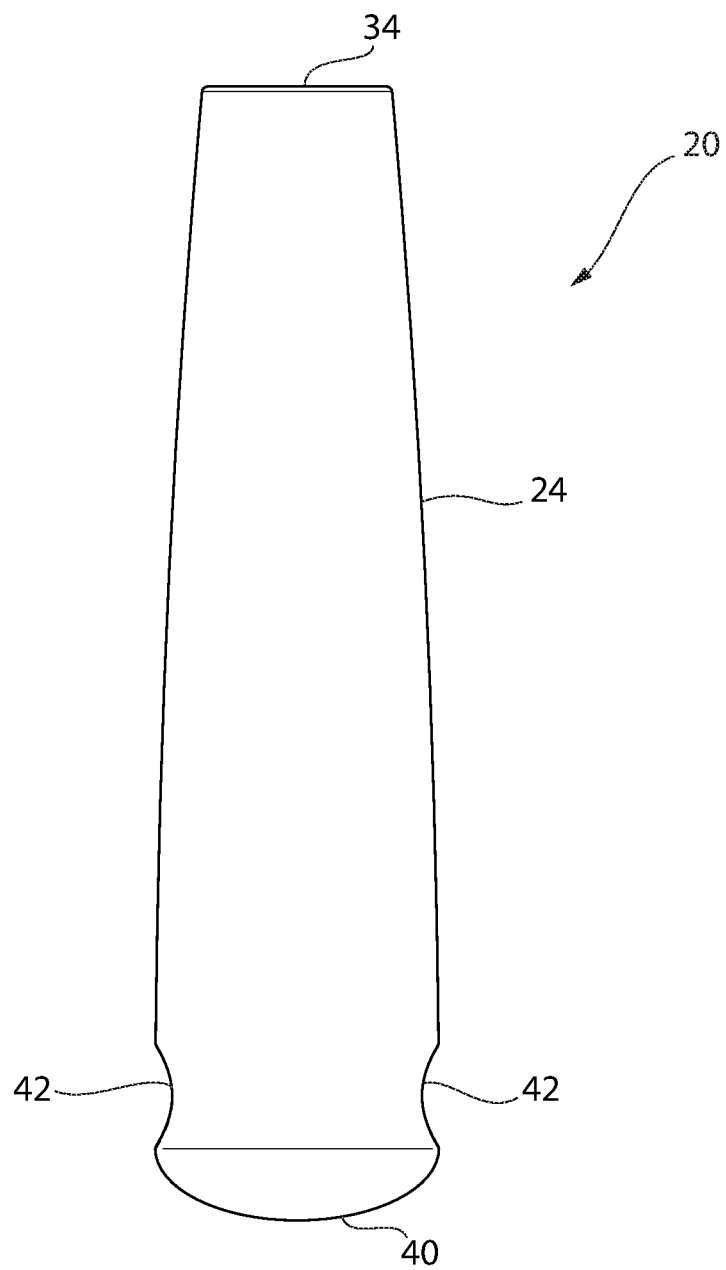
FIG. 16D is side view of the implant anchor of FIG. 16A.
Figure 17A:
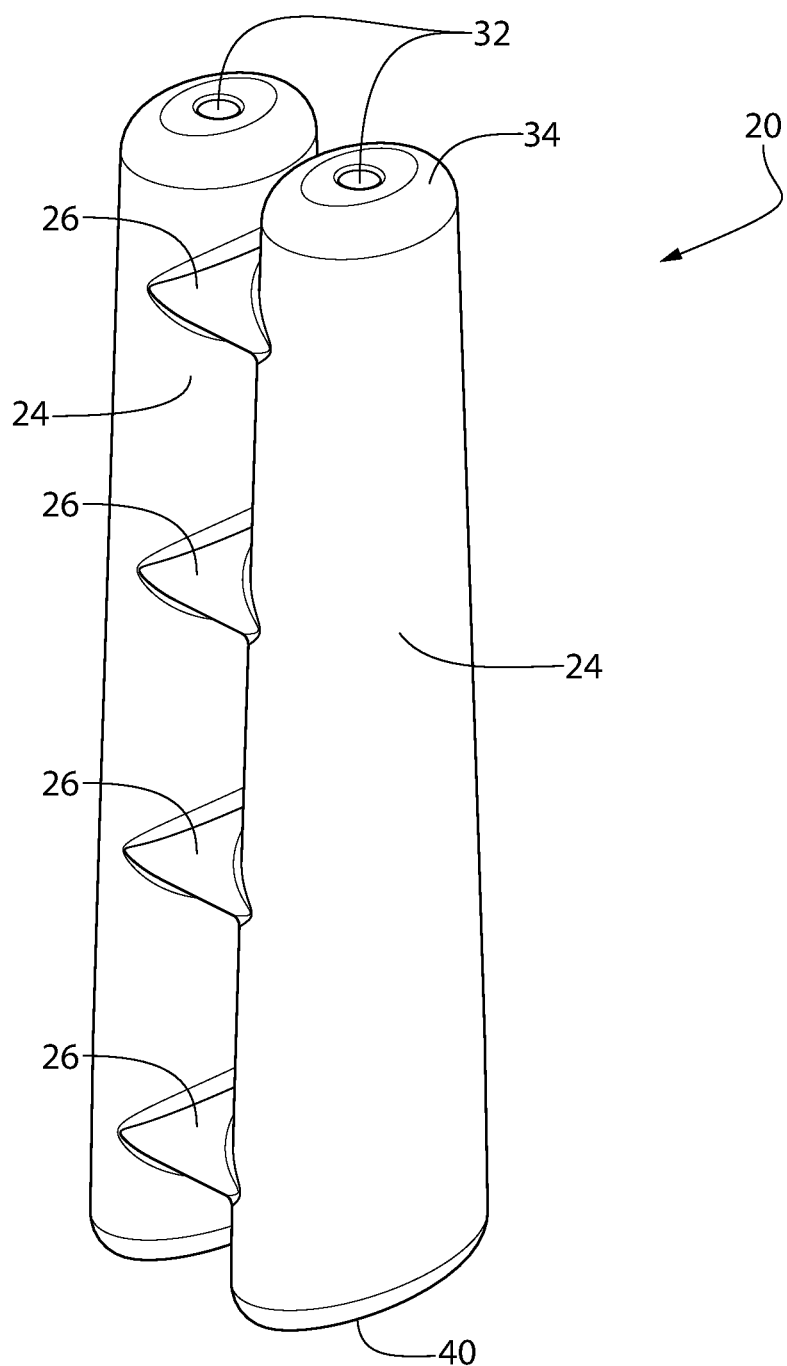
FIG. 17A is a perspective view of another variation of the implant anchor having three closed tunnels and respective open tunnels at the proximal and distal ends thereof.
Figure 17B:
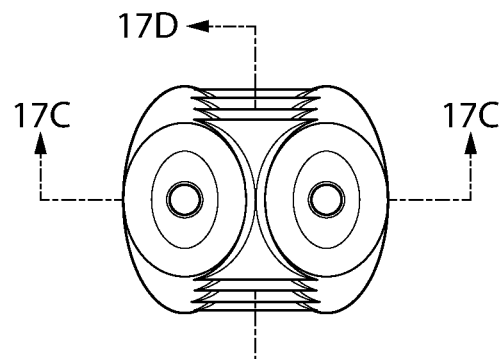
FIG. 17B is a top view of the implant of FIG. 17A.
Figure 17C:
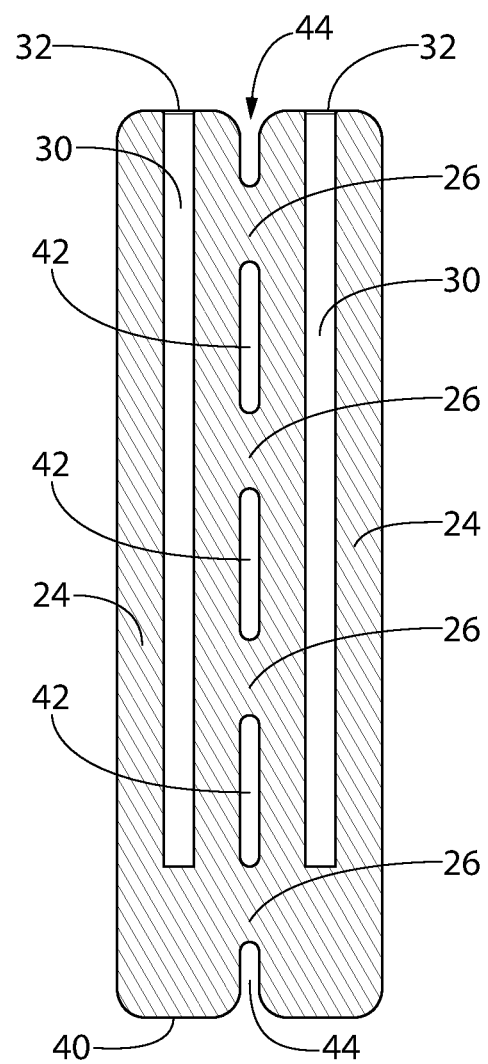
FIG. 17C is a cross-sectional view of the implant taken along line 17C-17C of FIG. 17B.
Figure 17D:
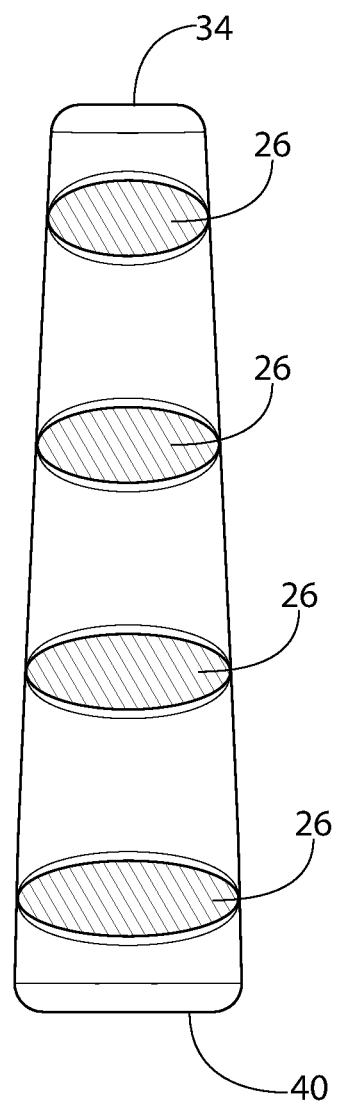
FIG. 17D is a cross-sectional view of the implant taken along line 17D-17D of FIG. 17B.

FIGS. 16A-16D depict the implant anchor 20 which also uses a single internal hair chamber 30 but which comprises a single proximal end 40. As shown most clearly in FIGS. 16A and 16C, the proximal end 40 comprises a single closed tunnel 42. FIG. 16C depicts one hair strand 28 positioned within the centralized internal hair chamber 30 and protruding from the distal orifice 32 at the distal end 34.

In accordance with all other implant anchor embodiments, the anchor variations described in FIGS. 15A-15E and 16A-16D comprise similar materials and utilize the open and closed tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

FIGS. 17A-17D depict a further variation of the implant anchor 20 which uses a pair of internal hair chambers 30 and a plurality of closed parallel tunnels 42 with open parallel tunnels at the distal end 34 and the proximal end 40. In particular, the implant anchor 20 of FIGS. 17A and 17C comprises a plurality of closed tunnels 42 (e.g., three closed tunnels), each separated by a bridge 26, and vertically-aligned along a central portion of the anchor body 24. An open tunnel 44 is present at the distal end 34 and the proximal end 40. The bridges 26 comprise an oval-shape as shown most clearly in FIG. 17D. As shown most clearly in FIG. 17C, on each side of a longitudinal anchor body axis, is a hair chamber 30 that is oriented vertically and each chamber 30 has a distal opening 32 at one end as well as a proximal closure 38 at the other end; these vertically-oriented chambers 30 are parallel to the vertical side walls shown in FIG. 17C. These vertically-oriented hair chambers 30 are also referred to as "straight" chambers since if their axis lines were extended, they would not intersect.

In accordance with all other implant anchor embodiments, the anchor embodiment described in FIGS. 17A-17D comprises similar materials and utilizes the closed tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 18:
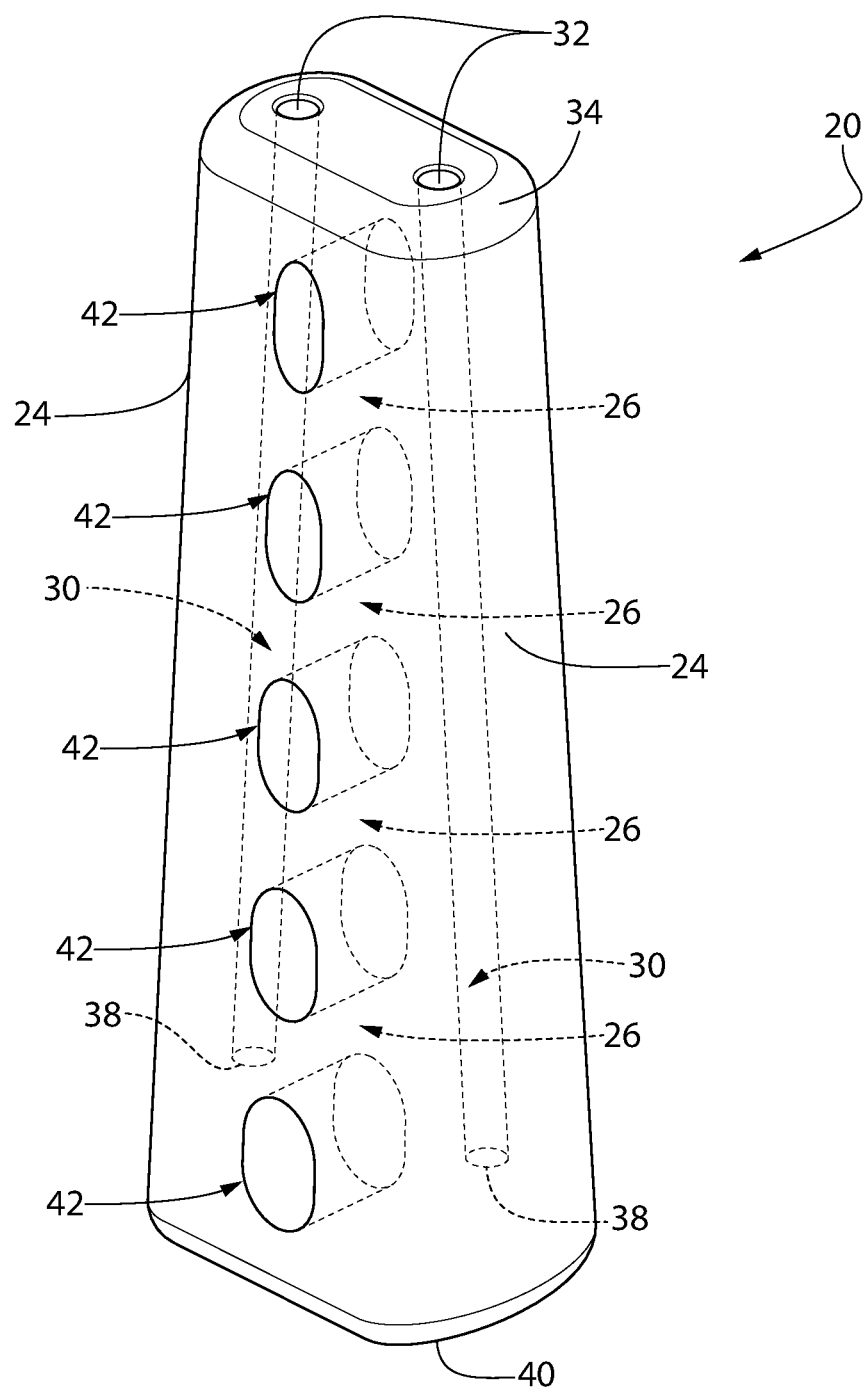
FIG. 18 is a perspective view of a further variation of the implant anchor of the present invention having two hair chambers and having a plurality of closed tunnels but no open tunnels.

FIG. 18 depicts a further variation of the implant anchor 20 which uses a pair of internal hair chambers 30 and a plurality of closed parallel tunnels 42 but no open tunnels at the distal end 34 and the proximal end 40. In particular, the implant anchor 20 of FIG. 18 comprises a plurality of closed tunnels 42 (e.g., five closed tunnels), each separated by a bridge 26, and vertically-aligned along a central portion of the anchor body 24. On each side of a longitudinal anchor body axis, is a hair chamber 30 that is parallel with the side of the hair implant 20 and each channel 30 having a distal opening 32 at one end as well as a proximal closure 38 at the other end. These hair chambers 30 are also referred to as "crossed" chambers since if their axis lines were extended, they would intersect. By way of example only, the upper three closed tunnels may be identical in size (e.g., 100 microns in width and 200 microns in length) while the lower two tunnels are of larger size, e.g., the fourth closed tunnel 42 from the top may comprise a larger size (e.g., 200 microns in width and 400 microns in length) while the bottom-most closed tunnel 42 may comprise an even larger size, e.g., 300 microns in width and 500 microns in length.

Since the implant anchor distal end 34 is smaller in size than the implant proximal end 40, the sides of the anchor body 24 are not vertical but rather splay or taper outward from the top (i.e., distal end 34) to the bottom (i.e., proximal end 40). As such, the sides of the anchor body are "tilted" or "tapered." The hair chambers 30, being parallel to these sides, are therefore "crossed" as described above.

In accordance with all other implant anchor embodiments, the anchor embodiment described in FIG. 18 comprises similar materials and utilizes the closed tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 19:
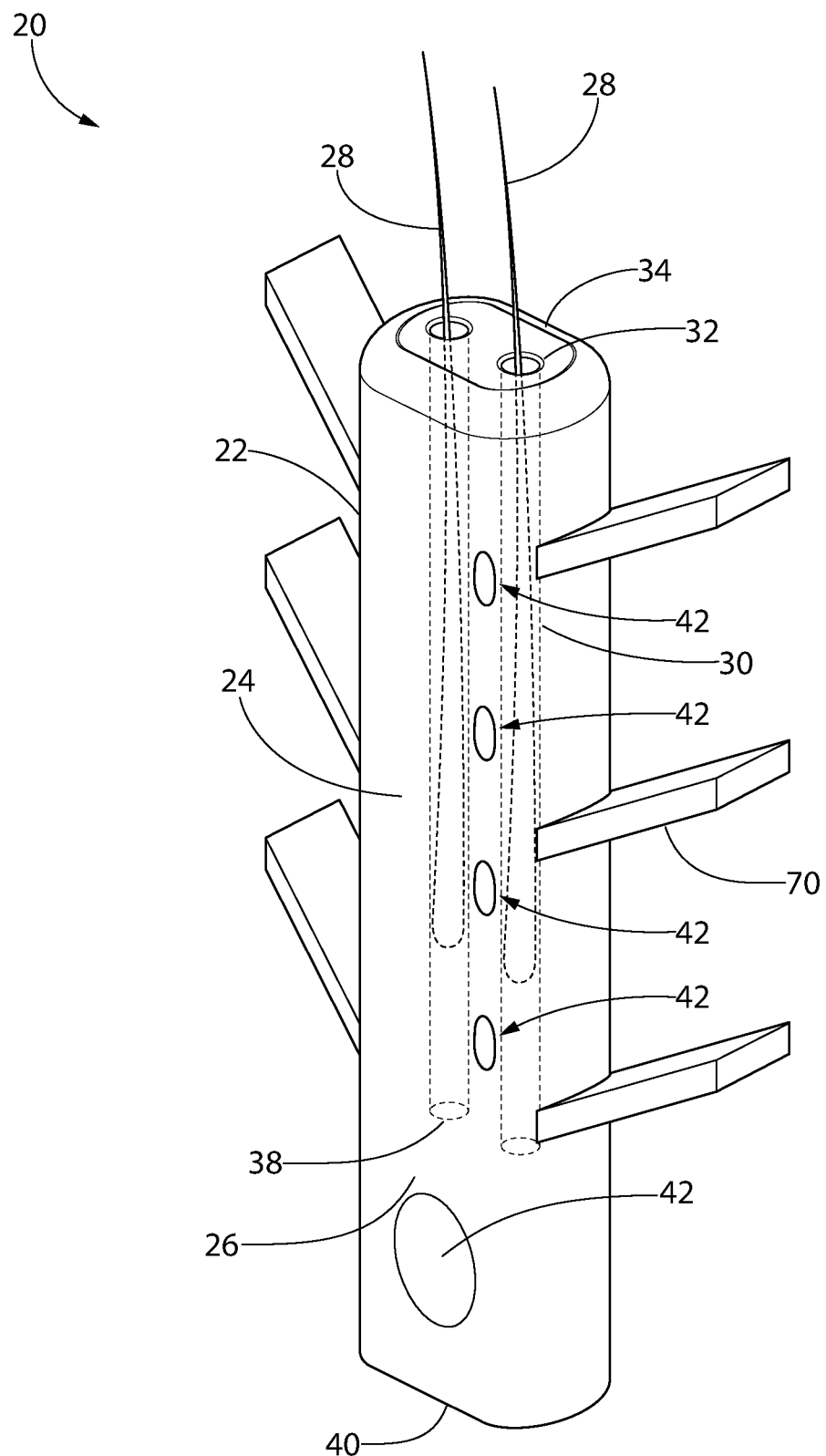
FIG. 19 is a perspective view of another embodiment of an implant anchor of the invention, having a "tree-like" formation with upwardly-swept protrusions.

FIG. 19 depicts a further variation of implant anchor 20 that utilizes a pair of internal hair chambers 30 and a plurality of upwardly swept anchor protrusions 70. In particular, the protrusions 70 emerge from the entire length of the vertical anchor body 24 and project upward at an angle toward the distal end 34 in a "tree-like" fashion. The protrusions 70 promote anchoring the hair strand anchor into the scalp of a hair implant recipient. The anchor possesses a closed tunnel 42 but no open tunnels on the distal end 34 and the proximal end 40. As with all other embodiments of the invention depicted in the drawings, tunnels, protrusions, tunnels in protrusions and other features can be added to or subtracted from those shown (or not shown) in the drawings to provide modified versions of the depicted embodiments.

Figure 20:
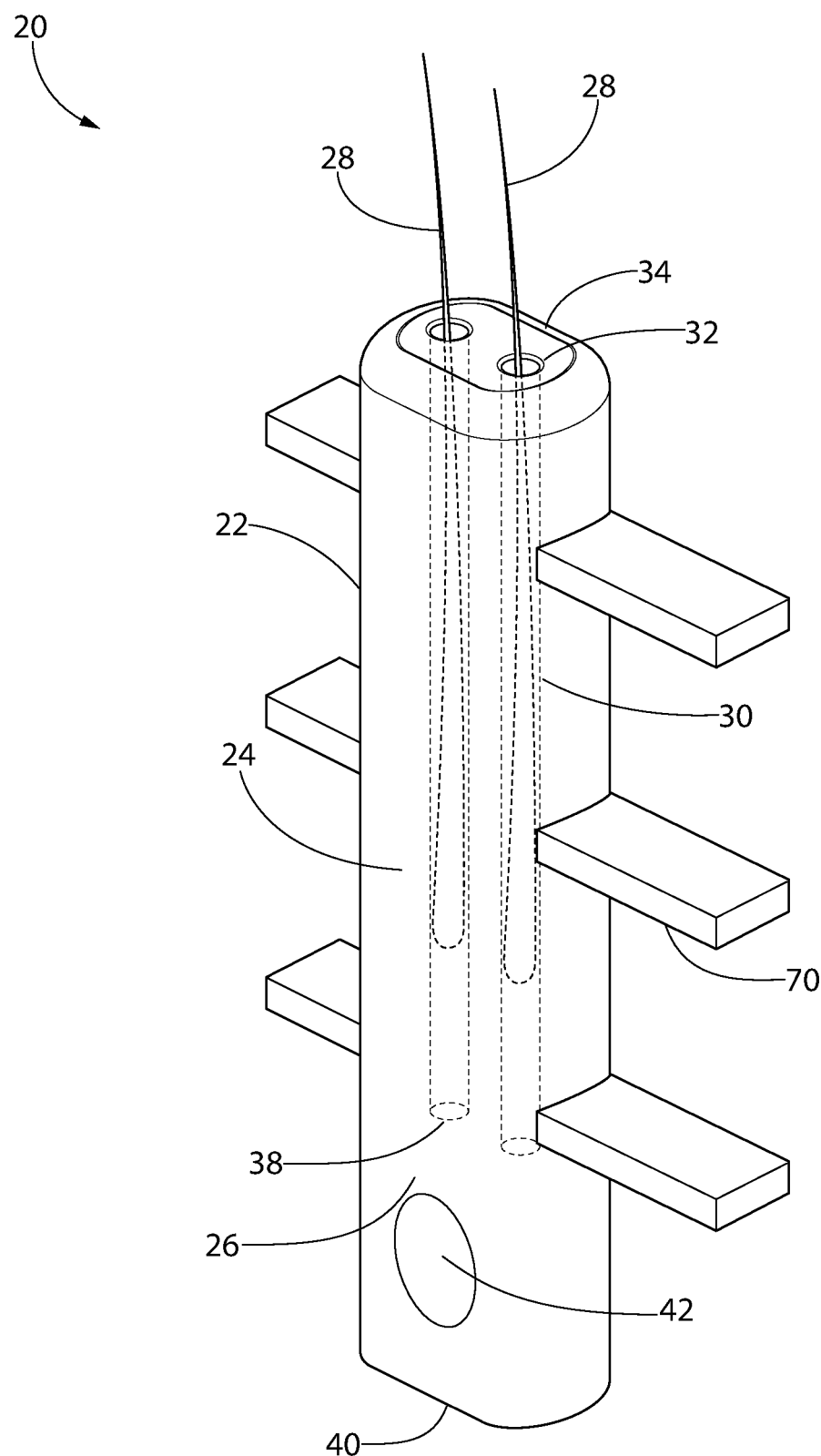
FIG. 20 is a perspective view of another embodiment of an anchor of the invention, having a "tree-like" formation with lateral protrusions.

FIG. 20 depicts a further variation of implant anchor 20 that also utilizes a pair of internal hair chambers 30, a plurality of lateral anchor protrusions 70, and a closed tunnel 42 but no open tunnels on the distal end 34 and the proximal end 40. In particular, this embodiment features protrusions 70 that project perpendicularly from the anchor body 24. The protrusions 70 form a "cross-like" pattern because of the way the protrusions 70 intersect with the anchor body 24 of the anchor 22.

Figure 21:
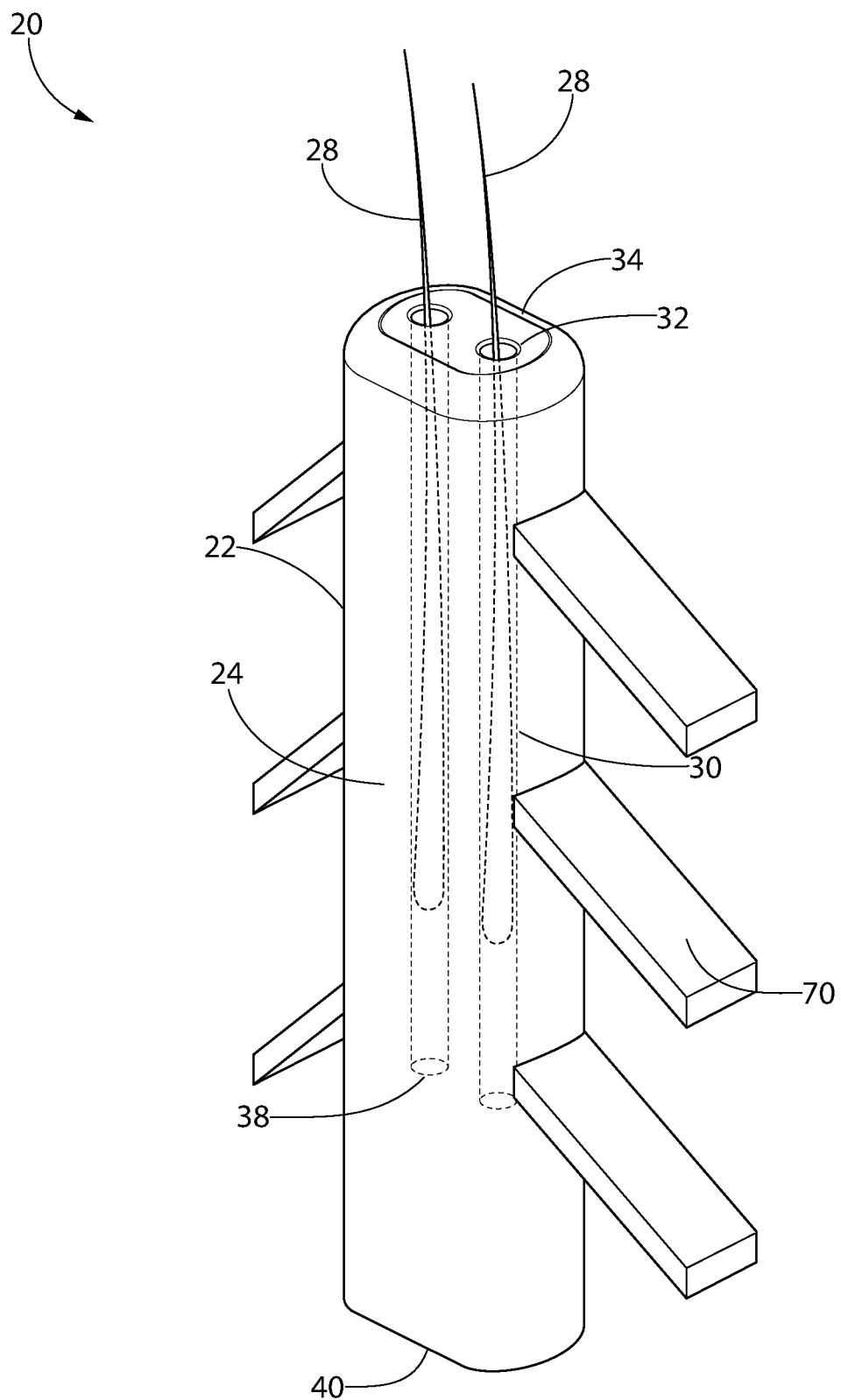
FIG. 21 is a perspective view of another embodiment of an anchor of the invention, having a "tree-like" formation with downwardly-swept protrusions.

FIG. 21 depicts a further variation of implant anchor 20 that utilizes a pair of internal hair chambers 30, a plurality of downwardly-swept anchor protrusions 70, and no open or closed tunnels. In particular, the protrusions 70 emerge from the entire length of the anchor body 24 and project downward at an angle toward the proximal end 40 in a way that resembles the fins of a rocket.

In accordance with all other anchor embodiments, the anchor embodiments described in FIGS. 19-21 comprise similar materials and utilize the closed tunnels (of FIGS. 19-20) and the protrusions for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 22A:
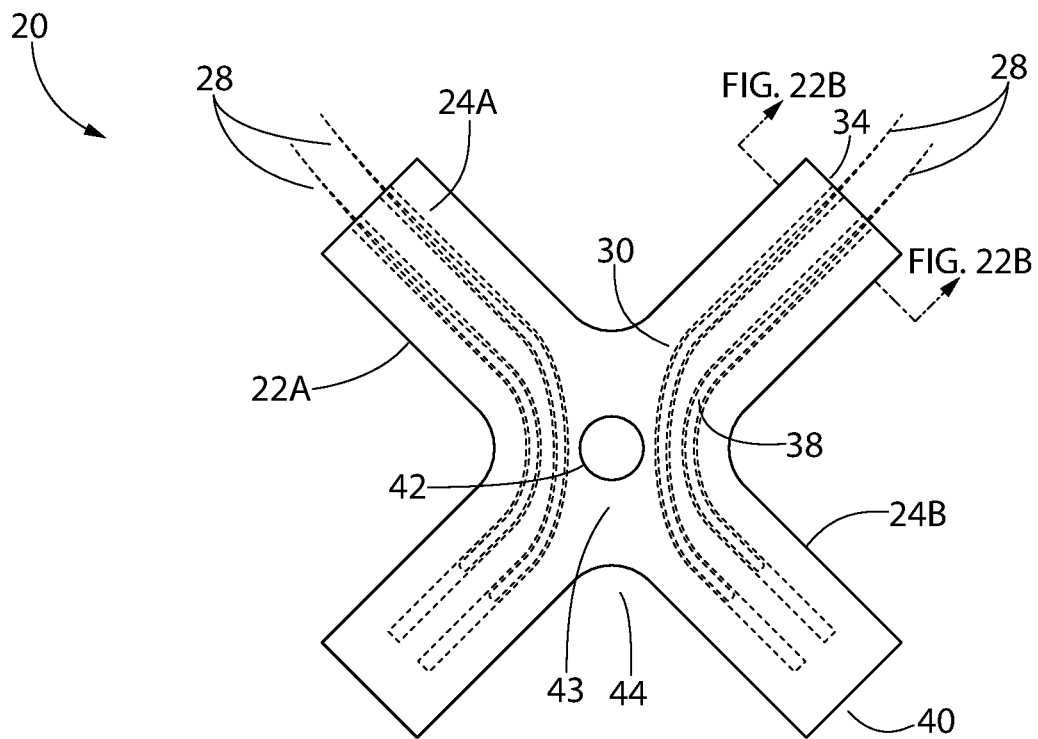
FIG. 22A is a front view of another embodiment of an implant anchor of the invention, having a cruciform configuration.
Figure 22B:
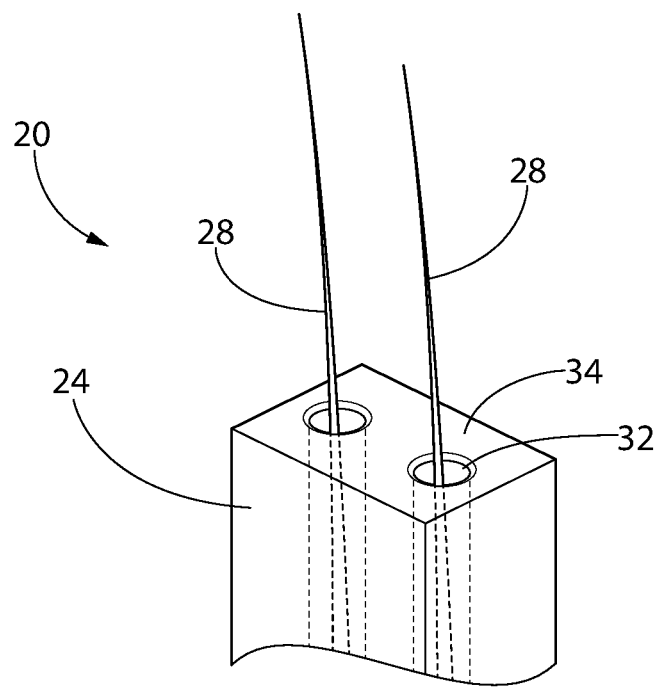
FIG. 22B is a partial perspective view of the implant anchor of FIG. 22A taken along line 22B-22B of FIG. 22A.

FIGS. 22A and 22B depict a further embodiment of implant anchor 20. In particular, FIG. 22A depicts an implant having a cruciform configuration 22A with two hair element arms 24A and two anchor arms 24B. The hair element arms 24A comprise respective distal ends 34, and the anchor arms 24B comprise respective proximal ends 40. Each hair element arm 24A comprises internal hair chambers 30 with proximal closures 38, distal orifices 32 and each chamber 30 containing one hair 28. Additionally, the implant anchor contains one closed tunnel 42, which is located at a central point 43.

FIG. 22B shows a partial perspective view of a distal end 34 of the one of the hair element arms depicted in FIG. 22A. The cross-section illustrates two hairs 28 emerging from the two distal orifices 32.

In accordance with all other anchor embodiments, the anchor embodiment described in FIGS. 22A and 22B comprises similar materials and utilizes the closed tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 23:
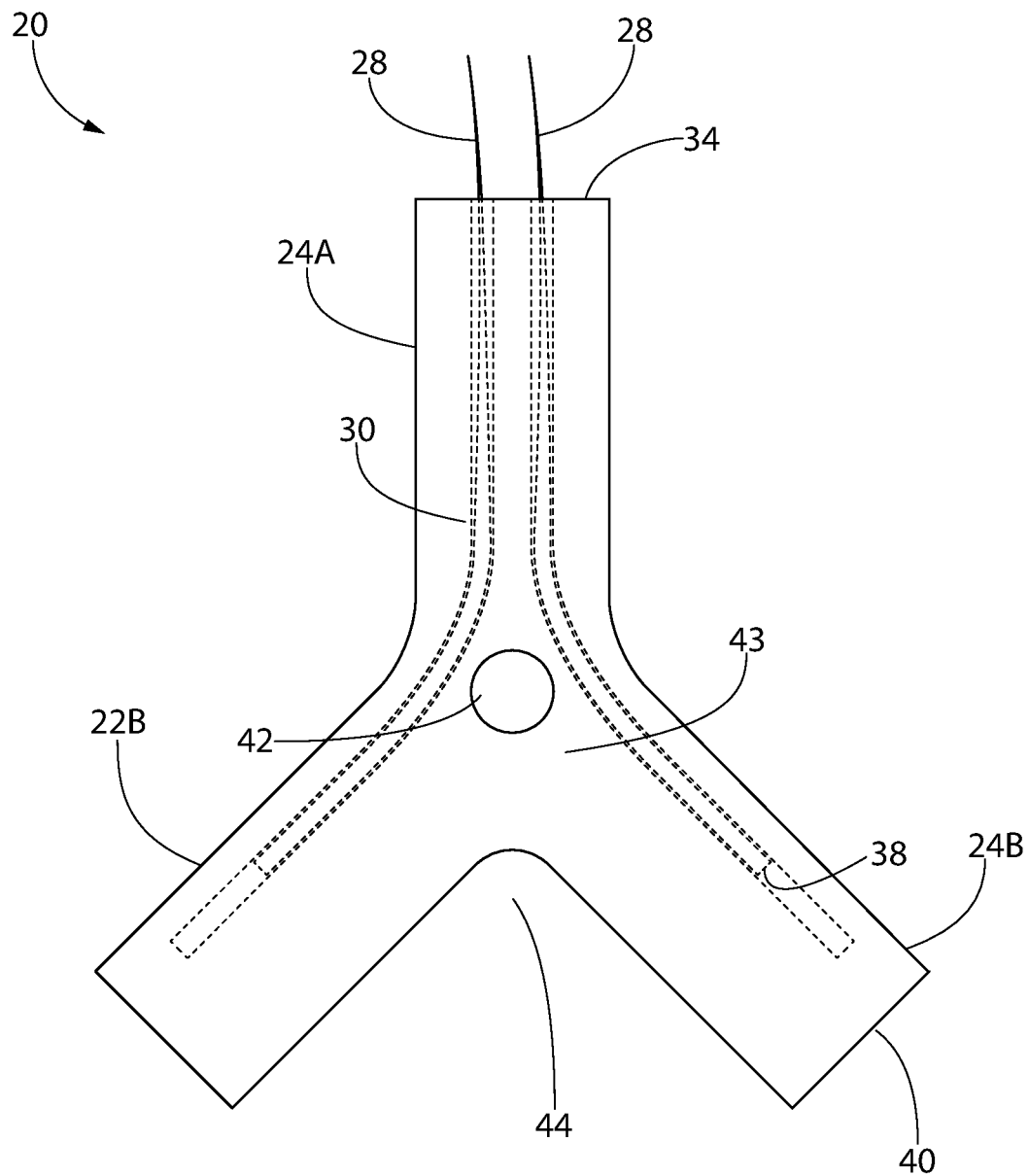
FIG. 23 is a front view of another embodiment of an anchor of the invention, having an inverted "Y-shape" configuration.

FIG. 23 depicts a further embodiment of the implant anchor 20 utilizing an inverted Y-shaped configuration 22B having a single hair element arm 24A and two anchor arms 24B. The hair element arm 24A comprises internal hair chambers 30 with proximal closures 38, and orifices on the distal end 34 of the arm 24A. More particularly, the implant anchor 22B is shaped like an inverted "Y." A closed tunnel 42 is positioned at a central point where arms 24A and 24B are coupled.

Figure 24:
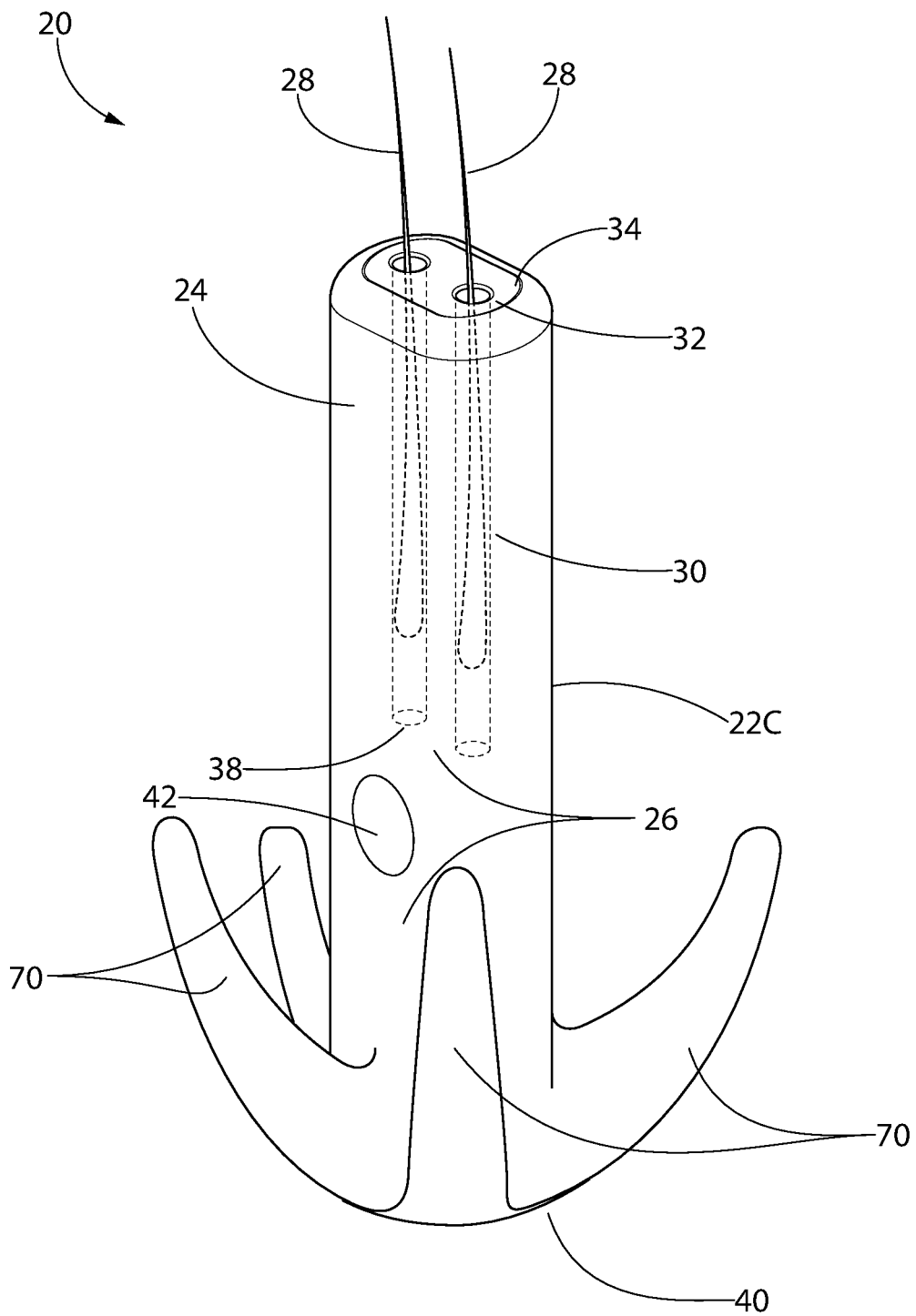
FIG. 24 is a perspective view of another embodiment of an implant anchor of the invention, having a "barbed" configuration.

FIG. 24 depicts a perspective view of a further embodiment of the implant anchor 20 utilizing two internal hair chambers 30 with proximal closures 38 and distal orifices 32 of the vertical anchor body 24. Beneath the internal hair chambers on the vertical component is a closed tunnel 42 that is flanked by two bridges 26 above and below the closed tunnel. From the proximal end 40 extend four curved protrusions 70 that curve upward toward the distal end of the anchor. The entire anchor 22 resembles a "fishhook" or barbed anchor body 22C structure, with each of the curved protrusions 70 spaced radially, 90 degrees apart from each other.

Figure 25:
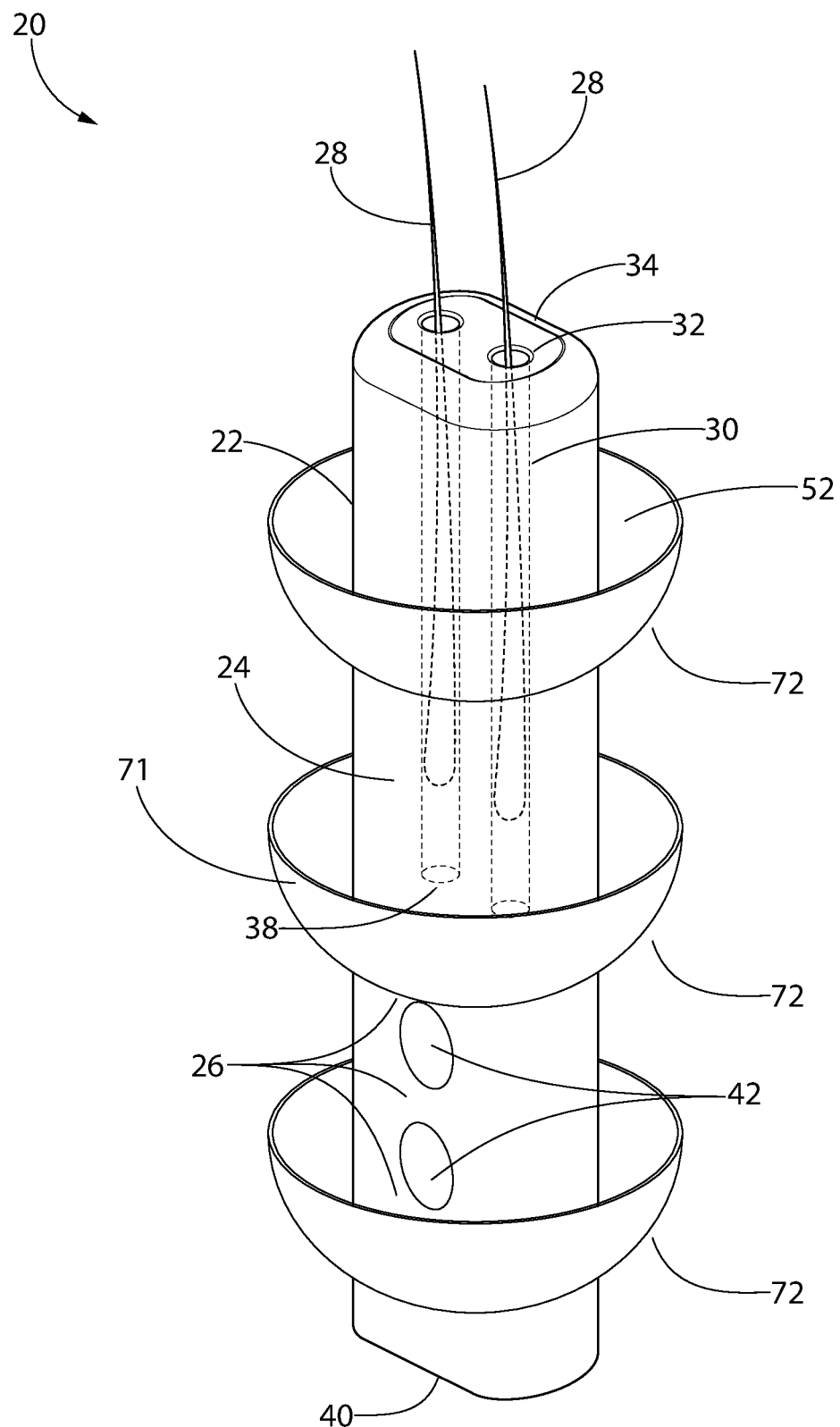
FIG. 25 is a perspective view of another embodiment of an implant anchor of the invention, having a plurality of "cup-shaped" structures along the anchor body.

FIG. 25 depicts a further embodiment of the implant anchor 20 utilizing a plurality of equally spaced "cup-shaped" structures 71 encircling the anchor body with concavities 52 opened toward the distal end 34 of the anchor body and convexities 72 pointed downward toward the proximal end 40 of the anchor body. In particular, the anchor body features two closed tunnels 42 that are vertically aligned along a central position of the anchor body 24. The embodiment also features two internal hair chambers 30 with proximal closures 38 and distal orifices 32.

Figure 26:
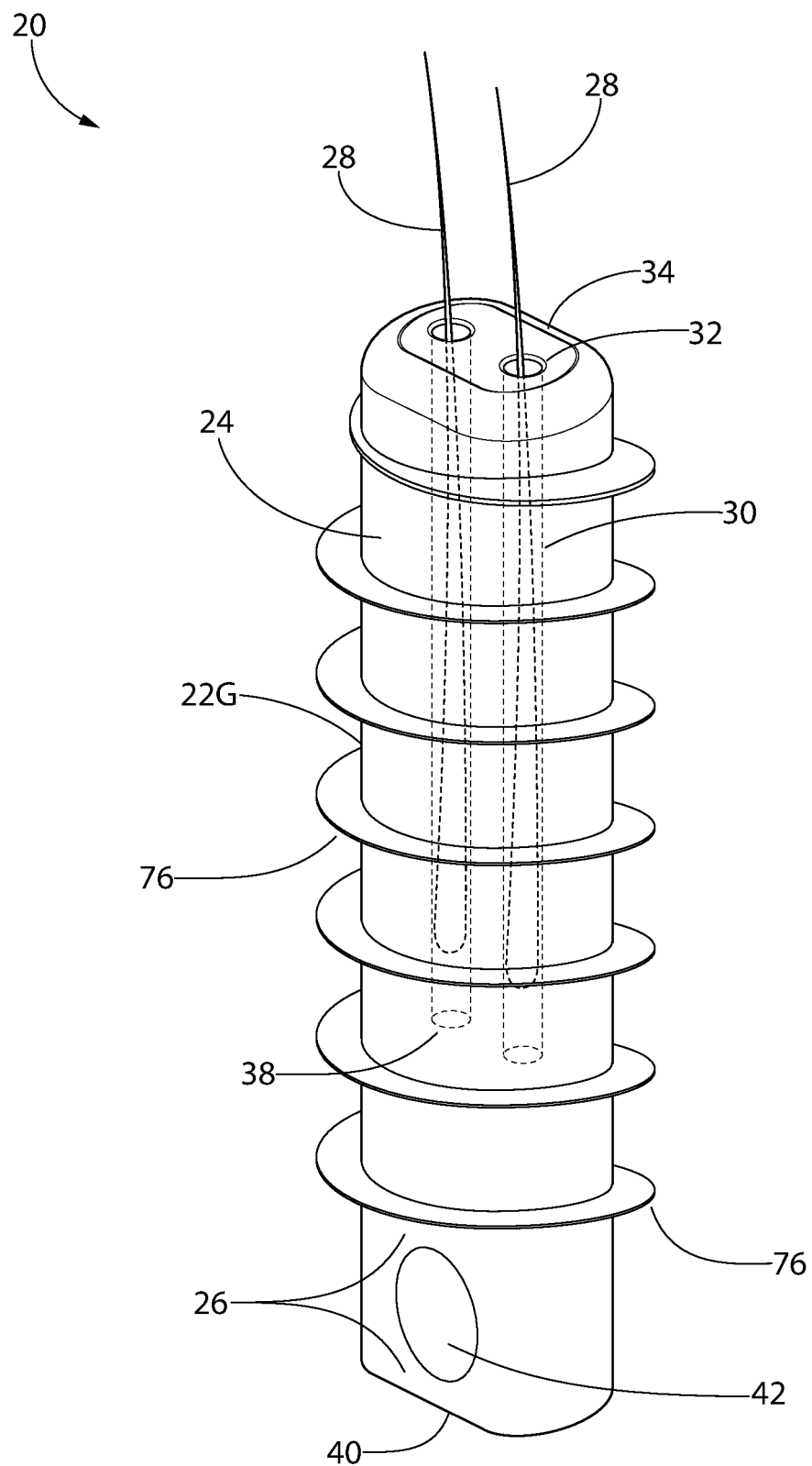
FIG. 26 is a perspective view of another embodiment of an implant anchor of the invention, having a helix or "screw" type structure around the anchor body.

FIG. 26 depicts a further embodiment of the implant anchor 20 utilizing a vertical anchor body 24 with a "screw-shaped" anchor 22G configuration, wherein the anchor body is helically encircled by a thread 76. The pitch ratio of thread 76 is preferably 1 to 5, wherein the pitch ratio as used herein is defined as the diameter of the anchor body (not including the thread) divided by the distance along the longitudinal axis of the anchor body between adjacent crests of the thread (i.e., the height of one complete rotation of the helical thread). Two internal hair chambers 30 having proximal closures 38 emerge from two distal orifices 32 on the anchor. Adjacent the proximal end of the anchor, two bridges 26 are vertically aligned with a closed tunnel 42.

Figure 27:
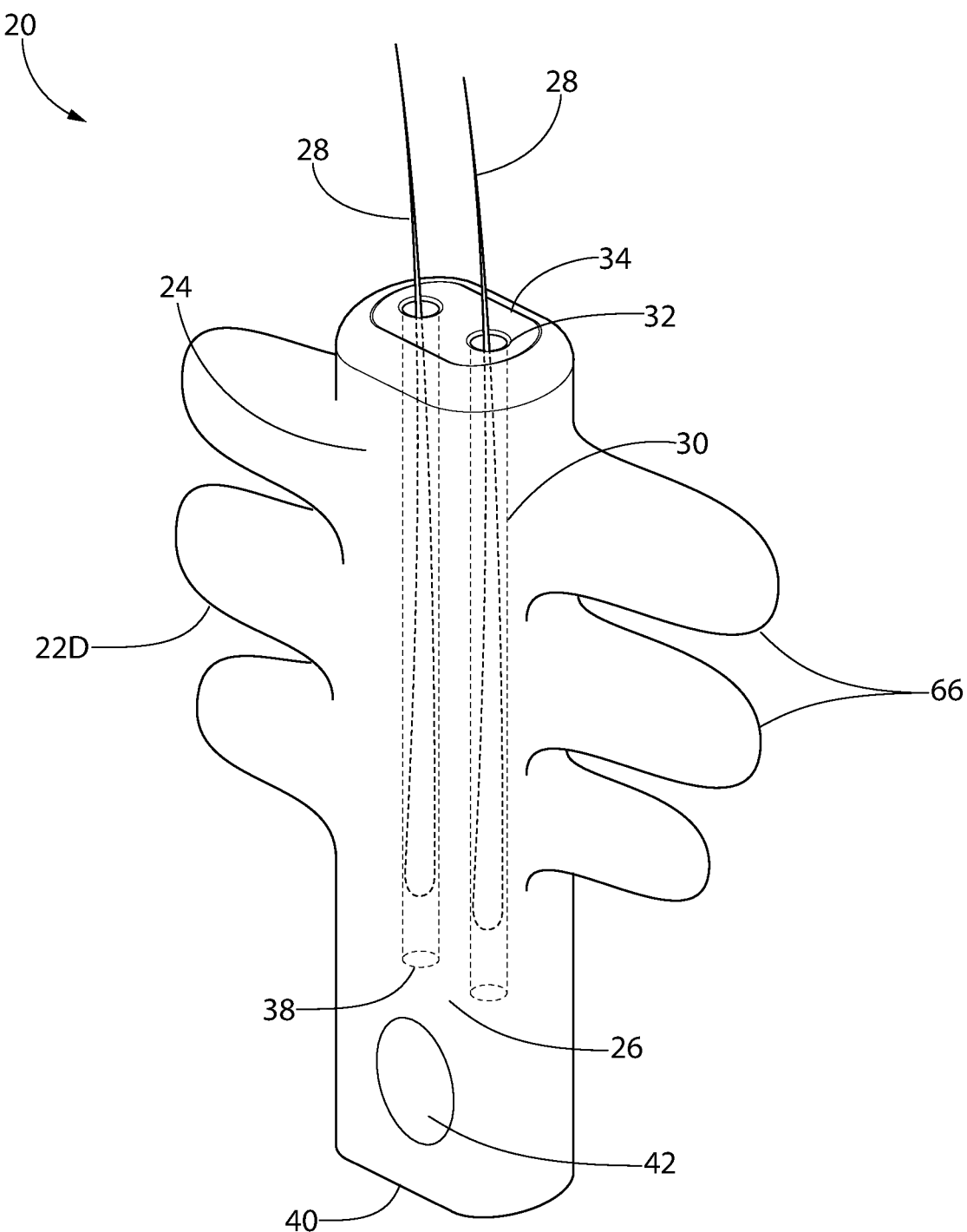
FIG. 27 is a perspective view of another embodiment of an implant anchor of the invention, having a racket-shaped configuration.

FIG. 27 depicts a further embodiment of the implant anchor 20 utilizing two internal hair chambers 30 that emerge from distal orifices 32 and have proximal closures 38. The anchor 22D resembles a racket and possesses a plurality of protrusions 70 extending laterally from a distalmost "head" portion of the anchor body with no such protrusions on the "handle" portion proximal to the "head". A closed tunnel 42 is positioned proximal to the internal hair chambers and centrally aligned on the anchor body 24.

In accordance with all other anchor embodiments, the anchor embodiments described in FIGS. 23-27 comprise similar materials and utilize closed tunnels and projections (i.e., protrusions, undulations, etc.) for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 28:
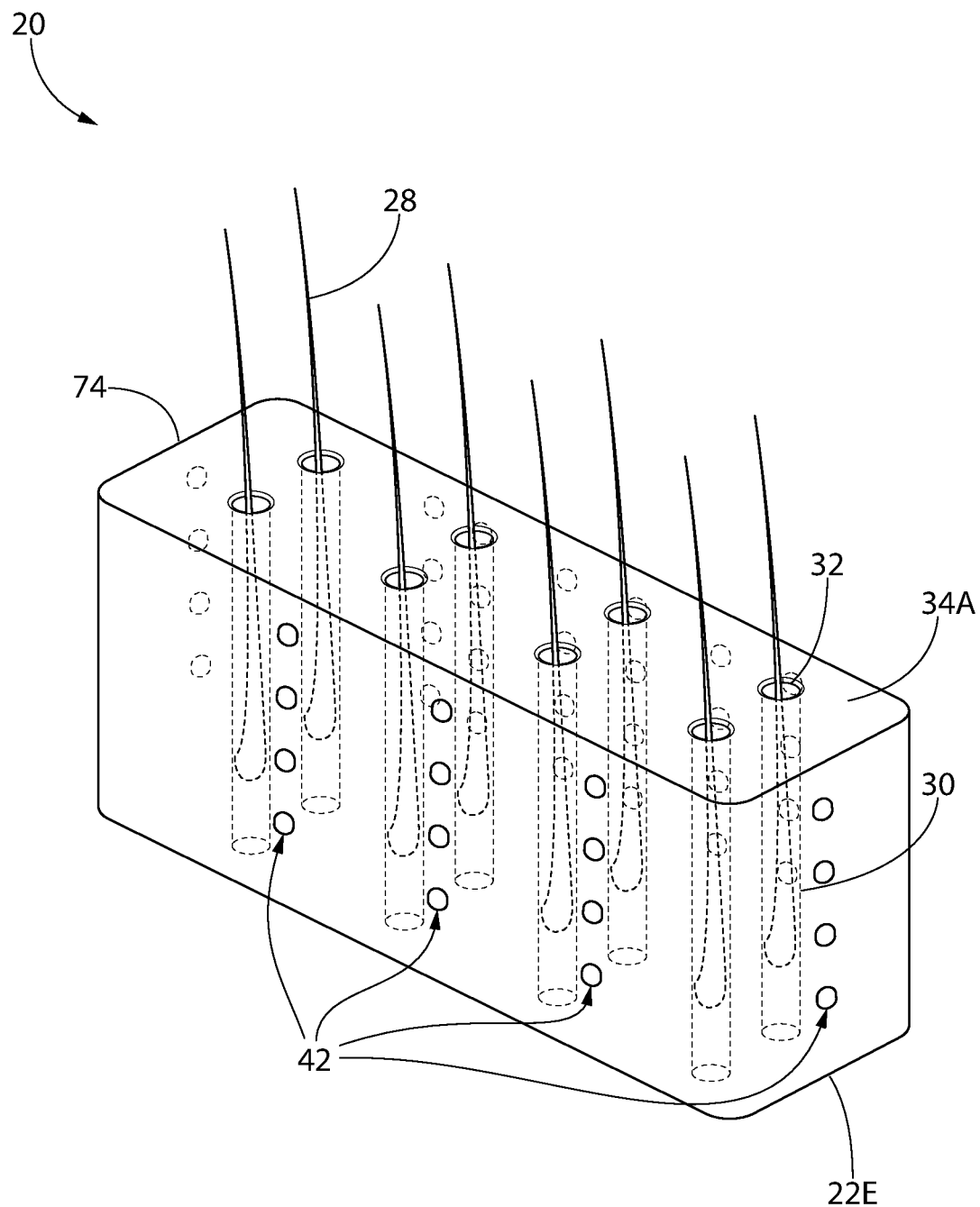
FIG. 28 is a perspective view of another embodiment of an implant anchor of the invention, having a "bar-like" configuration.

FIG. 28 depicts a further embodiment of the implant anchor 20 utilizing a horizontal anchor body 74 having a bar-shaped anchor 22E configuration, with multiple distal orifices 32 arranged in a grid-like pattern on the upper surface 34A of the bar-like configuration that forms the distal end of the implant anchor. In particular, each distal orifice is an opening to an internal hair chamber 30 that contains a hair 28. Four closed tunnels 42 are located between each pair of adjacent hair chambers 30. Thus, twelve parallel closed tunnels 42 run through the full width of the anchor between hair chamber chambers 30 and four parallel closed tunnels 42 run through the full length of the anchor between hair chambers 30.

Figure 29:
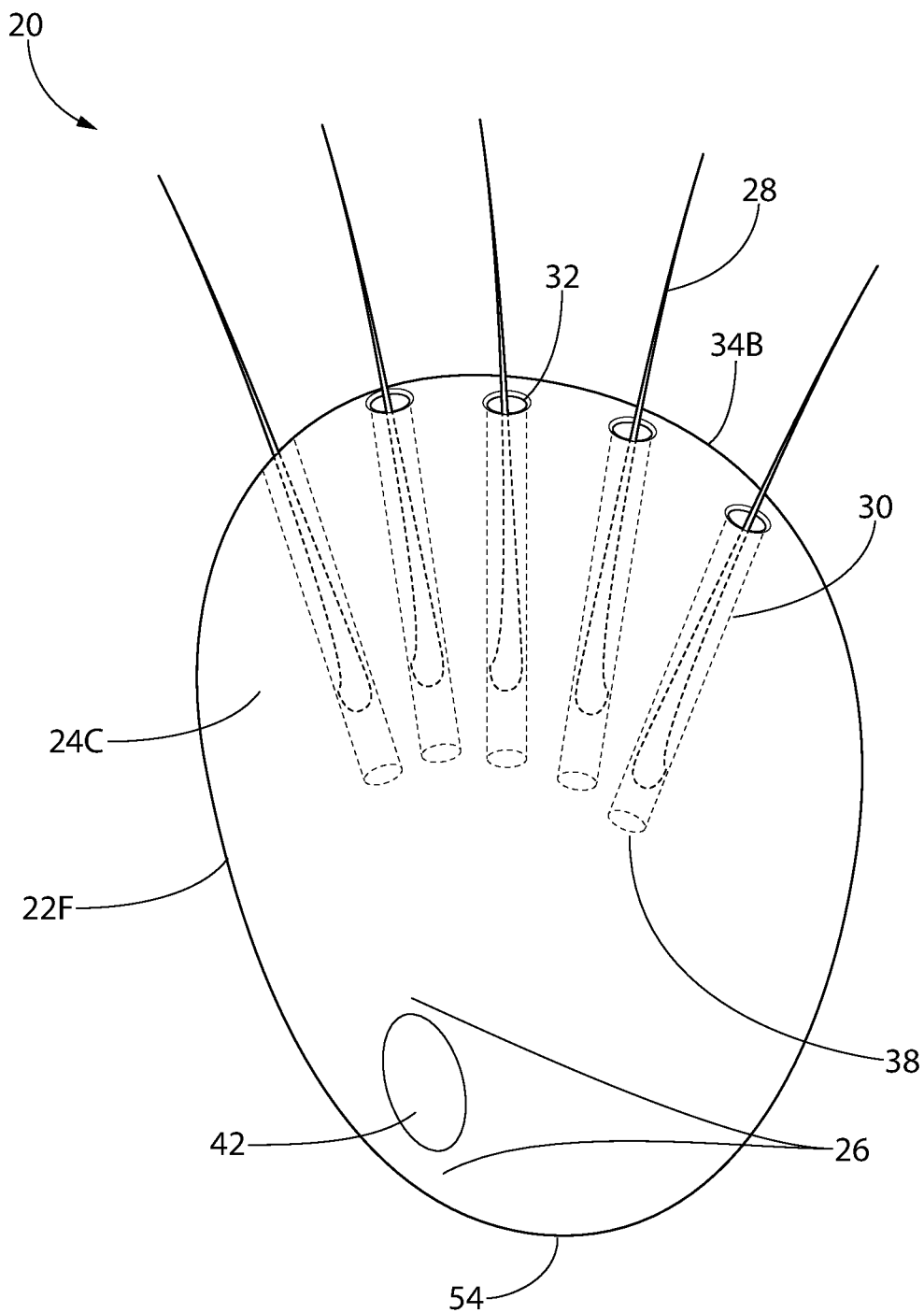
FIG. 29 is a front view of another embodiment of an implant anchor of the invention, having an ovoid or egg-shaped configuration.

FIG. 29 depicts a further embodiment of the implant anchor 20 having an irregular spherical configuration or ovoid configuration 22F and utilizing a plurality of internal hair chambers 30, each containing one hair 28 that emerges from a distal orifice 32 on the curved distal surface 34B of the anchor 22. More particularly, the anchor body 24C is ovoid or egg-shaped, with the curved distal surface 34B of the anchor being wider than the proximal bulbous shape 54. A closed tunnel 42 is located below proximal closures 38 of the internal hair chambers 30 and is centrally aligned on the anchor body.

In accordance with all other anchor embodiments, the anchor embodiments described in FIGS. 28-29 comprise similar materials and utilize tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 30:
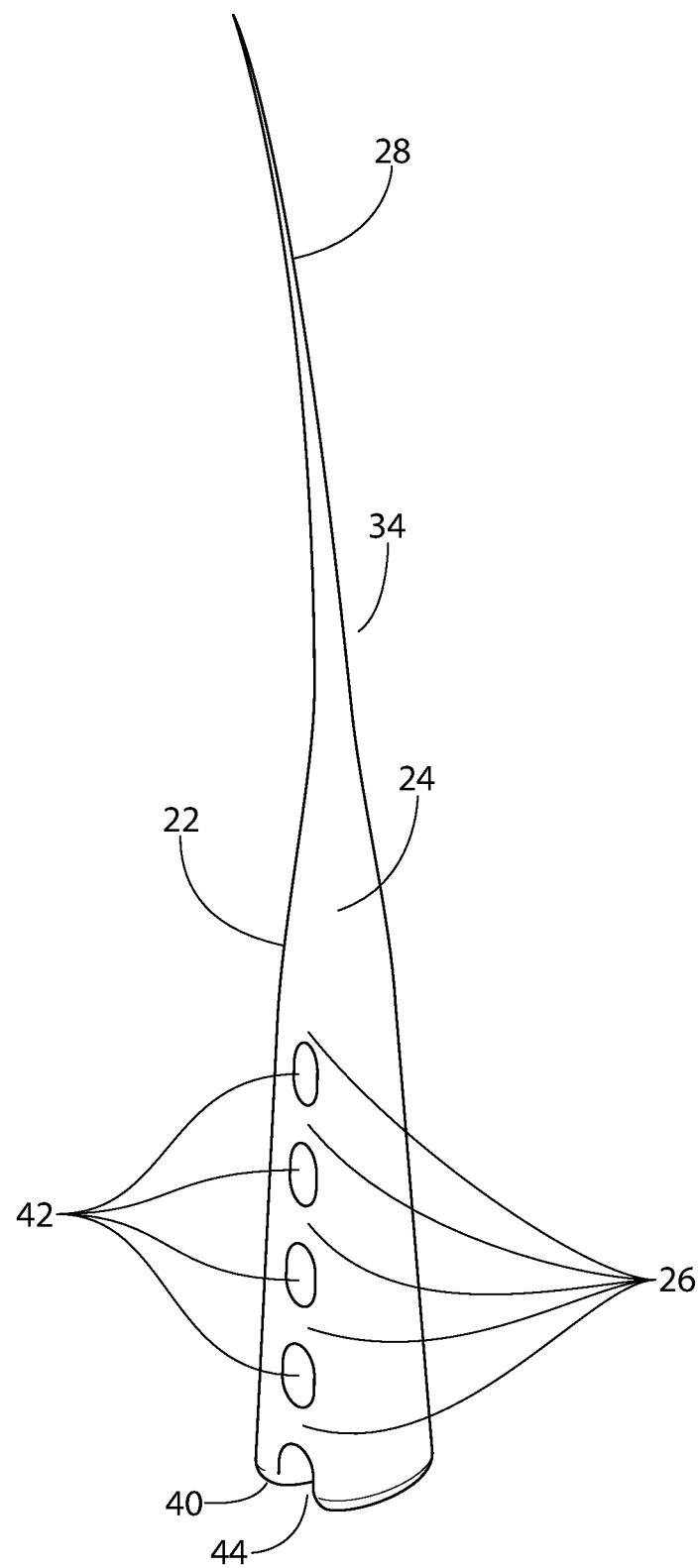
FIG. 30 is a front view of an embodiment of a unitary implant of the invention, wherein the hair element and the anchor body are formed from the same material.

FIG. 30 depicts an embodiment of a complete one-piece hair implant unit in which the hair 28 forms the unit's distal end 34. More particularly, the hair element 28 is formed from the same material as the anchor body 24 itself. The anchor body 24 comprises a distal end 34 and a proximal end 40. The anchor possesses a plurality of parallel closed tunnels 42, each separated by a bridge 26 and vertically aligned along a central portion of the anchor body 24. An open tunnel 44 is centrally aligned on the proximal end.

Figure 31:
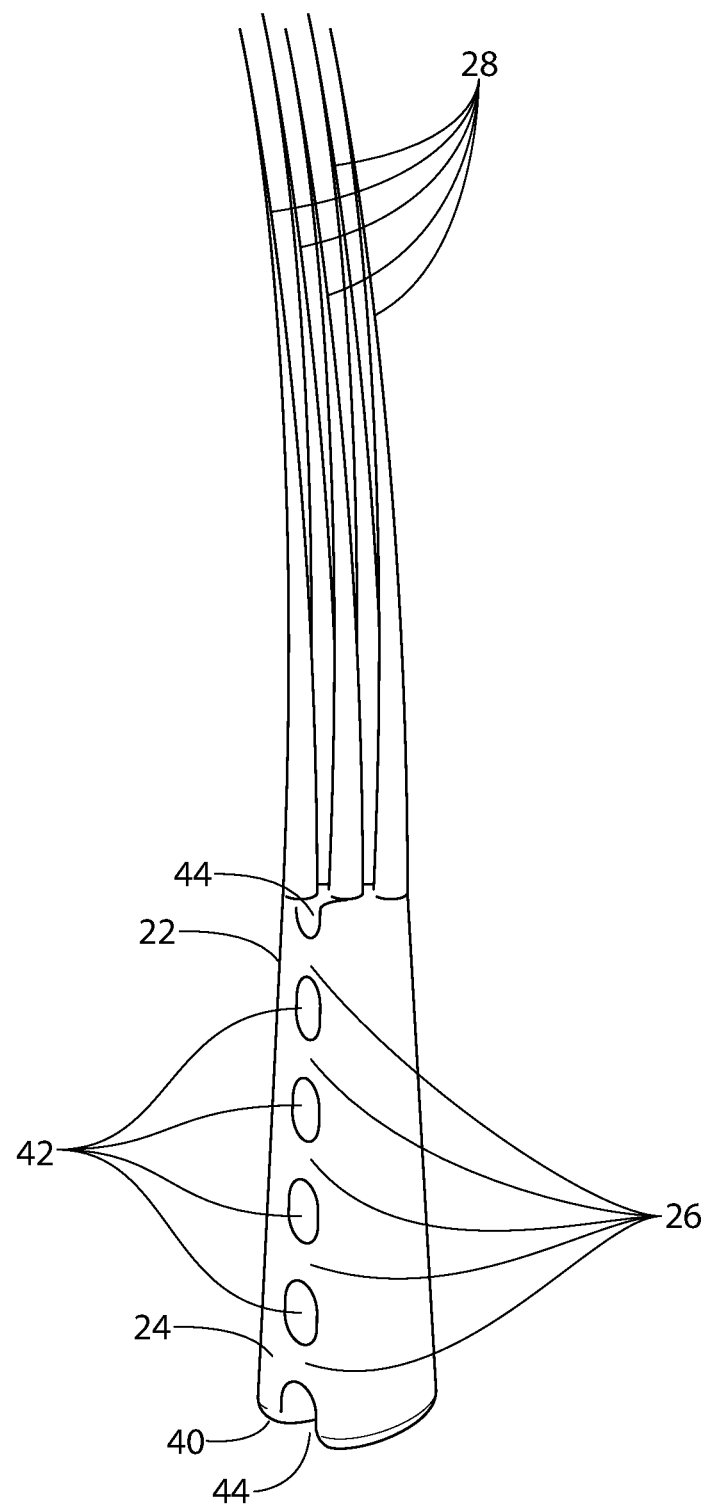
FIG. 31 is a front view of another embodiment of a unitary implant of the invention wherein the hair elements and the anchor body are formed from the same material.

FIG. 31 depicts a further embodiment of a complete one-piece hair implant unit in which a plurality of hairs 28 are formed at the distal end 34 of the anchor 22 from the body 24 itself. An open tunnel 44 is centrally aligned on both the distal end and the proximal end 40. Additionally, a plurality of parallel closed tunnels 42, each separated by a bridge 26, is vertically aligned along a central portion of the anchor body 24.

Figure 32:
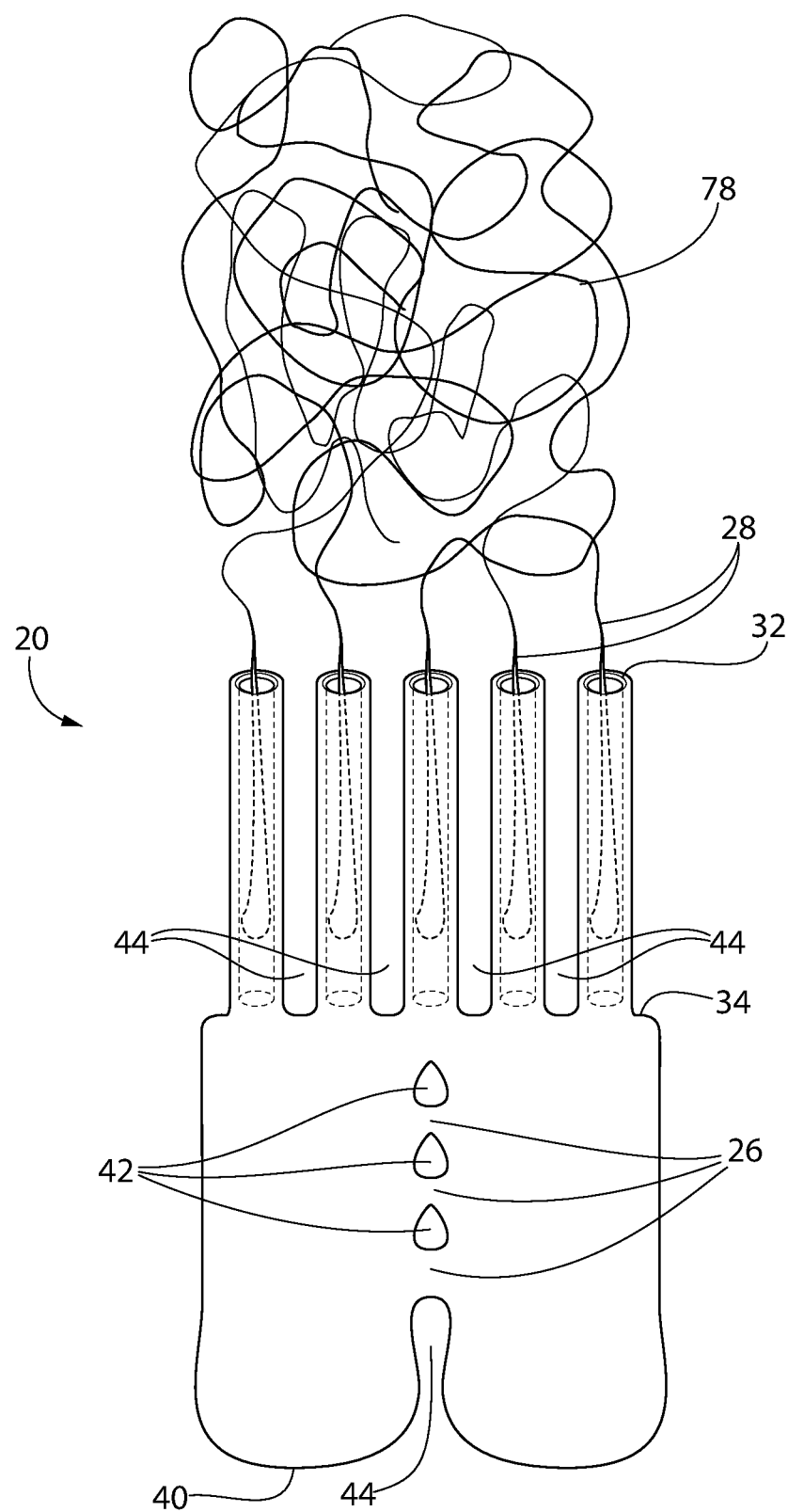
FIG. 32 is a front view of another embodiment of an implant of the invention wherein the plurality of hair elements forms or attaches to a styled hair bundle construction.

FIG. 32 depicts an embodiment of an implant of the invention wherein the anchor 20 comprises a plurality of distal orifices 32 with open tunnels 44 between each distal orifice. Each distal orifice comprises a hair element 28 that emerges from the anchor. In certain embodiments, the hair elements are arranged into a hair bundle construction 78. In other embodiments, the hair elements are attached to an independently one or more hairs woven, braided, twisted, rolled, wrapped or otherwise constructed through mechanical or chemical means. The hair bundle construction may take on a form that includes but is not limited to a dreadlock, braid, twist, roll, or interlocking hair formation.

In accordance with all other anchor embodiments, the anchor embodiment described in FIG. 32 comprises similar materials and utilize tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

Figure 33:
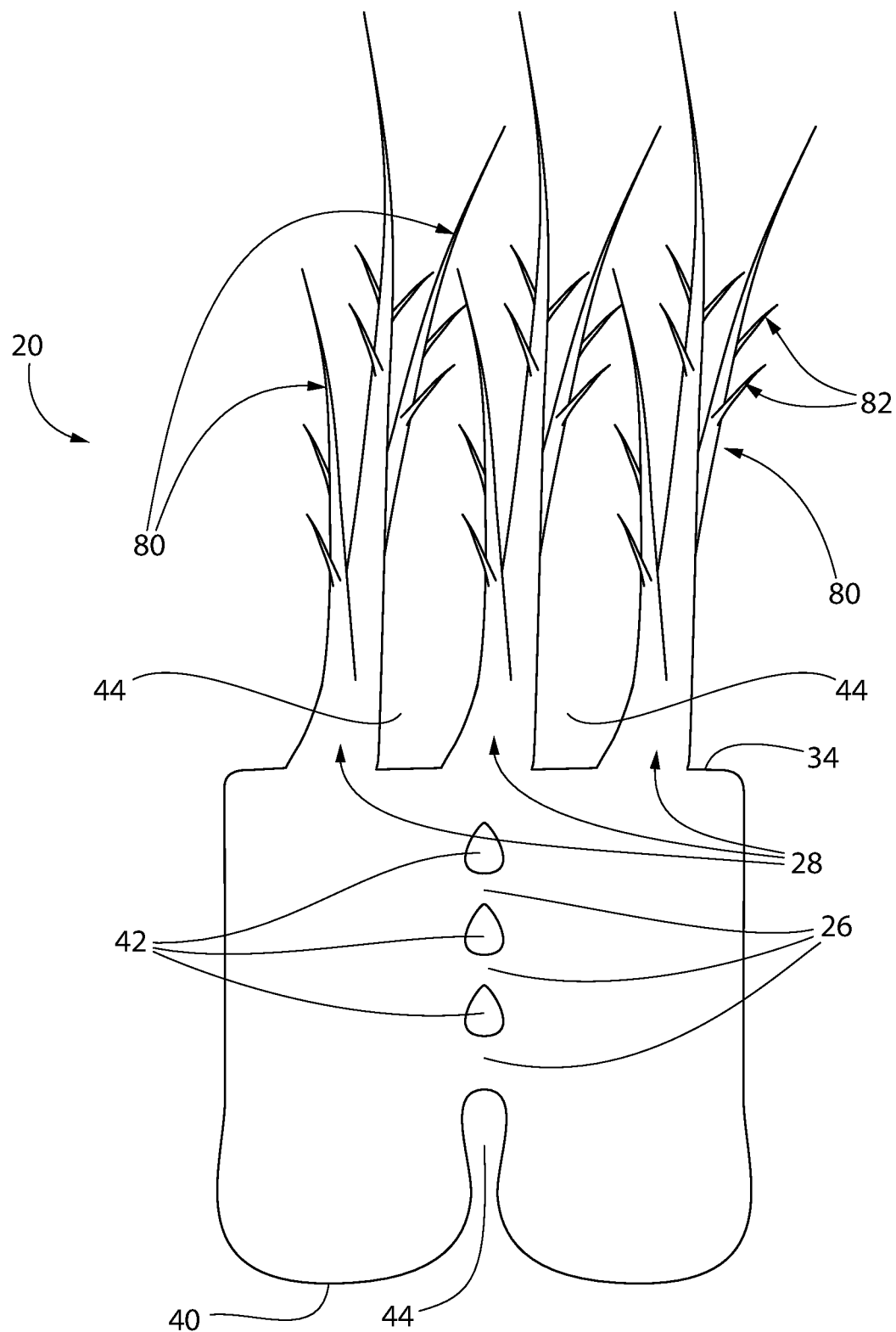
FIG. 33 is a front view of another embodiment of a unitary implant of the invention wherein ancillary hair elements and optional hair bud structures emerge from the sides of the primary hair elements.

FIG. 33 depicts a further embodiment of a one-piece (or unitary) hair implant of the invention wherein the anchor 20 comprises a plurality of primary hair elements 28 extending from the distal end 34 of the implant. Each primary hair element is a branched hair containing at least one ancillary hair element 80. The ancillary hair element stems off of the side or trunk of the primary hair element and is attached in a permanent fashion, allowing the primary and ancillary hair elements to be molded together as one unit. In certain embodiments, each primary hair element, in addition to containing at least one permanent ancillary hair element, may also contain at least one hair bud structure 82. The hair bud structures emerge from the sides or trunks of the primary and/or secondary (i.e., "emergent") hair elements and serve as points of attachment in which additional ancillary hair elements may be added and removed as desired.

In accordance with all other anchor embodiments, the anchor embodiments described in FIGS. 30-31 and 33 comprise similar materials and utilize tunnels for supporting collagen ligature growth after subcutaneous implantation to receive and retain collagen ligatures that are capable of anchoring the hair strand anchor to a hair implant recipient. As is the case with all other implant anchor embodiments having tunnels, the open and/or closed tunnels can also define a fracture line as discussed above.

It is preferred to form such unitary hair implants from materials that simulate human hair. Such materials are preferably capable of forming synthetic hairs having the texture, flexibility, color and dimensions that are the same as or substantially similar to those of human hair.

Although the hair portion and the anchor portion of the unitary hair implants are preferably formed from the same material(s), it is within the scope of the invention to modify different portions of the unitary hair implants differently so as to provide different properties to different portions of the implant. For example, dyes and/or pigments can be selectively applied to change the color of the hair portion of the implant, and crosslinking agents can be applied to selectively change the mechanical properties of desired portions of the implant.

It is also within the scope of the invention to form different portions of the unitary hair implants from different materials where the materials bond together to provide a substantially seamless connection between the hair portion and the anchor portion of the implant.

Preferred materials for use in preparing the unitary hair implant embodiments of the invention include those materials suitable for use in other anchor and hair embodiments discussed herein.

Non-unitary embodiments of the invention described and shown in the drawings can also be provided in alternative unitary embodiments.

As noted above, the tunnels and protrusions of the anchor help anchor the implant within recipient by supporting collagen ligature growth associated with the foreign body reaction. The protrusions also provide mechanical resistance to removal.

The foreign body reaction discussed above also provides protection from bacteria. This collagen envelope or wall will prevent bacteria, which may have migrated beyond the distal implant zone, from entering the dermal or subcutaneous space of the skin.

When the foreign body reaction has completed the collagen envelope, there will be a contraction effect over time. This contraction is favorable because it will tighten the grip of the collagen envelope on the implant and further limit any gap formation between the implant and living skin and thus prevent bacterial entrance.

The direct contact between the implant and living skin tissue, called the interface, is a bond created by a biochemical reaction. This bonding force will also help with the attachment of the implant to the surrounding skin, and thus assist in preventing a corridor for bacterial entrance.

Patient scalp cleanliness is also an important aspect. Keeping the bacterial load or quantity low on the scalp skin, or wherever the implants are placed will be beneficial in preventing infection.

Another important aspect is the prevention of not only infection but inflammation, not caused by microorganisms. Inflammation is a reaction to the foreign materials placed into the skin, such as the hair and the silicone rubber component of the hair implant. This inflammatory reaction will naturally occur when the hair implant is placed, however, it is important to design the implant to yield a self-limiting inflammatory and immune system resulting in chemical and physical changes, and this includes hair implants as well. Hair implant oxidation, erosion, fracture and more importantly subsequent implant fragment retention must be considered potential hazards of implantation and thus it is preferred to include in the inventive hair implant safety features designed to deal with these hazards. If oxidation and erosion of the implant were to occur to a significant degree fragmentation of the implant may occur. It is preferable to anticipate this occurrence by including in unitary and non-unitary embodiments of the inventive hair implant a fracture line to facilitate a safe conclusion to the potential fragmentation and the retention of the fragment. The fracture line is a feature of the implant having reduced resistance to fracturing relative to the balance of the implant, such that if there is fragmentation it occurs along the fracture line. FIG. 1 shows an example of a fracture line 24 colinear with a line of tunnels 26. This planned vertical (or longitudinal) fracture line can facilitate the release of the implant from collagen ligatures through tunnels 26, thus allowing for an easier release of the now two vertical fragments of the fractured implant. Each fragment will contain at least one hair and silicone structure. The fracture line prevents or at least minimizes the likelihood of the formation of random fragments that cannot be removed from the scalp by pulling on hair. The fracture line predisposes the implant to splitting into two fragments. If fracturing occurs, it is easier for the hair implant to fall out since it has lost one of its key anchoring mechanisms. Minimal pulling forces will allow the fractured implant to be completely removed. This safety feature will drastically reduce or eliminate any retained fragments of hair, or portions of the implant which, in turn, reduces or eliminates any acute or chronic inflammatory reactions. If the implant has been totally released, or pulled out, the subsequent collagen envelop will dissolve over time, and the subcutaneous architecture will be remodeled. Also, after the implant has been placed into position, and the foreign body reaction completed with a collagen envelope around the structure, if a fragment were to be retained, the collagen envelope structure would provide continued protection and serve its function by surrounding the foreign body and protecting it from the immune system. If an inflammatory reaction were to occur, the body would attempt to discharge this retained fragment. This reaction would be limited to the very superficial skin surface (as opposed to the deep-rooted designs of current hair implants deep in the galea aponeurotica, with no escape or discharge mechanism), involving the epidermal and dermal layers. The more superficial inflammation will most likely result in the formation of a pimple type structure with the subsequent discharge of pus and the fragments, not unlike the typical pimple formation found in certain conditions such as acne.

Implantation Technique

Introduction

The preferred implantation technique involves several steps including pre-treatment with antibiotics and anti-inflammatories, recipient skin site preparation, anesthesia, recipient site formation, hair implant selection and placement, temporary hair implant stabilization and skin closure by medical glue, artistic concerns, and post procedure care with antibiotics, corticosteroids, and instruction regarding the proper cleansing of the scalp.

Natural Look of Hair Exiting the Scalp

The administration of antibiotics and anti-inflammatory medications and recipient site anti-bacterial preparation are very important first steps in the process. Considering that potentially thousands of hair implants will be placed, with the corresponding thousands of needle pokes into the skin, it is prudent to begin medical therapy to prevent infection and a hyperinflammatory response. Infection or a hyperinflammatory reaction may result in skin surface or epidermal and/or dermal skin damage. This damage may translate into a pitting effect, or visible indentations where the recipient site and subsequent hair implant were placed. This type of imperfection will draw attention to the scalp, especially under certain lighting which will accentuate this pitting look.

Recipient skin site preparation involves washing the designated skin area with soap and water, then betadine or an acceptable surgical cleansing solution is applied, then, after the cleansing solution dries, it is wiped off with sterile alcohol. This sequence of skin cleansing, with the appropriate donning of staff in addition to having the treatment room air purity level at an ISO 4 or 5, will eliminate or significantly reduce any bacteria or spores in the field of operation.

Recipient site formation is another critical step not only to form a hole for the hair implant, but to minimize the actual puncture (e.g., by an appropriately sized needle) or cut size (e.g., by an appropriately sized scalpel) which will minimize the healing needed and potential visible signs of skin pitting. In addition, the site formed needs to parallel the natural angle that hair would normally exit. This will allow for the hair to fall naturally forward, to the side or back according to the patient's natural angulation and thus natural hair style look. The actual process of recipient site formation involves a very similar technique currently used in surgical hair transplant procedures. The recipient site formation technique involves using a 22-32-gauge sterile needle, a size 11 or 15 blade or similar instrument. The needle is used to poke the scalp at a very specific angle and depth, depending on what hair pattern and density is desired. For example, if the patient desires to fill in the scalp crown area with hair implants, it will be observed that a 'whirl' pattern naturally exists there. Considering this, the needle used to poke the skin in this scalp area will need to emulate this type of 'whirl' pattern. This is accomplished by poking the needle at an acute angle to the scalp and with a rotating type pattern. Then, when the hair implants are placed in, they will stick out of the scalp in a whirl pattern. The depth of the needle poke needs to approximate the normal follicular depth of 6 mm (in this case of scalp hair placement). If eyebrow hair is going to be placed in, the needle pokes need to be more superficial, about 3-4 mm deep, etc. Lastly, the needle poke incisions will be placed as close together as possible. Considering that an inflammatory reaction is a normal response to a needle poke and foreign body reaction to the silicone tipped hair implant, it is advisable to space out the implants by 3-4 mm, and proceed with subsequent implants in the same manner over 3-4 treatments to ultimately fill in the skin area to the desired density.

Hair implant selection is very important to maintain a natural look. For example, the hairline on the scalp has thinner hair fiber diameters than hairs just 1.25 cm behind it. This transition of finer to more coarse hair is common and is what is natural. The selection of thinner fiber diameter hairs will need to be selected for the hairline areas to mimic the natural.

The silicone tipped portion of the hair implant is surgically placed with an approximate depth of 3-6 mm under the skin depending on whether scalp, pubic, or other body hair is being restored. This silicone tipped portion of the hair will not impair the natural look of the hair implant because the clear type of silicone used will be invisible to the eye and will remain mostly under the skin, with a small 0.1 to 0.5 mm segment remaining above the skin (or below in certain embodiments), keeping it out of view.

Hair Implant Placement

Appropriate anesthesia allows for the proper placement of the hair implants with the proper depth placement. Anesthesia involves the application of a topical cream lidocaine type anesthetic on the recipient site, or area of skin that will receive the hair implants. After 30 minutes of topical anesthetic application, the area is cleaned and then an injectable form of tumescent lidocaine anesthetic solution is administered in a field block manner. The anesthetic cream is administered after the area is cleaned with soap and water, then the anesthetic is removed, wiped down with sterile alcohol, then the area is injected with a tumescent solution of lidocaine, then the betadine or other type solution is administered, etc.

In those embodiments wherein the hair is added to the anchor at a physician's office, at a hair implantation clinic, or at a manufacturer with or without an automated process, the hair implant placement first involves opening a sterile pack of either the anchor portion of the implant only, which will need subsequent attachment of the hair component, or the anchor portion with the hair already attached. If the sterile pack only has the anchor component, then the pack will be opened at the physician's office or clinic, and the anchors will be placed onto a sterile tray. Hair components are then added to the anchors. There are several methods of hair to anchor attachment with several exemplary embodiments discussed below.

After the hair has been attached to the anchor it is ready for placement into the skin. A fine jeweler type sterile tweezer can be used to pick up the hair implant by the silicone tipped area and insert it into the recipient site hole made by the needle. After all of the hair implants have been placed into position, the technician places a tiny drop of medical adhesive (e.g., cyanoacrylate or another fast drying medical glue) to immediately stabilize the hair implant. This technique, with the fine instruments used, will minimize trauma and heal better and result in a more natural skin surface.

Hair Density and Hair Pattern

The hair implant technique, using very close recipient site placement, recipient site with appropriate angulation, the use of delicate jeweler's forceps, and a glue down technique to stabilize the hair implant, will allow for high dense packing and appropriate hair pattern.

Providing close approximation of recipient sites, with very small needle cuts to puncture the scalp, will allow for more density per hair implant session. The angle by which the recipient site is made is critical to the hair pattern formed. For example, if one wants to have a natural whirl pattern on the crown of the scalp, a very deliberate rotating angulation pattern will need to be prepared to emulate a natural hair pattern.

The use of fine and delicate jeweler's forceps is important in the handling and proper placement of the hair implant itself. The jeweler's forceps allows for a gentle hold on the implant, preventing damage, and allows an unobstructed view of the placement of the implant into the scalp, due to the forceps holding only a small portion of the distal portion of the implant without obstructing a direct view of the proximal end of the implant for easy placement into the recipient site.

The final glue down of the hair implant will immediately stabilize and temporarily anchor the implant and prevent premature pull out. Since the foreign body reaction and anchoring of the hair implant takes 14-21 days, this temporary anchoring mechanism will prevent hair fall out and a reduction in hair density.

Figure 8:
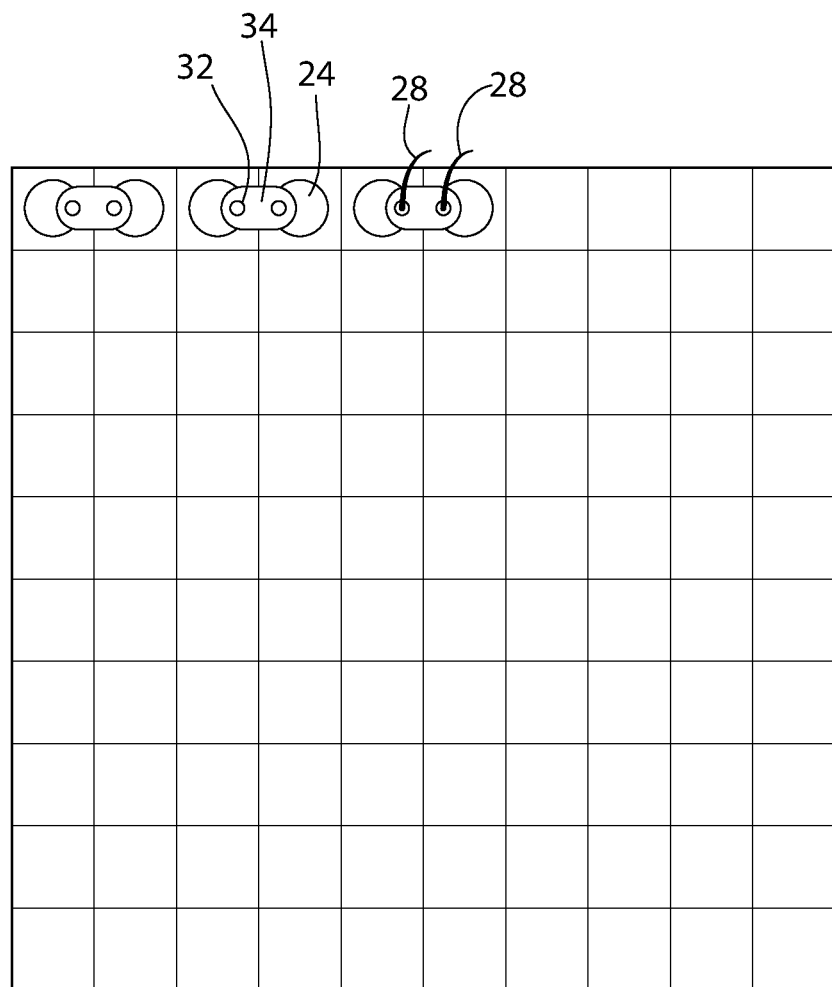
FIG. 8 is a top schematic view of an embodiment of the invention wherein implants are placed in the scalp of a patient in a regular spaced apart manner defined by a grid.

FIG. 8 is schematic top view of a plan for the placement in the scalp of implants 20 comprising vertical components 24, distal ends 34, distal orifices 32 and hairs 28. Overlaying the scalp is a 10×10 grid wherein each cell of the grid represents a 1 mm×1 mm area of the scalp. Each implant 20 occupies two cells in the embodiment of FIG. 8. Completion of this placement scheme would result in fifty implants (or follicular units) per $cm^2$, or one-hundred hairs per $cm^2$ when the follicular units have two hairs each.

Anchoring of the Hair Implant

The recipient site, being a surgical step by poking a needle into the skin, is the key method of allowing the hair implant access and approximation to the living tissue and the very important immune system reaction. This hair implant and skin issue approximation will allow for the foreign body reaction and all the anchoring effects to occur (see the anchoring section above).

The final glue down of the hair implant will immediately stabilize and temporarily anchor the implant and prevent premature pull out. Since the foreign body reaction and anchoring of the hair implant takes 14-21 days, this temporary anchoring mechanism will prevent hair fall out.

Protecting the Hair Implant from the Immune System

The recipient site, being a surgical step by poking a needle into the skin, is the key method of allowing the hair implant access and approximation to the living tissue and the very important immune system reaction. This hair implant and skin tissue approximation will allow for the foreign body reaction to take place and form the collagen envelope. After the collagen envelope has completely formed, the foreign body reaction has completed its objective to protect the body by entombing the "foreign body" with this thick collagen shell and will then terminate the immune system reaction. This collagen shell provides dual protection, protecting the implant from further immune system reactions, and protects the body from the implant harming the body (foreign body reaction assumes the foreign body is dangerous and thus walls it off to protect the body).

Hair Implant Safety Features

With appropriate antiseptic cleansing of the skin, utilizing sterile instruments for anesthesia, recipient site formation, and hair implant placement, hair implant stabilization, and immediate glue sealing of the epidermal incision site, will limit bacterial entrance in the short term. Long term safety features of forming a bacterial barrier, anchoring, and fracture and fragment retention issues are discussed above.

This implantation technique will allow for complete removal in certain embodiments, if desired. The hair implant is placed into the scalp as deeply as natural hair fibers are in the scalp, about 5-6 millimeters deep (only into the subcutaneous/dermal areas where normal natural hair resides). The term "subcutaneous" as used herein is defined in its broadest sense as encompassing the epidermal, intradermal, and subcutaneous spaces, including adipose tissue. If the hair implant needs to be removed, this can be done by a simple plucking motion (like plucking out normal hair). So to remove the hair is a safety factor just in case there is a follicle that becomes infected. It is normal for natural hair follicles to sometimes become infected, so it follows that the same risk applies to the inventive hair implant.

Infection and inflammation of hair bearing skin is not uncommon. Many people naturally develop low level folliculitis or inflammation of the hair follicles. This can be due to a multitude of causes including bacterial and non-bacterial sources, ingrown hairs, poor hygiene, hair fall out and regrowth, etc. Some other causes of infection and inflammation are from simple shaving, others from hormonal issues, or even from the natural bacteria found in the hair follicular and skin areas. Even though infection and inflammation is found naturally, and typically at minor levels, the goal of hair implantation is to improve upon what is observed as the natural occurrence of hair bearing skin infections and inflammation.

It is projected that the incidence of skin infections and inflammation associated with the inventive implants will be less than that found naturally. The lack of glandular organs and their secretions will make the implant area less conducive to bacterial growth. In addition, the anchor of the invention has no hormone receptors to trigger an inflammatory response, unlike natural hair follicles.

Manufacturing of Implants

The anchor of the inventive implant can be formed by a variety of different processes, including by injection molding and 3-D printing. The anchor preferably comprises a material selected for certain characteristics such as the appropriate durometer, molecular weight, crosslinking, and strength. These characteristics will not only help provide the appropriate strength to withstand oxidation and fracturing, but will easily withstand the pressure forces of the tweezer implantation technique. This aspect of tweezer placement is significant mainly in hair transplant surgery when working with live hair follicular units. Tweezer placement can traumatize and crush living hair follicles, but in the case of hair implants that, of course, is not a risk.

Materials highly resistant to long term chemical interaction with the immune system are preferred. High implant strength longevity is desirable. If the hair is physically pulled out the goal is for the entire implant unit to be ejected in one or two parts, thus preventing breakage (other than at the fracture line) and remnants of the implant to remain under the skin.

Medical grade silicone is the most preferred material for forming the anchor. Other materials suitable for use in forming the anchor include but are not limited to metals (including but not limited to precious metals, metalloids, and other metals), biocompatible polymers (including but not limited to silicones, silicone elastomers, acrylic and other resins, plastics, polyethylene, PTFE, polyesters, PVC, PMMA, hydrogels, etc.), ceramics (including but not limited to silicates, glass, porcelains, carbons, etc.), natural biomaterials (including bone, calcium phosphate based, etc.), and any combination thereof (defined herein as composites).

In a preferred embodiment, implantable medical grade silicone is used for implant production. The silicone material is typically in a liquid form and in two parts. Upon mixing the two parts, part A and part B, a chemical reaction will occur and cause a silicone rubber to be formed. This liquid to solid reaction can be controlled by keeping the mixture cold to slow down the liquid to solid reaction and allow time to inject the liquid silicone into the mold. After being injected into the mold, heat is applied to complete the liquid to solid formation reaction.

The mold preferably comprises a multitude of cavities for receiving the liquid to be solidified to form the anchors of the implants. The number of cavities is not particularly limited, and in certain embodiments can range from 1 or 10 or 100 or 1,000 or 10,000 cavities to 10 or 100 or 1,000 or 10,000 or 100,000 cavities per mold.

The dimensions of a cavity are dictated by the desired dimensions of the resulting implant. In certain embodiments, the cavities are 1-10 mm or 3-9 mm or 5-7 mm or 6 mm deep with a maximum diameter of 0.2-1.2 mm or 0.4-1.0 mm or 0.6-0.8 mm or 7.0 mm.

The fluid in the cavities should preferably be free of air bubbles, voids and the like. In certain embodiments, the anchor mold comprises two plates which are used in a process that minimizes or avoids air bubbles—a first plate having a plurality of holes through it and a second plate that closes off the holes in the first plate. The two plates are immersed in silicone liquid with the second plate being used to force the silicone liquid through the holes in the first plate (like a plunger on a syringe) until the two plates are in contact with each other. The excess silicone fluid is then scraped off the surface of the first plate to provide a mold having a plurality of cavities filled with substantially bubble-free liquid silicone.

In unitary hair implants of the invention, hair strands are formed with or as a portion of the anchor body using, e.g., molds including anchor body and hair and/or by drawing filaments from the anchor body while it is still in an uncured state.

In non-unitary embodiments, the strands of hair to be inserted in the anchors are preferably pre-coated with silicone (or other bonding agent or primer compatible with silicone, such as alkoxy silane monomers or polymers as taught by U.S. Pat. No. 5,061,284 (117)) to a length of, e.g., 2-10 mm or 6-8 mm or 7 mm and then allowed to form a solid. The length of this coating applied to the hair strands is preferably selected to be 1 mm longer than the depth of the anchors in which the hair strands will be placed, such that the coating extends 1 mm above the anchor and remains external to the surface of the epidermis after implantation. In other embodiments, the length of the coating is 0.1 or 0.5 mm to 1.5 or 2 mm longer than the anchor depth.

After the hair strand coating has dried to form a solid, the hair strands are placed into the silicone liquid filled mold cavities. Each mold cavity can receive 1, 2, 3, 4 or more hair strands. The mold is then heated to solidify the silicone to form implants having one or more hairs each. The implants are then removed from the mold, sterilized and packaged for distribution and use.

In certain embodiments, the hair will be inserted and then anchored by several potential mechanisms.

In a preferred embodiment of a distal to proximal insertion method, glue is applied to approximately 6 mm of the proximal end of the hair and is then fed into the distal orifice of the internal hair chamber until it reaches the proximal closure of the internal hair chamber.

In a first preferred embodiment of a proximal to distal insertion method, the hair will not be glued first but will first be inserted into the proximal orifice of the vertical component hair chamber, then the hair is pushed through until only 6 mm of the proximal end is visible, then glue is added to this 6 mm end, and finally the hair is continued to be pulled through until completely in the hair chamber.

In a second preferred embodiment of a proximal to distal insertion method, the hair will not be glued first but will first be knotted at its proximal end, and then fed into the proximal opening of the knot chamber until only about 6 mm of the proximal end of the hair is visible. Glue is then applied to this 6 mm end (which will contain the knots), and then the hair is continued to be fed through the hair chamber until reaches the most distal end of the knot chamber.

It is preferred that the hair chamber opening through which the hair will be inserted have a conical shape so as to facilitate hair insertion by the technician (or if automated, by a machine) and to allow a greater amount of glue to remain at that location for increased adhesion.

The knot chamber is an enlarged proximal end of the hair chamber configured to receive the knotted hair portion which has a greater diameter than the unknotted portion of the hair shaft. The hair chamber distal to the knot chamber has a narrower diameter than the knot chamber such that the knotted hair is too wide to leave the knot chamber and enter the hair chamber. The diameter of the knot chamber is preferably 500-600 microns, and the length of the knot chamber is preferably from 500 microns to 6 mm.

In certain embodiments, the vertical component will have a proximal outer surface end which will be rounded. The arc will be 180 degrees, and the circle diameter will be 500 microns to 2 mm. If there is an oval shape, the largest dimensions of the oval will be the same.

It is preferred that at least some and more preferably all edges of the anchor are rounded. This includes the embodiments depicted in the figures.

There are many types of hairs on the body including scalp, facial, eyebrow, arm and leg, pubic, eyelash, etc., and the manufacturing process can be modified to produce the appropriate hair implants for the skin area in question. Thus, for example, eyebrow hair implants will be smaller than scalp hair implants.

In an alternative embodiment, final assembly of hair implants is performed by the end user (physician, physician's assistant, hair technician, etc.). Sterile anchors are supplied to the user, who selects appropriate hair for a given patient and procedure and bonds the hair to the anchors prior to implantation, using, e.g., an adhesive suitable for bonding hair (or synthetic hair) to the anchor material. Suitable adhesives included but are not limited to cyanoacrylates.

As discussed above, the exit angle of hair strands from the anchor is preferably varied for different implantation locations. Thus, the placement of hair strands in the mold cavities can be varied to provide implants with hair exit angles ranging from 1–90°. It is also possible to use curved, angled or otherwise non-linear hair strands in the manufacturing process to achieve the same or similar effect. Thus, for example, a hair stand having a 100° angle 5 mm from its proximal end can be inserted in a 6 mm deep mold cavity such that the hair strand exits the resulting anchor at a 10° angle to the surface.

While the invention has been described in detail and with reference to specific examples thereof, it will be apparent to one skilled in the art that various changes and modifications can be made therein without departing from the spirit and scope thereof.

REFERENCES CITED (1) MEDLINEPLUS (2017). Hair loss. Medical Encyclopedia. MedlinePlus. https://medlineplus.gov/ency/article/003246.htm.

(2) INTERNATIONAL SOCIETY OF HAIR RESTORATION SURGERY (2003). Psychological effects of hair loss in women. http://www.ishrs.org/articles/hair-loss-effects.htm.

(3) KARAMAN et al. (2006). Androgenetic alopecia: Does its presence change our perceptions?. International journal of dermatology, 45(5), 565-568.

(4) BERNSTEIN, R. (2009) Psychological aspects of balding. https://www.bernsteinmedical.com/hair-loss/faq-myths-more/psychological-aspects-of-balding/.

(5) CASH, T. F. (1992). The psychological effects of androgenetic alopecia in men. Journal of the American Academy of Dermatology, 26(6), 926-931.

(6) MAPES, D. (2008). The fallout of hair loss: Suffering in silence. Skin and beauty. NBC News. http://www.nbcnews.com/id/26895411/ns/health-skin_and_beauty/t/fallout-hair-loss-suffering-silence/#.WaWCdMmYbF5.

(7) MEDLINE PLUS (2017). Hair loss. https://medlineplus.gov/hairloss.html.

(8) COCHRANE DATABASE OF SYSTEMATIC REVIEWS: PLAIN LANGUAGE SUMMARIES (2016). Treatments for female pattern hair loss. Plain Language Summary of van Zuuren et al. (2016). Interventions for female pattern hair loss. Cochrane Database of Systematic Reviews 2016, Issue 5. Art. No.: CD007628, p. 1-2.

(9) COCHRANE DATABASE OF SYSTEMATIC REVIEWS: PLAIN LANGUAGE SUMMARIES (2008). Treatments for alopecia areata. alopecia totalis, and alopecia universalis. Plain Language Summary of Delamere (2008). Interventions for alopecia areata. The Cochrane Library. Art. No.: CD004413. p. 1.

(10) HIRSHBURG et al. (2016). Adverse effects and safety of 5-alpha reductase inhibitors (finasteride, dutasteride): a systematic review. The Journal of clinical and aesthetic dermatology, 9(7), 56-62.

(11) WILT et al. (2008). 5-alpha-reductase inhibitors for prostate cancer prevention (review). Cochrane Database of Systematic Reviews, Issue 2: 1-61.

(12) KAPLAN et al. (2012). A 5-year retrospective analysis of 5α-reductase inhibitors in men with benign prostatic hyperplasia: finasteride has comparable urinary symptom efficacy and prostate volume reduction, but less sexual side effects and breast complications than dutasteride. International journal of clinical practice, 66(11), 1052-1055.

(13) CHELLINI et al. (2015). Generalized hypertrichosis induced by topical Minoxidil in an adult woman. International journal of trichology, 7(4), 182-183.

(14) AKTAS et al. (2016). Could Topical Minoxidil Cause Non-Arteritic Anterior Ischemic Optic Neuropathy?. Journal of clinical and diagnostic research: JCDR, 10(8), WD01: 1-2.

(15) FEDERAL DRUG ADMINISTRATION (2016). Sec. 895.101 Prosthetic Hair Fibers. CFR Title 21, Volume 8, Chapter 1, Subchapter H, Part 895, Subpart B. https://www.accessdata.fda.gov/scripts/cdrh/cfdocs/cfcfr/CFRSearch.cfm?fr=895.101.

(16) LEPAW, M. I. (1980). Therapy and histopathology of complications from synthetic fiber implants for hair replacement: A presentation of one hundred cases. Journal of the American Academy of Dermatology, 3(2), 195-204.

(17) HANKE et al. (1981). Fiber implantation for pattern baldness. Am Acad Dermatol 4(3): 278-283.

(18) HANKE et al. (1981). Hair implant complications. JAMA, 245(13), 1344-1345.

(19) PELUSO et al. (1992). Cutaneous complications of artificial hair implantation: a pathological study. Dermatology, 184(2), 129-132.

(20) NIDO LTD (2006). What's new. http://www.nidohq.co.jp/nido_english/what/what.html.

(21) BIOFIBRE (2015). Results. Biofibre: High Technology Hair Implant System. http://www.biofibre.com/en/results/.

(22) PERRY et al. (2002). Defining pseudofolliculitis barbae in 2001: a review of the literature and current trends. Journal of the American Academy of Dermatology, 46(2), S113-S119.

(23) JASTERZBSKI et al. (2015). Pseudofolliculitis cutis: a vexing disorder of hair growth. British Journal of Dermatology, 172(4), 878-884.

(24) BERNARD, B. A. (2016). Advances in understanding hair growth. F1000Research, 5: 1-8 (FIG. 4).

(25) OH et al. (2016). A guide to studying human hair follicle cycling in vivo. Journal of Investigative Dermatology, 136(1), 34-44.

(26) SHAO et al. (2014). Follicular unit transplantation for the treatment of secondary cicatricial alopecia. Plastic Surgery, 22(4), 249-253.

(27) BARRERA, A. (2005). Reconstructive hair transplantation of the face and scalp. In Seminars in Plastic Surgery 19(2): pp. 159-166.

(28) AVRAM et al. (2014). Side-effects from follicular unit extraction in hair transplantation. Journal of cutaneous and aesthetic surgery, 7(3), 177-179.

(29) KARAÇAL et al. (2012). Necrosis of the donor site after hair restoration with follicular unit extraction (FUE): a case report. Journal of Plastic, Reconstructive & Aesthetic Surgery, 65(4), e87-e89.

(30) POSWAL et al. (2011). When FUE goes wrong!. Indian journal of dermatology, 56(5), 517-519.

(31) TOYOSHIMA et al. (2012). Fully functional hair follicle regeneration

(32) DUVERGER et al. (2014). To grow or not to grow: hair morphogenesis and human genetic hair disorders. Seminars in cell & developmental biology. Vol. 25: pp. 22-33.

(33) TANG, V. W. (2006). Proteomic and bioinformatic analysis of epithelial tight junction reveals an unexpected cluster of synaptic molecules. Biology direct, 1(1), 37: 1-30.

(34) HARTSOCK et al. (2008). Adherens and tight junctions: structure, function and connections to the actin

(35) SCHNEEBERGER et al. (2004). The tight junction: a multifunctional complex. American Journal of Physiology-Cell Physiology, 286(6), C1213-C1228.
(36) GOODING et al. (2004). The cadherin-catenin complex as a focal point of cell adhesion and signalling: new insights from three-dimensional structures. Bioessays, 26(5), 497-511.
(37) SLUYSMANS et al. (2017). The role of apical cell-cell junctions and associated cytoskeleton in mechanotransduction. Biology of the Cell (109): 139-161.
(38) HARTSOCK et al. (2008). Adherens and tight junctions: structure, function and connections to the actin cytoskeleton. Biochimica et Biophysica Acta (BBA)-Biomembranes, 1778(3), 660-669.
(39) SCHARSCHMIDT et al. (2013). What lives on our skin: ecology, genomics and therapeutic opportunities of the skin microbiome. Drug Discovery Today: Disease Mechanisms, 10(3), e83-e89.
(40) KONG et al. (2012). Skin microbiome: looking back to move forward. Journal of Investigative Dermatology, 132(3), 933-939.
(41) GRICE et al. (2011). The skin microbiome. Nature reviews. Microbiology, 9(4), 244-253.
(42) SENGUL et al. (2009). Axillary pilonidal sinus: A case report. North American journal of medical sciences, 1(6), 316-318.
(43) BASCOM, J. (1983). Pilonidal disease: long-term results of follicle removal. Diseases of the colon & rectum, 26(12), 800-807.
(44) BENEDETTO et al. (2005). Pilonidal sinus disease treated by depilation using an 800 nm diode laser and review of the literature. Dermatologic surgery, 31(5), 587-591.
(45) KHANNA et al. (2011). Pilonidal disease. Clinics in colon and rectal surgery, 24(01), 046-053.
(46) MEDLINEPLUS (2017). Pilonidal sinus disease. Medical Encyclopedia. MedlinePlus. https://medlineplus.gov/ency/article/003253.htm.
(47) BARRESE et al. (2016). Scanning electron microscopy of chronically implanted intracortical microelectrode arrays in non-human primates. Journal of neural engineering, 13(2), 026003: 1-44.
(48) LEI et al. (2016). Biofunctionalization of silicone rubber with microgroove-patterned surface and carbon-ion implantation to enhance biocompatibility and reduce capsule formation. International journal of nanomedicine, 11, 5563-5572.
(49) PATEL et al. (2016). Solid implants in facial plastic surgery: potential complications and how to prevent them. Facial Plastic Surgery, 32(05), 520-531.
(50) HINDERER, U. T. (1991). Nasal base, maxillary, and infraorbital implants—alloplastic. Clinics in plastic surgery, 18(1), 87-105.
(51) SHAO et al. (2014). Follicular unit transplantation for the treatment of secondary cicatricial alopecia. Plastic Surgery, 22(4), 249-253.
(52) SINCLAIR et al. (2015). Androgenetic alopecia: new insights into the pathogenesis and mechanism of hair loss. F1000Research, 4(F1000 Faculty Rev): 585: 1-9.
(53) BARRERA, A. (2005). Reconstructive hair transplantation of the face and scalp. In Seminars in Plastic Surgery 19(2): pp. 159-166.
(54) UEBEL, C. O. (2005). The punctiform technique in hair transplantation. Seminars in Plastic Surgery, Vol. 19, No. 02, pp. 109-127
(55) ROSE, P. T. (2015). Hair restoration surgery: challenges and solutions. Clinical, cosmetic and investigational dermatology, 8, 361-370.
(56) JONES et al. (2013). Characterization of X-linked hypohidrotic ectodermal dysplasia (XL-HED) hair and sweat gland phenotypes using phototrichogram analysis and live confocal imaging. American Journal of Medical Genetics Part A, 161(7), 1585-1593.
(57) RAPOSIO et al. (2015). Scalp surgery: quantitative analysis of follicular unit growth. Plastic and Reconstructive Surgery Global Open, 3(10): 1-4.
(58) OTBERG et al., "Variations of hair follicle size and distribution in different body sites." Journal of Investigative Dermatology 122.1 (2004): 14-19.
(59) MOTOFEI et al. (2017). Safety Profile of Finasteride: Distribution of Adverse Effects According to Structural and Informational Dichotomies of the Mind/Brain. Clinical Drug Investigation, 37(6), 511-517.
(60) SHIELL et al. (1990). Problems associated with synthetic fibre implants for hair replacement ("NIDO" process). The Medical journal of Australia, 152(10), 560.
(61) TCHERNEV et al. (2016). Biofibre hair implant: what is new, what is true?. Journal of biological regulators and homeostatic agents, 30(2 Supp! 2), 49-56.
(62) SERDEV et al. (2015). Polyamide hair implant (Biofibre®): evaluation of efficacy and safety in a group of 133 patients. Journal of Biological Regulators & Homeostatic Agents, 29(1), 107-113.
(63) SANTIAGO et al. (2007). Artificial hair fiber restoration in the treatment of scalp scars. Dermatologic surgery, 33(1), 35-44.
(64) PALMIERI et al. (2000). Evaluation of polyamide synthetic hair. A long-term clinical study. *Panminerva medica*, 42(1), 49-53.
(65) MYSORE, V. (2010). Controversy: Synthetic hairs and their role in hair restoration?. International journal of trichology, 2(1), 42-44.
(66) WAN et al. (2017). Solvent Bonding for Fabrication of PMMA and COP Microfluidic Devices. JoVE (Journal of Visualized Experiments), (119), e55175-e55175.
(67) VANHOESTENBERGHE et al. (2013). Corrosion of silicon integrated circuits and lifetime predictions in implantable electronic devices. Journal of neural engineering, 10(3), 031002: 1-13.
(68) NIECHAJEV, I. (2012). Facial reconstruction using porous high-density polyethylene (medpor): long-term results. Aesthetic plastic surgery, 36(4), 917-927.
(69) NAYYER et al. (2016). A biodesigned nanocomposite biomaterial for auricular cartilage reconstruction. Advanced healthcare materials, 5(10), 1203-1212.
(70) WIKIPEDIA (2017). Silicone rubber. Wikipedia, the free encyclopedia. https://en.wikipedia.org/w/index.php?title=Silicone rubber&oldid=788264103.
(71) WIKIPEDIA (2017). Injection moulding. Wikipedia, the free encyclopedia. https://en.wikipedia.org/w/index.php?title=Injection_moulding&oldid=794136890.
(72) WIKIPEDIA (2017). Injection molding of liquid silicone rubber. Wikipedia, the free encyclopedia: https://en.wikipedia.org/w/index.php?title=Injection molding of liquid silicone r ubber&oldid=787919147.
(73) CHAVOIN et al. (2016). Correction of congenital malformations by custom-made silicone implants: Contribution of computer-aided design. Experience of 611 cases. In Annales de chirurgie plastique et esthetique, Vol. 61, No. 5, pp. 694-702.
(74) ERLICH et al. (2003). Nasal dorsal augmentation with silicone implants. Facial plastic surgery, 19(04), 325-330.

(75) FANOUS et al. (2003). Estimating implant size in chin augmentation: A simplified approach. Canadian Journal of Plastic Surgery, 11(3), 161-165.
(76) FLECKMAN et al. (2012). Cutaneous and inflammatory response to long-term percutaneous implants of sphere-templated porous/solid poly (HEMA) and silicone in mice. Journal of Biomedical Materials Research Part A, 100(5), 1256-1268.
(77) FLECKMAN et al. (2008). Models for the histologic study of the skin interface with percutaneous biomaterials. Biomedical Materials, 3(3), 034006: 1-24.
(78) MURPHY et al. (2010). The effect of mean pore size on cell attachment, proliferation and migration in collagen-glycosaminoglycan scaffolds for bone tissue engineering. Biomaterials, 31(3), 461-466.
(79) PAE et al. (1975). Design and evaluation of a percutaneous transthoracic cannula. Transactions-American Society for Artificial Internal Organs, 22, 135-148.
(80) BRYERS et al. (2012). Engineering biomaterials to integrate and heal: the biocompatibility paradigm shifts. Biotechnology and bioengineering, 109(8), 1898-1911.
(81) MOORE et al. (2015). Molecular characterization of macrophage-biomaterial. Adv Exp Med Biol. 865: 109-122.
(82) FARRELL et al. (2014). Effects of pore size, implantation time, and nano-surface properties on rat skin ingrowth into percutaneous porous titanium implants. Journal of Biomedical Materials Research Part A, 102(5), 1305-1315.
(83) UNDERWOOD et al. (2011). Quantifying the effect of pore size and surface treatment on epidermal incorporation into percutaneously implanted sphere-templated porous biomaterials in mice. Journal of Biomedical Materials Research Part A, 98(4), 499-508.
(84) KONISHI et al. (2012). Reshaping the eyebrow by follicular unit transplantation from excised eyebrow in extended infrabrow excision blepharoplasty. Clinical ophthalmology (Auckland, NZ), 6, 247-252.
(85) RUTALA et al. (2008). Guideline for disinfection and sterilization in healthcare facilities, 2008. Department of Health and Human Services. Centers for Disease Control and Prevention. pp. 1-161.
(86) FIG. 1 of TEUMER et al. (2005, May). Follicular cell implantation: an emerging cell therapy for hair loss. In Seminars in Plastic Surgery (Vol. 19, No. 02, pp. 193-200).
(87) U.S. Pat. No. 9,492,196 B2 (Keren et al.)
(88) TOYOSHIMA et al. (2012). Fully functional hair follicle regeneration through the rearrangement of stem cells and their niches. Nature communications, 3, 784: 1-12.
(89) DUVERGER et al. (2014). To grow or not to grow: hair morphogenesis and human genetic hair disorders. Seminars in cell & developmental biology. Vol. 25: pp. 22-33.
(90) THIEDKE, C. C. (2003). Alopecia in women. American family physician, 67(5), 1007-1014.
(91) FOX et al. (2007). Traction folliculitis: an underreported entity. Cutis, 79(1), 26-30.
MIRMIRANI et al. (2014). Traction Alopecia. Dermatologic clinics, 32(2), 153-161.
(92) AVITZUR, O. (2013). The dangers of hair extensions: The beauty trend can cause headaches, baldness, and allergic reactions. Consumer Reports. https://www.consumerreports.org/cro/2013/02/the-dangers-of-hair-extensions/index.htm.
(93) AHDOUT et al. (2012). Weft hair extensions causing a distinctive horseshoe pattern of traction alopecia. Journal of the American Academy of Dermatology, 67(6), e294-e295.
(94) WAI, S. (2014). What is hair implant?. Skin health: the creation of beauty is art. http://skinhealthsubang.blogspot.com/2014/08/what-is-hair-implant.html.
(95) UNKNOWN. (2015). Image of Hair transplant surgery scars in donor area with follicular unit extraction technique. http://ae154z115g.previewdomain.jp/wp-content/uploads/2015/11/003_BK2.jpg.
(96) Hair transplant surgery skin pitting. https://www.bing.com/images/search?view=detailV2&ccid=SugtAQeg&id=05E8079A7452B7A438E94F7C8ED83A7F28D2CC38&q=hair+transplant+skin+pitting&simid=608019078156652373&selectedIndex=0&qpvt=hair+transplant+skin+pitting&ajaxhist=0
(97) UNKNOWN. (2013). Image of Galea aponeurotica seen though scalp incision. http://www.the-dermatologist.com/sites/default/files/issues/Screen%20Shot%202013-08-20%20at%209.00.40%20AM.png.
(98) UNKNOWN (2015). Galea aponeurotica diagram. http://www.learnneurosurgery.com/uploads/1/6/6/8/16689668/1813531.jpg?702.
(99) UNKNOWN (2015). Galea aponeurotica diagram with head in view. http://www.buism.com/hairlossfiles/image001.jpg.
(100) AVRAM et al. (2014). Side-effects from follicular unit extraction in hair transplantation. Journal of cutaneous and aesthetic surgery, 7(3), 177-179.
(101) KARAÇAL et al. (2012). Necrosis of the donor site after hair restoration with follicular unit extraction (FUE): a case report. Journal of Plastic, Reconstructive & Aesthetic Surgery, 65(4), e87-e89.
(102) POSWAL et al. (2011). When FUE goes wrong!. Indian journal of dermatology, 56(5), 517-519.
(103) LEPAW, M. I. (1979). Complications of implantation of synthetic fibers into scalps for "hair" replacement: experience with fourteen cases. The Journal of dermatologic surgery and oncology, 5(3), 201-204.
(104) COTSARELIS et al. (2001). Towards a molecular understanding of hair loss and its treatment. Trends in molecular medicine, 7(7), 293-301.
(105) FIG. 1 from COTSARELIS et al. (2001). Towards a molecular understanding of hair loss and its treatment. Trends in molecular medicine, 7(7), 293-301.
(106) BIOFIBRE (2015). Hair Implant Safety. Biofibre: High Technology Hair Implant System. http://www.biofibre.com/en/hair-implants/safety/.
(107) BIOFIBRE (2015). Results. Biofibre: High Technology Hair Implant System. http://www.biofibre.com/en/results/.
(108) UNKNOWN. (2015). Image of Hair transplant surgery scars in donor area with follicular unit extraction technique. http://ae154z115g.previewdomain.jp/wp-content/uploads/2015/11/003 BK2.jpg.
(109) Hair transplant surgery skin pitting. https://www.bing.com/images/search?view=detailV2&ccid=SugtAQeg&id=05E8079A7452B7A438E94F7C8ED83 A7F28D2CC38&q=hair+transplant+skin+pitting&simid=608019078156652373&selectedIndex=0&qpvt=hair+transplant+skin+pitting&ajaxhist=0
(110) UNKNOWN. (2013). Image of Galea aponeurotica seen though scalp incision. http://www.the-dermatologist- .com/sites/default/files/i ssues/Screen%20Shot%202013-08-20%20at%209.00.40%20AM.png.
(111) UNKNOWN (2015). Galea aponeurotica diagram. http://www.learnneurosurgery.com/uploads/1/6/6/8/16689668/1813531.jpg?702.
(112) UNKNOWN (2015). Galea aponeurotica diagram with head in view. http://www.buism.com/hairlossfiles/image001.jpg.
(113) AVRAM et al. (2014). Side-effects from follicular unit extraction in hair transplantation. Journal of cutaneous and aesthetic surgery, 7(3), 177-179.
(114) POSWAL et al. (2011). When FUE goes wrong!. Indian journal of dermatology, 56(5), 517-519.
(115) FOX et al. (2007). Traction folliculitis: an underreported entity. Cutis, 79(1), 26-30.
(116) U.S. Pat. No. 3,596,292 (Erb et al.)
(117) U.S. Pat. No. 5,061,284 (Laghi).

REFERENCE NUMBERS

20. Implant
22. Anchor
22A. Cruciform-Shaped Anchor
22B. Inverted "Y"-Shaped Anchor
22C. Barbed Anchor
22D. Racket-Shaped Anchor
22E. Bar-shaped Anchor
22F. Ovoid-shaped Anchor
22G. Screw-shaped Anchor
24. Vertical Component or Anchor Body
24A. Hair Element Arm
24B. Anchor Arm
24C. Ovoid Anchor Body
26. Bridge
27. Connecting surface 27A and 27B
28. Hair or Hair Element
30. Internal Hair Chamber
32. Distal Orifice
34. Distal End
34A. Upper Surface
34B. Curved Distal Surface
36. Proximal Orifice
38. Proximal Closure of Internal Hair Chamber
40. Proximal End
40A. Proximal End
40B. Proximal End
42. Closed Tunnel (or Closed Void)
42A. Closed Tunnel (or Closed Void)
42B. Closed Tunnel (or Closed Void)
43. Central Point
44. Open Tunnel (or Open Void)
46. Fracture Line
48. Knot Chamber
50. Knot
52. Concavity
54. Proximal Bulbous Shape
56. Epidermis
58. Dermis
60. Follicular Unit
62. Follicle
64. Scalp
66. Undulation
68. Rounded Indentation
70. Protrusion
71. Cup-shaped structure
72. Convexity
74. Horizontal Component or Anchor Body
76. Thread
78. Hair Bundle
80. Ancillary Hair Element
82. Hair Bud Structure

What is claimed is:

1. A hair implant suitable for subcutaneous implantation, comprising:
   (a) an anchor comprising:
      (i) an anchor body having a proximal end and having a distal end, said anchor body comprising a fracture line that runs between said proximal end and said distal end such that said anchor is configured to fracture along said fracture line upon application of sufficient force to facilitate removal; and
      (ii) at least one closed tunnel disposed through said anchor body, said at least one closed tunnel configured to support collagen ligature growth after subcutaneous implant of said hair implant so as to anchor said anchor to a hair implant recipient, said at least one closed tunnel being free of hair; and
   (b) at least one hair strand projecting from said distal end of said anchor body.

2. The anchor of claim 1, wherein the at least one closed tunnel is located along said fracture line.

3. The hair implant of claim 1 wherein said anchor body further comprises an external surface feature that is also configured to support collagen ligature growth after subcutaneous implant of said hair implant so as to also anchor said anchor to the hair implant recipient.

4. The hair implant of claim 1 wherein said at least one closed tunnel comprises two closed tunnels that are aligned between said proximal and distal ends.

5. The hair implant of claim 1, wherein said at least one hair strand is a synthetic hair comprising polymer filaments selected from the group consisting of polypropylene, polyvinyl chloride, polyamide, polyethylene, polyacrylonitrile, polyvinylidene chloride, polyurethane, polyester and copolymers thereof.

6. The hair implant of claim 1, wherein said hair strand is a human hair strand.

7. The hair implant of claim 1 wherein said at least one hair strand forms an exit angle with said distal end of said anchor body.

8. The hair implant of claim 7 wherein said exit angle comprises an angle in a range of 1°-90°.

9. The hair implant of claim 1, wherein said anchor body is constructed from a biocompatible polymer.

10. The hair implant of claim 9 wherein said biocompatible polymer is silicone.

11. The hair implant of claim 1 wherein said anchor body is constructed from a metal.

12. The hair implant of claim 1 wherein said anchor body is constructed from a metal alloy.

13. A hair implant suitable for subcutaneous implantation, comprising:
   (a) an anchor comprising:
      (i) an anchor body having a proximal end and having a distal end, said anchor body comprising a fracture line that runs between said proximal end and said distal end such that said anchor is configured to fracture along said fracture line upon application of sufficient force to facilitate removal; and
      (ii) at least one open tunnel disposed through said anchor body, said at least one open tunnel configured to support collagen ligature growth after subcutaneous implant of said hair implant so as to anchor said anchor to a hair implant recipient, said at least one open tunnel being free of hair; and (b) at least one hair strand projecting from said distal end of said anchor body.

14. The anchor of claim 13, wherein the at least one open tunnel is located along said fracture line.

15. The hair implant of claim 13 wherein said anchor body further comprises an external surface feature that is also configured to support collagen ligature growth after subcutaneous implant of said hair implant so as to also anchor said anchor to the hair implant recipient.

16. The hair implant of claim 13 wherein said at least one open tunnel is located at said proximal end of said anchor body.

17. The hair implant of claim 13, wherein said at least one hair strand is a synthetic hair comprising polymer filaments selected from the group consisting of polypropylene, polyvinyl chloride, polyamide, polyethylene, polyacrylonitrile, polyvinylidene chloride, polyurethane, polyester and copolymers thereof.

18. The hair implant of claim 13, wherein said hair strand is a human hair strand.

19. The hair implant of claim 13 wherein said at least one hair strand forms an exit angle with said distal end of said anchor body.

20. The hair implant of claim 19 wherein said exit angle comprises an angle in a range of 1°-90°.

21. The hair implant of claim 13, wherein said anchor body is constructed from a biocompatible polymer.

22. The hair implant of claim 21 wherein said biocompatible polymer is silicone.

23. The hair implant of claim 13 wherein said anchor body is constructed from a metal.

24. The hair implant of claim 13 wherein said anchor body is constructed from a metal alloy.

* * * * *